(12) United States Patent
Asghar et al.

(10) Patent No.: US 12,277,779 B2
(45) Date of Patent: Apr. 15, 2025

(54) VEHICLE AND MOBILE DEVICE INTERFACE FOR VEHICLE OCCUPANT ASSISTANCE

(71) Applicant: QUALCOMM Incorporated, San Diego, CA (US)

(72) Inventors: Ziad Asghar, San Diego, CA (US); Wesley James Holland, Encinitas, CA (US); Seyfullah Halit Oguz, San Diego, CA (US); Bala Ramasamy, San Marcos, CA (US); Leonid Sheynblat, Hillsborough, CA (US)

(73) Assignee: QUALCOMM Incorporated, San Diego, CA (US)

( * ) Notice: Subject to any disclaimer, the term of this patent is extended or adjusted under 35 U.S.C. 154(b) by 743 days.

(21) Appl. No.: 17/495,748

(22) Filed: Oct. 6, 2021

(65) Prior Publication Data

US 2023/0106673 A1 Apr. 6, 2023

(51) Int. Cl.
*G06V 20/59* (2022.01)
*A61B 5/00* (2006.01)
(Continued)

(52) U.S. Cl.
CPC ........ *G06V 20/597* (2022.01); *A61B 5/02055* (2013.01); *A61B 5/021* (2013.01); *A61B 5/024* (2013.01); *A61B 5/0533* (2013.01); *A61B 5/163* (2017.08); *A61B 5/165* (2013.01); *A61B 5/318* (2021.01); *A61B 5/369* (2021.01);
(Continued)

(58) Field of Classification Search
CPC .... G06V 20/597; G06V 20/58; G06V 20/584; G06V 40/19; G06V 40/20; A61B 5/02055; A61B 5/021; A61B 5/024; A61B 5/0533; A61B 5/163; A61B 5/165; A61B 5/318; A61B 5/369; A61B 5/4561; A61B 5/4809; A61B 5/4845; G08G 1/0112; B60K 35/60; B60K 2360/21; B60K 35/285; B60K 2360/177; B60K 2360/191; B60K 2360/5915; B60K 2360/77; B60K 35/28;
(Continued)

(56) References Cited

U.S. PATENT DOCUMENTS 9,459,692 B1 * 10/2016 Li ........................... G01S 19/14
11,562,550 B1    1/2023 Asghar
(Continued)

FOREIGN PATENT DOCUMENTS

EP         0480825 A2    4/1992
WO    2021059107 A1    4/2021

OTHER PUBLICATIONS

International Search Report and Written Opinion—PCT/US2022/077486—ISA/EPO—Feb. 6, 2023.

*Primary Examiner* — Brandon J Miller
(74) *Attorney, Agent, or Firm* — QUALCOMM Incorporated

(57) ABSTRACT

Systems, methods, and non-transitory media are provided for a vehicle and mobile device interface for vehicle occupant assistance. An example method can include determining, based on one or more images of an interior portion of a vehicle, a pose of a mobile device relative to a coordinate system of the vehicle; determine a state of an occupant of the vehicle; and send, to the vehicle, data indicating the state of the occupant and the pose of the mobile device relative to the coordinate system of the vehicle.

39 Claims, 20 Drawing Sheets

(51) Int. Cl.
*A61B 5/0205* (2006.01)
*A61B 5/021* (2006.01)
*A61B 5/024* (2006.01)
*A61B 5/0533* (2021.01)
*A61B 5/16* (2006.01)
*A61B 5/318* (2021.01)
*A61B 5/369* (2021.01)
*G06V 20/58* (2022.01)
*G06V 40/19* (2022.01)
*G06V 40/20* (2022.01)
*G08G 1/01* (2006.01)

(52) U.S. Cl.
CPC .......... *A61B 5/4561* (2013.01); *A61B 5/4809* (2013.01); *A61B 5/4845* (2013.01); *G06V 20/58* (2022.01); *G06V 20/584* (2022.01); *G06V 40/19* (2022.01); *G06V 40/20* (2022.01); *G08G 1/0112* (2013.01)

(58) Field of Classification Search
CPC ........ B60K 35/29; B60K 35/85; B60K 35/10; B60Y 2400/92
See application file for complete search history.

(56) References Cited

U.S. PATENT DOCUMENTS

| | | | |
|---|---|---|---|
| 2010/0131148 A1* | 5/2010 | Camhi | B60W 40/09 |
| | | | 701/31.4 |
| 2016/0001781 A1 | 1/2016 | Fung et al. | |
| 2017/0329329 A1* | 11/2017 | Kamhi | B60W 50/0098 |
| 2018/0154854 A1 | 6/2018 | Thieberger et al. | |
| 2018/0260642 A1* | 9/2018 | Kim | G06V 10/80 |
| 2019/0088156 A1 | 3/2019 | Choi et al. | |
| 2020/0184841 A1 | 6/2020 | Wickman et al. | |
| 2020/0271450 A1 | 8/2020 | Gorur Sheshagiri et al. | |
| 2020/0294334 A1 | 9/2020 | Palmer et al. | |
| 2021/0118192 A1 | 4/2021 | Sato et al. | |
| 2021/0334536 A1* | 10/2021 | Furlan | G06T 19/006 |
| 2022/0095975 A1* | 3/2022 | Aluf | B60W 60/0051 |
| 2022/0144284 A1* | 5/2022 | Conners | B60W 50/16 |

* cited by examiner

VEHICLE AND MOBILE DEVICE INTERFACE FOR VEHICLE OCCUPANT ASSISTANCE

TECHNICAL FIELD

The present disclosure generally relates to extended reality for vehicle occupant assistance. For example, aspects of the present disclosure relate to vehicle-to-device interfaces for extended reality in vehicles.

BACKGROUND

Many devices and systems allow a scene to be captured by generating images (or frames) and/or video data (including multiple frames) of the scene. For example, a device with a camera can capture a sequence of frames of a scene (e.g., a video of a scene). In some cases, the sequence of frames can be processed for one or more functions, output for display, output for processing and/or consumption by other devices, among other uses. A vehicle is one example of a device that can include one or more cameras. For instance, a vehicle can include cameras that can capture frames of the interior of the vehicle and/or an area(s) outside of the vehicle. The frames can be processed for various purposes, such as determining or recognizing road conditions; identifying other vehicles, objects, pedestrians, and/or obstacles in proximity to the vehicle; among other purposes.

Extended reality (XR) devices are another example of devices that can include one or more cameras. XR devices can include augmented reality (AR) devices, virtual reality (VR) devices, mixed reality (MR) devices, or the like. For instance, examples of AR devices include smart glasses and head-mounted displays (HMDs). In general, an AR device can implement cameras and a variety of sensors to track the position of the AR device and other objects within the physical environment. An AR device can use the tracking information to provide a user of the AR device a realistic AR experience. For example, an AR device can allow a user to experience or interact with immersive virtual environments or content. To provide realistic AR experiences, AR technologies generally aim to integrate virtual content with the physical world. In some examples, AR technologies can match the relative pose and movement of objects and devices. For example, an AR device can use tracking information to calculate the relative pose of devices, objects, and/or maps of the real-world environment in order to match the relative position and movement of the devices, objects, and/or the real-world environment. Using the pose and movement of one or more devices, objects, and/or the real-world environment, the AR device can anchor content to the real-world environment in a convincing manner. The relative pose information can be used to match virtual content with the user's perceived motion and the spatio-temporal state of the devices, objects, and real-world environment.

BRIEF SUMMARY

Systems and techniques are described herein for integrating a mobile device, such as an augmented reality (AR) device, with an operation of a vehicle. According to at least one example, a method is provided for augmented reality for vehicle occupant assistance. The method can include based on one or more images of an interior portion of a vehicle, determining a pose of a mobile device relative to a coordinate system of the vehicle; determining a state of an occupant of the vehicle; and sending, to the vehicle, data indicating the state of the occupant and the pose of the mobile relative to the coordinate system of the vehicle.

According to at least one example, a non-transitory computer-readable medium is provided for augmented reality for vehicle occupant assistance. The non-transitory computer-readable medium can include instructions stored thereon that, when executed by one or more processors, cause the one or more processors to determine, based on one or more images of an interior portion of a vehicle, a pose of a mobile device (e.g., the apparatus) relative to a coordinate system of the vehicle; determine a state of an occupant of the vehicle; and send, to the vehicle, data indicating the state of the occupant and the pose of the mobile relative to the coordinate system of the vehicle.

According to at least one example, an apparatus is provided for augmented reality for vehicle occupant assistance. The apparatus can include memory and one or more processors coupled to the memory, the one or more processors being configured to determine, based on one or more images of an interior portion of a vehicle, a pose of a mobile device (e.g., the apparatus) relative to a coordinate system of the vehicle; determine a state of an occupant of the vehicle; and send, to the vehicle, data indicating the state of the occupant and the pose of the mobile relative to the coordinate system of the vehicle.

According to at least one example, another apparatus is provided for augmented reality for vehicle occupant assistance. The apparatus can include means for based on one or more images of an interior portion of a vehicle, determining a pose of a mobile device relative to a coordinate system of the vehicle; determining a state of an occupant of the vehicle; and sending, to the vehicle, data indicating the state of the occupant and the pose of the mobile relative to the coordinate system of the vehicle.

In some aspects, the method, non-transitory computer-readable medium, and apparatuses described above can determine a context of the vehicle based on the data associated with the one or more sensors. In some examples, the context can include an event related to the vehicle.

In some aspects, the method, non-transitory computer-readable medium, and apparatuses described above can determine an eye gaze of the occupant of the vehicle. In some examples, the state of the occupant includes the eye gaze of the occupant, and the occupant is associated with the mobile device (e.g., the occupant is wearing the mobile device).

In some examples, the state of the occupant can include an impairment of the occupant with regard to operating the vehicle. In some cases, the impairment can include at least one of a state of distraction with respect to at least one of an operation of the vehicle and an event associated with the vehicle, an intoxicated state, a health condition, a wakefulness state, a detected emotional state, an impaired position to control the vehicle, and an impaired view.

In some cases, determining the state of the occupant can include receiving, from the vehicle, data associated with one or more sensors of the vehicle; and determining the state of the occupant based on the data associated with the one or more sensors of the vehicle and the pose of the mobile device. In some examples, the data associated with the one or more sensors of the vehicle indicates at least one of a state of the vehicle and an event associated with the vehicle.

In some examples, the event associated with the vehicle can include at least one of a presence of an object within a path of the vehicle or a threshold proximity to the path of the vehicle, a traffic control associated with the path of the vehicle, and a failure by the vehicle to remain within at least one of a speed limit and a lane marking. In some cases, the object within the path of the vehicle or the threshold proximity to the path of the vehicle can include at least one of a pedestrian, an animal, and another vehicle.

In some cases, determining the state of the occupant can include receiving, from one or more sensors associated with at least one of the mobile device and a wearable device worn by the occupant, one or more health measurements associated with the occupant; and determining the state of the occupant based on the one or more health measurements. In some examples, the one or more health measurements can include at least one of a heart rate, a blood pressure, a body temperature, a galvanic skin response, a measurement of an electrical signal from a heart of the occupant, a measurement of electrical activity of a brain of the occupant, an amount of eye redness, and a pupil size.

In some aspects, determining the state of the occupant can include determining that an eye gaze of the occupant is focused away from a road ahead of the vehicle for a period of time; and determining an impaired state of the occupant based on the eye gaze of the occupant being focused away from the road ahead of the vehicle for the period of time and a determination that the period of time exceeds a threshold period of time.

In some cases, determining that the eye gaze of the occupant is focused away from the road ahead of the vehicle for the period of time can include determining that the eye gaze of the occupant is focused on virtual content rendered by the mobile device for at least a portion of the period of time.

In some examples, determining that the eye gaze of the occupant is focused away from the road ahead of the vehicle for the period of time can include determining that the eye gaze of the occupant is focused in a different direction than a direction of an obstacle within a path of the vehicle or a threshold proximity to the path of the vehicle.

In some aspects, the method, non-transitory computer-readable medium, and apparatuses described above can send an indication of the state of the occupant to at least one of a second vehicle, a vehicle infrastructure system, a first remote device associated with a second occupant of the second vehicle, and a second remote device associated with a pedestrian.

In some cases, determining the state of the occupant can include determining an eye gaze of the occupant wearing the mobile device; and determining the state of the occupant based on the pose of the mobile device and the eye gaze of the occupant.

In some examples, determining the pose of the mobile device can include receiving, from the vehicle, a vehicle template that includes one or more markers associated with the vehicle; and determining the pose of the mobile device relative to the coordinate system of the vehicle based on the one or more images and the vehicle template.

In some examples, the one or more markers can include at least one of a visual pattern on at least one of an area within the interior portion of the vehicle and an object affixed to the interior portion of the vehicle, an element of the interior portion of the vehicle, a surface within the interior portion of the vehicle, and an illuminated object inside of the vehicle.

In some examples, the one or more images depict the one or more markers, and determining the pose of the mobile device can include detecting the one or more markers in the one or more images; and determining the pose of the mobile device relative to the coordinate system of the vehicle based on the detected one or more markers and the vehicle template.

In some aspects, the method, non-transitory computer-readable medium, and apparatuses described above can obtain, using one or more image sensors of the mobile device, a set of images of the interior portion of the vehicle, the set of images depicting one or more visual landmarks associated with the vehicle; and generate a vehicle template based on the set of images. In some examples, the vehicle template can include the one or more visual landmarks.

In some cases, determining the pose of the mobile device can include obtaining inertial sensor data associated with the mobile device; and determining the pose of the mobile device based on the one or more images and the inertial sensor data.

In some aspects, each of the apparatuses described above is, can be part of, or can include a mobile device, a wearable device, a camera system, a personal computing device, and/or an extended reality (XR) device (e.g., a virtual reality (VR) device, an augmented reality (AR) device, or a mixed reality (MR) device). In some examples, the apparatuses can include or be part of and/or interfaced with a vehicle, a mobile device (e.g., a mobile telephone or so-called "smart phone" or other mobile device), a wearable device, a personal computer, a laptop computer, a tablet computer, a server computer, a robotics device or system, an aviation system, or other device. In some aspects, the apparatus includes an image sensor (e.g., a camera) or multiple image sensors (e.g., multiple cameras) for capturing one or more images. In some aspects, the apparatus includes one or more displays for displaying one or more images, notifications, and/or other displayable data. In some aspects, the apparatus includes one or more speakers, one or more light-emitting devices, and/or one or more microphones. In some aspects, the apparatuses described above can include one or more sensors. In some cases, the one or more sensors can be used for determining a pose of the apparatuses, a state of the apparatuses (e.g., a tracking state, an operating state, a temperature, a humidity level, and/or other state), and/or for other purposes. As used herein, the term pose refers to the position and orientation an apparatus, sensor, or other real-world device or structure relative to a coordinate system.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

BRIEF DESCRIPTION OF THE DRAWINGS

Illustrative examples of the present application are described in detail below with reference to the following figures.

DETAILED DESCRIPTION

Figure 1:
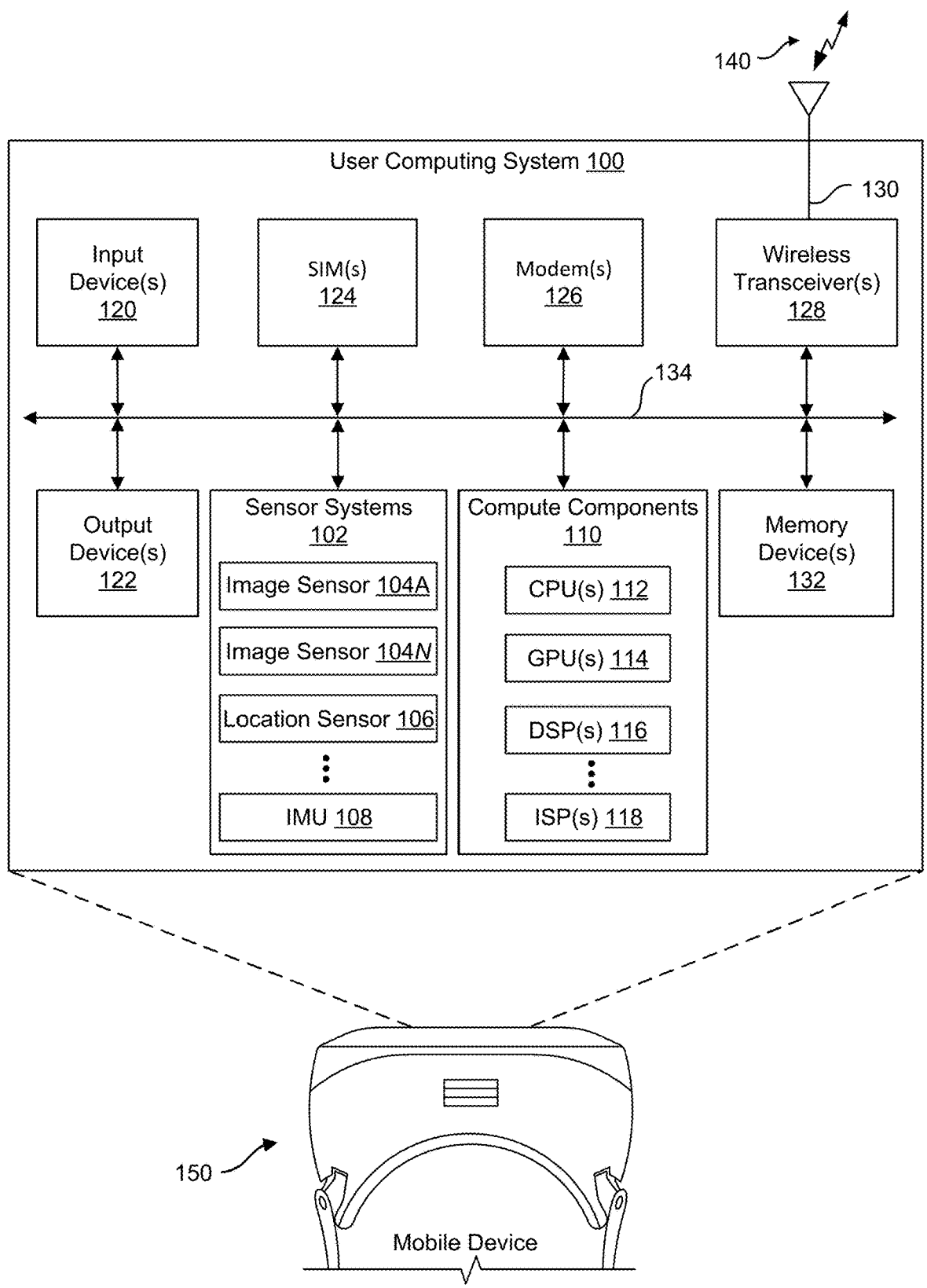
FIG. 1 is a diagram illustrating an example of a computing system of a mobile device, in accordance with some examples of the present disclosure.

Certain aspects and embodiments of this disclosure are provided below. Some of these aspects and embodiments may be applied independently and some of them may be applied in combination as would be apparent to those of skill in the art. In the following description, for the purposes of explanation, specific details are set forth in order to provide a thorough understanding of embodiments of the application. However, it will be apparent that various embodiments may be practiced without these specific details. The figures and description are not intended to be restrictive.

The ensuing description provides example embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the scope of the application as set forth in the appended claims.

Extended reality (XR) systems or devices can provide virtual content to a user and/or can combine real-world or physical environments and virtual environments (made up of virtual content) to provide users with XR experiences. The real-world environment can include real-world objects (also referred to as physical objects), such as books, people, vehicles, buildings, tables, chairs, and/or other real-world or physical objects. XR systems or devices can facilitate interaction with different types of XR environments (e.g., a user can use an XR system or device to interact with an XR environment). XR systems can include virtual reality (VR) systems facilitating interactions with VR environments, augmented reality (AR) systems facilitating interactions with AR environments, mixed reality (MR) systems facilitating interactions with MR environments, and/or other XR systems. As used herein, the terms XR system and XR device are used interchangeably. Examples of XR systems or devices include head-mounted displays (HMDs), smart glasses, among others. In some cases, an XR system can track parts of the user (e.g., a hand and/or fingertips of a user) to allow the user to interact with items of virtual content.

AR is a technology that provides virtual or computer-generated content (referred to as AR content) over the user's view of a physical, real-world scene or environment. AR content can include virtual content, such as video, images, graphic content, location data (e.g., global positioning system (GPS) data or other location data), sounds, any combination thereof, and/or other augmented content. An AR system or device is designed to enhance (or augment), rather than to replace, a person's current perception of reality. For example, a user can see a real stationary or moving physical object through an AR device display, but the user's visual perception of the physical object may be augmented or enhanced by a virtual image of that object (e.g., a real-world car replaced by a virtual image of a DeLorean), by AR content added to the physical object (e.g., virtual wings added to a live animal), by AR content displayed relative to the physical object (e.g., informational virtual content displayed near a sign on a building, a virtual coffee cup virtually anchored to (e.g., placed on top of) a real-world table in one or more images, etc.), and/or by displaying other types of AR content. Various types of AR systems can be used for gaming, entertainment, and/or other applications.

In some cases, two types of AR systems that can be used to provide AR content include video see-through (also referred to as video pass-through) displays and optical see-through displays. Video see-through and optical see-through displays can be used to enhance a user's visual perception of real-world or physical objects. In a video see-through system, a live video of a real-world scenario is displayed (e.g., including one or more objects augmented or enhanced on the live video). A video see-through system can be implemented using a mobile device (e.g., video on a mobile phone display), an HMD, or other suitable device that can display video and computer-generated objects over the video.

An optical see-through system with AR features can display AR content directly onto the view of the real-world scene (e.g., without displaying video content of the real-world scene). For example, the user may view physical objects in the real-world scene through a display (e.g., glasses or lenses), and the AR system can display AR content (e.g., projected or otherwise displayed) onto the display to provide the user with an enhanced visual perception of one or more real-world objects. Examples of optical see-through AR systems or devices are AR glasses, an HMD, another AR headset, or other similar device that can include a lens or glass in front of each eye (or a single lens or glass over both eyes) to allow the user to see a real-world scene with physical objects directly, while also allowing an enhanced image of that object or additional AR content to be projected onto the display to augment the user's visual perception of the real-world scene.

VR provides a complete immersive experience in a three-dimensional computer-generated VR environment or video depicting a virtual version of a real-world environment. The VR environment can be interacted with in a seemingly real or physical way. As a user experiencing a VR environment moves in the real world, images rendered in the virtual environment also change, giving the user the perception that the user is moving within the VR environment. For example, a user can turn left or right, look up or down, and/or move forwards or backwards, thus changing the user's point of view of the VR environment. The VR content presented to the user can change accordingly, so that the user's experience is as seamless as in the real world. VR content can include VR video in some cases, which can be captured and rendered at very high quality, potentially providing a truly immersive virtual reality experience. Virtual reality applications can include gaming, training, education, sports video, online shopping, among others. VR content can be rendered and displayed using a VR system or device, such as a VR HMD or other VR headset, which fully covers a user's eyes during a VR experience.

MR technologies can combine aspects of VR and AR to provide an immersive experience for a user. For example, in an MR environment, real-world and computer-generated objects can interact (e.g., a real person can interact with a virtual person as if the virtual person were a real person).

Systems, apparatuses, methods (also referred to as processes), and computer-readable media (collectively referred to herein as "systems and techniques") are described herein for integrating data, functionalities, actions, and/or device capabilities from vehicles and mobile (portable and/or wearable) devices, such as XR devices (e.g., augmented reality (AR) or mixed reality (MR) devices, virtual reality (VR) devices, etc.), wearable devices with networking/communication capabilities, smart phones, personal computing devices, etc. In some examples, the systems and techniques described herein can provide assistance to an occupant of a vehicle using data and/or functionalities from an XR device (e.g., an AR device, MR device, etc.) and/or the vehicle. For example, in some cases, the systems and techniques described herein can provide a vehicle-to-device (e.g., vehicle to mobile computing device) interface for augmented reality assistance to an occupant of the vehicle.

In some examples, a vehicle can include cameras that can capture frames of the interior of the vehicle and/or an area(s) outside of the vehicle (e.g., the vehicle surroundings). The frames can be processed for various purposes, such as determining or recognizing road conditions; recognizing an identity of a person(s) in the vehicle; identifying other vehicles, objects, pedestrians, and/or obstacles in proximity to the vehicle; determining and/or recognizing activities and/or events in an environment associated with the vehicle (e.g., an environment outside of the vehicle, an environment inside of the vehicle, etc.); among others. A vehicle can also include and/or implement other types of sensor systems to measure and/or determine a variety of conditions. For example, in some cases, a vehicle can include and/or implement one or more radio detection and raging (RADAR) systems, inertial measurement units (IMUs), light detection and ranging (LIDAR) systems, ultrasonic sensors, radio frequency (RF) sensors, sound navigation and ranging (SO-NAR) systems, electromagnetic detection and ranging (Em-DAR) systems, sound detection and ranging (SODAR) systems, global navigation satellite system (GNSS) receiver systems (e.g., one or more global positioning system (GPS) receiver systems), accelerometers, gyroscopes, speed sensors, infrared sensor systems, laser rangefinder systems, ultrasonic sensor systems, infrasonic sensor systems, microphones, any combination thereof, and/or other sensor systems.

A mobile device, such as an XR device (e.g., a head-mounted display AR device, AR smart glasses, or other XR device), can also include one or more cameras that can capture images and/or video. For example, an AR device can implement cameras and a variety of sensors to determine and/or track the position of the AR device and other objects within the physical environment. An AR device can use the tracking information to provide a user of the AR device a realistic AR experience. For example, an AR device can allow a user to experience or interact with immersive virtual environments or content. As noted above, to provide realistic AR experiences, AR technologies generally aim to integrate virtual content with the physical world. In some examples, an AR device can use tracking information from one or more sensors to calculate the relative pose of devices, objects, and/or maps of the real-world environment in order to match the relative position and movement of the devices, objects, and/or the real-world environment. Using the pose and movement of one or more devices, objects, and/or the real-world environment, the AR device can anchor content to the real-world environment in a convincing manner. The relative pose information can be used to match virtual content with the user's perceived motion and the spatio-temporal state of the devices, objects, and real-world environment.

A user of an XR device (e.g., an AR device) may sometimes wear the XR device while the user is in a vehicle (e.g., while the user is driving the vehicle or as a passenger in the vehicle). For example, in some cases, a user may wear an AR device while operating (e.g., driving) the vehicle. In some cases, the user wearing the AR device and operating the vehicle (e.g., the driver) may be impaired by one or more conditions such as, for example, distractions. In other words, the user's ability to operate the vehicle may be impaired by such conditions. The distractions can be caused by a variety of things such as causes external to the user. For example, a user can be distracted by virtual content rendered by the AR device (e.g., email notifications, world-locked virtual billboards or signs, application content, video and/or image content, interface content, etc.), objects and/or activity occurring in an environment outside of the vehicle, objects and/or events occurring inside of the vehicle, other occupants of the vehicle, thoughts and/or inattentiveness (e.g., daydreaming, etc.), sound or noise (e.g., inside and/or outside of the vehicle), user devices, etc.

Even without such distractions, the occupant of the vehicle (e.g., the driver) may generally suffer from other impairments. The other impairments can include and/or result from certain physical and/or personal limitations and/or conditions such as, for example, a limited perception, a limited attention, real-world events and conditions, sleep deprivation, intoxication, health conditions, etc. For example, the occupant (e.g., the driver) of the vehicle wearing the AR device may have a difficult time seeing certain areas/views of the vehicle's surroundings from the point-of-view or field-of-view of the occupant (e.g., an area behind the vehicle, an area under the vehicle, an area close to an exterior of the vehicle, an area occluded/obstructed by one or more objects and/or conditions (e.g., poor lighting, etc.), an area above the vehicle, an area a certain distance away from the vehicle, etc.). Moreover, certain road conditions may not be visible to or may be difficult to see by an occupant of the vehicle, such as standing water, ice, obstructions beyond the reach of one or more lights (e.g., the headlights, fog lights, off-road lights, emergency lights, signaling lights, daytime running lights, reverse lights, tail lights, brake lights, etc.) of the vehicle, etc. The occupant of the vehicle can also be distracted by certain events and objects, such as a passing vehicle, a pedestrian, surrounding activity/events, a navigation alert, etc. In some cases, such impairments can prevent or hamper a driver's ability to safely operate the vehicle or respond to driving conditions.

In some aspects, the systems and techniques described herein can allow a vehicle and an XR device (e.g., an AR device) to interface with each other, such as to share/integrate data, functionalities, actions, and/or device capabilities from the vehicle and the XR device. Interfacing with one another and sharing/integrating data can allow the vehicle and the XR device (e.g., the AR device) to provide assistance to an occupant of the vehicle such as, for example, the driver/operator of the vehicle, a vehicle passenger, etc. In some examples, an XR device (e.g., an AR device) can use data from the vehicle and/or one or more sensors on the XR device to localize itself (determine its position and/or orientation, in general its pose) within the vehicle (e.g., within an internal portion of the vehicle such as the vehicle cabin). In some cases, the XR device can implement a localization process that can perform imaging-based (e.g., vision-based) and/or audio-based (e.g., via audio beamforming) localization of in-vehicle landmarks/markers (e.g., quick response (QR) codes inside of the vehicle, lights inside of the vehicle, objects inside of the vehicle (e.g., doors, windows, seats, headrests, dashboard components, vehicle control systems (e.g., steering wheel, horn, signaling systems, etc.), patterns inside of the vehicle, shapes inside of the vehicle, etc.). The localization process can use such in-vehicle landmarks/markers to localize the XR device within the vehicle. For example, the localization process can use the in-vehicle landmarks/markers to determine a pose of the XR device relative to a coordinate system of the XR device and/or the vehicle.

In some cases, the localization process can detect the in-vehicle landmarks based on data from one or more devices (e.g., sensors, emitters, transceivers, imaging devices, etc.) on the XR device (e.g., the AR device), such as one or more cameras, radio interfaces, ultrasonic sensors, radars, etc. Auxiliary sensor data, e.g., from one or more IMUs, can be used to track the pose of the XR device. In some cases, the localization process can use a vehicle template to determine a position of the XR device relative to one or more in-vehicle landmarks specified in the vehicle template and detected as described above. For example, the localization process can use the vehicle template to identify one or more in-vehicle landmarks it can use for localization. In some cases, the vehicle template can specify coordinates, such as position and/or orientation information, of one or more in-vehicle landmarks, which the localization process can use to localize itself relative to a coordinate system of the XR device (e.g., AR device) and/or the vehicle. For example, the localization process can use data from one or more devices (e.g., sensors, emitters, transceivers, etc.) as described above to detect one or more in-vehicle landmarks identified in the vehicle template. The vehicle template can specify coordinates of the one or more in-vehicle landmarks, which can define the position and/or orientation of the one or more in-vehicle landmarks relative to a coordinate system of the vehicle. The vehicle template can be vehicle-specific or specific to a vehicle model, make, series, class, or combinations thereof. The localization process can use the coordinates specified in the vehicle template to determine the position and/or orientation, relative to the coordinate system of the vehicle, of the one or more in-vehicle landmarks detected by the XR device (e.g., AR device). The localization process can transform, translate, and/or correlate the location and/or orientation of the one or more in-vehicle landmarks relative to the coordinate system of the vehicle to a location and/or orientation relative to a coordinate system of the XR device. The XR device (e.g., AR device) can use the location and/or orientation information associated with the one or more in-vehicle landmarks to understand, determine, and/or track the pose of the XR device within the vehicle and relative to the coordinate system of the XR device and/or the coordinate system of the vehicle.

In some aspects, the XR device can implement an occupant monitoring process, such as a driver monitoring process, that can monitor a user for impairment based on a status of the vehicle, a position/orientation of the occupant, virtual content rendered by the XR device, eye tracking using one or more cameras on the XR device, inertial sensor data, audio sensor data, radar data, radio signals, etc. In some examples, the XR device can include a virtual content filtering process that can filter or block virtual content from being presented to the occupant (e.g., a driver or passenger) based on a status from the vehicle and the occupant monitoring process. A vehicle user interface process can render user interface elements based on, for example, a status from the vehicle and the occupant monitoring process.

In some cases, the vehicle can implement a vehicle monitoring process that can recognize and monitor a status and/or events related to the vehicle, an occupant of the vehicle, and/or the vehicle's surroundings. The vehicle monitoring process can send data about such conditions/events to an XR device (e.g., AR device) in wireless communication, e.g., paired, with the vehicle (e.g., via a wireless radio link). The XR device can use such data for the occupant monitoring process, the virtual content filtering process, the vehicle user interface process, etc. In some examples, the vehicle can implement an event mitigation process that can alter a vehicle operation and/or an autonomous driving policy based on occupant (e.g., driver) monitoring events generated by the XR device, such as occupant conditions and/or activity detected by the XR device.

As previously noted, in some cases, the in-vehicle localization process of an XR device (e.g., AR device) can allow the XR device to understand the pose of the XR device within the vehicle. The XR device can use the localization process to determine its pose relative to and/or within a coordinate system of the vehicle. For example, in order to render data and/or events from vehicle-based sensors and/or instructions, the XR device can use the localization process to obtain a common understanding of the pose of the XR device relative to a coordinate system of the vehicle. In some cases, the localization process can perform a transform from the vehicle's coordinate system to the XR's coordinate system. In some cases, to help the XR device localize itself within the vehicle and/or map the inside of the vehicle in three-dimensional (3D) space, the vehicle can provide a vehicle template to the XR device. The vehicle template can include, for example and without limitation, visual, IR, and/or RF descriptors of one or more in-vehicle landmarks. Non-limiting examples of in-vehicle landmarks can include visual patterns (e.g., QR codes, calibration patterns such as checkerboard patterns, inscriptions/engravings, patterned materials, labels, etc.) affixed to an object or area in an interior portion (e.g., the cabin) of the vehicle (e.g., an object/area in the cabin, an area on the windshield, an object/area on the dashboard, an object/area on a door, an object/area on a seat, etc.), active illumination (e.g., light-emitting diodes (LEDs), etc.) affixed to an object and/or area in the interior portion of the vehicle, an immovable element of the interior portion of the vehicle (e.g., the instrument cluster, a corner(s) of the dashboard, a corner(s) of a window(s) and/or the windshield, a roof of the vehicle, a center console of the vehicle, etc.), a movable element of the interior portion of the vehicle with a known position/offset from the body of the vehicle (e.g., a passenger seat(s), the steering wheel, etc.), among others. In some examples, the vehicle template can include/specify the location and/or orientation of the in-vehicle landmarks relative to the vehicle's coordinate system.

The localization process of the XR device (e.g., AR device) can use the in-vehicle landmarks/markers, the visual, IR and/or RF descriptors, and the location and/or orientation information to localize itself relative to the in-vehicle landmarks and the coordinate system of the vehicle. For example, using one or more cameras of the XR device, the XR device can implement a localization process to (continuously) search for in-vehicle landmarks specified in the vehicle template, and localize itself relative to the in-vehicle landmarks and (by extension) the vehicle. In some cases, the XR device can also use other sensors/devices to aid in the localization such as, for example, a WiFi device, a Bluetooth device, an ultrasonic device, an IMU, etc.

The vehicle monitoring process can monitor a status of the XR device (e.g., AR device), the vehicle, and/or one or more surroundings, etc. The vehicle monitoring process can recognize events related to the vehicle and its surroundings, driving conditions, road conditions, vehicle conditions, etc. The vehicle monitoring process can send data about these events to the XR device, which the XR device can use for the occupant monitoring process, the virtual content filtering process, the vehicle user interface process, etc. Non-limiting examples of data provided by the vehicle monitoring process to the XR device can include instrumentation readings; sensor data (e.g., camera data, RADAR data, SONAR data, SODAR data, EmDAR data, GNSS data, LIDAR data, IMU data, GPS data, etc.), Internet data indicating conditions in the vehicle's path (e.g., weather conditions, traffic conditions, road conditions, etc.), navigation information, etc. In some examples, the sensor data may be pre-processed by the vehicle, e.g., by applying image processing, sensor fusion, object/subject detection, and the like, before being provided to the XR device. In some examples, at least some sensor data may be provided unprocessed to the XR device.

In some examples, the sensor data can indicate a state or status of the vehicle, such as an operational state of the vehicle, a motion state of the vehicle, an autonomous driving policy, a vehicle-related event, e.g., a malfunction of a vehicle component or a sensor-triggered alert, and combinations thereof, a presence of an object or obstruction in or approaching the vehicle's path (e.g., in some cases determined via a machine learning classifier trained on positive and negative examples), a presence of a pedestrian in or approaching the vehicle's path (e.g., in some cases determined via a machine learning classifier trained on positive and negative examples), a presence of something (e.g., a pot hole, an accident, an animal, uneven road portions, lane markings, etc.) in the vehicle's path (e.g., in some cases determined via a machine learning classifier trained on positive and negative examples), a presence of an object (e.g., an emergency vehicle, etc.) behind or near the vehicle's path (e.g., in some cases determined via a machine learning classifier trained on positive and negative examples), etc. In some cases, the sensor data can indicate traffic controls (e.g., stop signs, stop lights, etc.) along the vehicle's path (e.g., in some cases determined via a machine learning classifier trained on positive and negative examples), that the vehicle is violating lane markings (e.g., in some cases determined via a machine learning classifier trained on positive and negative examples), that the vehicle is exceeding the speed limit (e.g., in some cases determined based on the vehicle's speedometer and a database of speed limit zones), etc.

In some cases, the vehicle monitoring process can provide an XR device (e.g., AR device) vehicle-to-everything (V2X) (e.g., vehicle-to-vehicle (V2V), vehicle-to-infrastructure (V2I), etc.) data and/or events. Non-limiting examples of V2X data that the vehicle monitoring process can provide the XR device include V2X data indicating a presence of an obstruction in the vehicle's path, V2X data indicating the presence of a pedestrian in or approaching the vehicle's path, V2X data indicating the presence of something (e.g., a pot hole, an animal, an object, etc.) in the vehicle's path, V2X data indicating a presence of an emergency vehicle behind or near the vehicle's path, V2X data indicating a presence of traffic controls (e.g., a stop sign, a stop light, etc.) along the vehicle's path, V2X data indicating that the vehicle is violating lane markings, V2X data indicating that the vehicle is exceeding a speed limit, V2X data indicating a presence of certain conditions, (e.g., weather conditions, road conditions, traffic conditions, an accident, etc.) in the vehicle's path, etc.

In some examples, the occupant monitoring process can monitor a user/occupant for impairment based on event data and/or status information from the vehicle, virtual content rendered by the XR device (e.g., AR device), a position/orientation of the occupant, user activity (e.g., gestures, movement, etc.), eye tracking, inertial sensor data, audio data (e.g., speech data, acoustic data, sound waves, etc.), a user head pose, etc. In some cases, occupant (e.g., driver, passenger, etc.) impairment may be detected independent of virtual content rendered by the XR device and/or the vehicle status. For example, in some cases, occupant impairment can be detected using sensor data and/or sensor data processing such as, for example, eye-tracking, inertial sensing, heart rate information, temperature data. In some cases, the eye-tracking, inertial sensing, heart rate information, temperature data, etc., can indicate (e.g., in some cases determined via a machine learning classifier trained on positive and negative examples) drowsiness, intoxication, a health emergency (e.g., a seizure, a heart attack, a loss of consciousness, etc.), stress or heightened emotion states general inattention/distraction, etc. In some cases, impairment can be detected using a combination of virtual content, vehicle status information, and/or sensor data. For example, in some cases, occupant impairment can be detected based on eye-tracking data indicating that the occupant's eye gaze has been focused on virtual content for a certain (configurable) period of time, eye-tracking data indicating that the occupant's gaze is focused elsewhere when the vehicle event monitor detects an imminent event or object (e.g., an obstruction, a pedestrian, a pot hole, an animal, etc.), ray tracing of the occupant's gaze, the vehicle template, location information in a reported vehicle event, sensor data indicating a position and/or movement of the occupant, etc.

In some cases, the XR device can modulate/modify (e.g., via the virtual content filtering process and/or the user interface process) virtual content presented by the XR device to the occupant. For example, the XR device can modulate virtual content in response to a determination by the occupant monitoring process that the occupant is impaired, a report from the vehicle monitoring process that a vehicle event is imminent or occurring, a determination that virtual content requested by the occupant may distract the occupant away from certain driving and/or related events, etc. In some examples, the XR device can modulate virtual content by disabling, dimming, or increasing a transparency of all virtual content except a subset of virtual content marked as needed (e.g., head-up display (HUD) content, vehicle instrumentation content, etc.), any portion of virtual content on which the occupant is focused (e.g., in some cases determined based on ray tracing of the occupant's gaze and/or image data capturing the occupant's gaze), any virtual content that is obscuring the vehicle event (e.g., in some cases determined based on ray tracing from the XR device to the location of the vehicle event, the vehicle template, and/or information in the reported vehicle event), etc.

In some cases, in addition to disabling distracting virtual content, the AR device can render other virtual content to rouse an impaired occupant and/or emphasize an imminent or occurring vehicle event. In some examples, the XR device can pulse an edge of the occupant's field-of-view (FOV), circle or highlight the location of the vehicle event in a displayed image/video, render head-locked arrows, pulse the periphery of the occupant's vision, use other directional indicators to direct the occupant's head and/or gaze in the direction of a vehicle event, stream a vehicle camera feed (e.g., a backup camera, a side-view camera, etc.) near the location of the vehicle event, stream vehicle status (e.g., instrumentation, etc.) as a head-locked HUD or world-locked user interface (UI) element, render a warped and/or perspective-corrected exterior view locked to an area of the vehicle (e.g., the vehicle wall, etc.) such that the vehicle appears transparent or translucent and the vehicle event is visible, render virtual content to replace distracting real-world content (e.g., billboards, accidents, etc.). In some cases, such virtual content can be rendered using a deep neural network trained to generate synthetic or "deepfaked" virtual content from a database of images and rendered in the style observed by the AR device and/or the vehicle.

The vehicle monitoring process can send vehicle events to the XR device (e.g., AR device), as previously explained. Similarly, the occupant monitoring process of the XR device may send occupant monitoring events (e.g., impairment, etc.) to the vehicle. In some examples, the vehicle may have some autonomous or semi-autonomous driving capability which may benefit from knowledge of occupant monitoring events generated by the XR device. The vehicle can use such events as part of the autonomous driving policy or capability. For example, upon receiving an occupant monitoring event indicating impairment of the occupant (e.g., the driver), the vehicle can engage an autonomous capability to alert the occupant and/or prevent certain events or risks associated with impaired driving, increase the level or confidence of an already-engaged autonomous capability, etc. In some examples, upon receiving an occupant monitoring event indicating a health emergency, the vehicle can engage an autonomous capability to safely stop the vehicle or proceed to a certain location for assistance (e.g., a hospital, a clinic, etc.). In some cases, the vehicle can use an online or reinforcement learning algorithm to learn, over time, which vehicle and/or world events have a higher correlation with particular driver states (e.g., particular impairments, etc.), and use that information to handle and/or avoid such situations. For example, if the occupant is often distracted by billboards, the vehicle may reduce a speed or enable emergency breaking more aggressively in environments with a billboard.

In some cases, the XR device can use data from one or more wearable devices of the occupant to aid the occupant monitoring process. A wearable device can have additional and/or redundant sensor modalities that can aid the occupant monitoring. The wearable device can send such data (or a digest of relevant events) to the XR device to aid in its occupant monitoring process. In some examples, the wearable device can send the XR device sensor data such as, for example, inertial sensor data, heart rate measurements, blood pressure measurements, galvanic skin response measurements, ECG/EKG/EEG data, temperature data, oxygen levels, motion information, sleep tracking information, etc. In some cases, the data from the wearable device can indicate and/or can be used to determine (e.g., via a machine learning classifier trained on positive and negative examples) impairments such as drowsiness, intoxication, a health emergency, stress, a heightened emotional state, loss of consciousness, etc.

In some cases, the XR device can obtain occupant monitoring information from the vehicle. For example, in some cases, the vehicle can incorporate its own occupant monitoring capabilities/functionalities. In some cases, the XR device can send to the vehicle raw occupant monitoring data from the occupant monitoring process of the XR device for fused processing with the vehicle's occupant monitoring system (e.g., in addition to or instead of sending the vehicle processed occupant monitoring events).

In some cases, the vehicle can send occupant monitoring events to infrastructure and/or other vehicles to allow for mitigation of driver events. For example, the vehicle can report to other vehicles that its driver is impaired so the other vehicles can take precautions, alter their autonomous driving policy (e.g., slow down, give the impaired driver a wide berth, etc.), inform their drivers' XR device (e.g., which in some cases can then highlight or otherwise indicate with virtual content that the nearby vehicle has an impaired driver), etc. In some cases, the vehicle can report that its driver is impaired to a pedestrian crossing infrastructure (e.g., so a crossing signal can prevent pedestrians from crossing in front of a vehicle with an impaired driver, etc.), to law enforcement (e.g., for assistance and/or protection), an XR device of a pedestrian (e.g., so the pedestrian's XR device can render virtual content signaling an impaired driver, etc.). In some cases, the vehicle can render any of the virtual content described herein with respect to the XR device. For example, the vehicle can render same content and/or type of content as described herein with respect to the XR and/or mobile device. The vehicle can render such content in addition to or in lieu of any content rendering by the XR device.

Various aspects of the application will be described with respect to the figures.

FIG. 1 is a diagram illustrating an example of a computing system 100 of a mobile device 150. The mobile device 150 is an example of a computing device that can be used by an end user. For example, the mobile device 150 can include a portable device, a mobile phone, an XR device (e.g., an HMD, smart glasses, etc.), a tablet computer, a laptop computer, a wearable device (e.g., a smart watch, etc.), a connected or Internet-of-Things (IoT) device, and/or any other device used by a user to communicate over a wireless communications network. The computing system 100 includes software and hardware components that can be electrically or communicatively coupled via a communication system 134 such as a bus (or may otherwise be in communication, as appropriate).

The computing system 100 can include one or more sensor systems 102, compute components 110, one or more input devices 120 (e.g., a mouse, a keyboard, a touch sensitive screen, a touch pad, a keypad, a microphone, a controller, and/or the like), one or more output devices 122 (e.g., one or more displays, a speaker, a light-emitting device, a printer, a projector, etc.), one or more modems 126, one or more wireless transceivers 128, one or more antennas 130, and/or one or more memory devices 132. In some cases, the computing system 100 can optionally include one or more SIMs 124. The computing system 100 can include a communication system 134 (e.g., a bus) that can transfer data between components of the computing system 100. In some examples, the one or more output devices 122 can include a left and a right display of the mobile device 150, such as an HMD, smart glasses, or the like. In some examples, the one or more output device 122 can include a rear display and/or a front display of the mobile device 150, such as a smart phone, a smart watch, or the like. In some cases, the one or more output devices 122 can include one or more optical devices such as one or more projectors.

In some examples, the communication system 134 can interconnect the one or more sensor systems 102, the compute components 110, the one or more input devices 120, the one or more output devices 122, the one or more modems 126, the one or more wireless transceivers 128, the one or more antennas 130, and/or the one or more memory devices 132. For example, in some cases, the compute components 110 can use the communication system 134 to communicate between processing processors/cores and/or with any devices/components of the computing system 100 such as, for example, the one or more sensor systems 102, the one or more input devices 120, the one or more output devices 122, the one or more SIMs 124, the one or more modems 126, the one or more wireless transceivers 128, the one or more antennas 130, and/or the one or more memory devices 132.

The compute components 110 can include, for example, one or more central processing units (CPUs) 112, graphics processing units (GPUs) 114, digital signal processors (DSPs) 116, and/or image signal processors (ISPs) 118. In some cases, the compute components 110 can additionally or alternatively include one or more other processing components that are not shown in FIG. 1 such as, for example and without limitation, one or more application-specific integrated circuits (ASICs), field-programmable gate arrays (FPGAs), application processors (APs), vision processing units (VPUs), neural network signal processors (NSPs), microcontrollers, computer vision (CV) processors, dedicated hardware, any combination thereof, and/or other processing devices or systems. In some cases, the one or more compute components 110 can include other electronic circuits or hardware, computer software, firmware, or any combination thereof, to perform any of the various operations described herein. In some examples, the one or more compute components 110 can include more or less compute components than those shown in FIG. 1. Moreover, the CPU 112, the GPU 114, the DSP 116, and the ISP 118 are merely illustrative examples of compute components provided for explanation purposes.

The computing system 100 can use the one or more compute components 110 to perform various computing operations such as, for example, extended reality operations (e.g., tracking, localization, object detection, classification, pose estimation, mapping, content anchoring, content rendering, etc.), device control operations, image/video processing, graphics rendering, event mapping, machine learning, data processing, modeling, calculations, computer vision, event monitoring, any of the operations described herein, and/or any other operations. For example, in some cases, the one or more compute components 110 can perform image/video processing, event mapping, XR processing, device management/control, and/or other operations as described herein using data from the sensor systems 102, the one or more input devices 120, the one or more SIMs 124, the one or more modems 126, the one or more wireless transceivers 128, the one or more antennas 130, the one or more memory devices 132, the vehicle computing system 210 shown in FIG. 2, and/or any other devices.

To illustrate, in some examples, the one or more compute components 110 can perform monitoring (e.g., device monitoring, user monitoring, vehicle monitoring, event monitoring, activity monitoring, object monitoring, etc.), device control/management, tracking (e.g., device tracking, object tracking, hand tracking, eye gaze tracking, etc.), localization, object detection and/or recognition, object classification, pose estimation, shape estimation, scene mapping, scene detection and/or scene recognition, face detection and/or recognition, emotion detection and/or recognition, content anchoring, content rendering, content filtering, image processing, modeling, content generation, gesture detection and/or recognition, user interface generation, power management, event detection and/or recognition, and/or other operations based on data from one or more of the components of the user computing system 100, the vehicle computing system 210, and/or any other system or component.

In some examples, the one or more compute components 110 can implement one or more software engines and/or algorithms such as, for example, a feature extractor(s) (e.g., a scale-invariant feature transform (SIFT), speeded up robust features (SURF), oriented FAST and rotated BRIEF (ORB), etc.), a machine learning model(s), a computer vision algorithm(s), a neural network(s), a tracking algorithm(s), a localization algorithm(s), an object detection algorithm(s), a recognition algorithm(s), a mapping algorithm(s), an application(s) (e.g., an XR application, a messaging application, a social media network application, a web browser application, a productivity application, a gaming application, an entertainment application, a multi-media application, an authentication application, a photography application, a scanning application, a media playback application, a security application, an electronic commerce application, a content management application, an interface and/or windowing application, an assistant application, an automation application, an electronic mail application, a voice application, a camera application, a navigation application, a vehicle application, etc.), a computer vision algorithm, an image processing algorithm, a content filtering algorithm, and/or any other algorithm and/or component.

The image sensor 104A and/or the image sensor 104N can include any image and/or video sensor or capturing device, such as a digital camera sensor, a video camera sensor, a smartphone camera sensor, an image/video capture device on an electronic apparatus such as a television or computer, a camera, etc. In some cases, the image sensor 104A and/or the image sensor 104N can be part of a camera or computing device such as a digital camera, a video camera, an IP camera, a smartphone, a smart television, a game system, etc. Moreover, in some cases, the image sensor 104A and the image sensor 104N can include and/or implement a dual (or multiple) image sensor system or setup, such as rear and front sensor devices. In some examples, the image sensor 104A and the image sensor 104N can be part of a dual-camera or other multi-camera assembly (e.g., including two camera, three cameras, four cameras, or other number of cameras). In some cases, the image sensor 104A and/or the image sensor 104N can include an RF sensor, such as a radar sensor, a LIDAR sensor and/or an IR sensor configured to perform RF and/or IR imaging of the environment.

In some examples, each image sensor 104A and 104N can capture image data and generate frames based on the image data and/or provide the image data or frames to the one or more compute components 110 for processing. A frame can include a video frame of a video sequence or a still image. A frame can include a pixel array representing a scene. For example, a frame can be a red-green-blue (RGB) frame having red, green, and blue color components per pixel; a luma, chroma-red, chroma-blue (YCbCr) frame having a luma component and two chroma (color) components (chroma-red and chroma-blue) per pixel; or any other suitable type of color or monochrome picture.

The one or more wireless transceivers 128 can receive wireless signals (e.g., signal 140) via the one or more antennas 130, from one or more other devices and/or networks, such as other user devices, vehicles (e.g., vehicle 202 shown in FIG. 2), network devices (e.g., base stations such as eNBs and/or gNBs, WiFi devices (e.g., routers, access points, etc.), servers, switches, routers, gateways, firewalls, etc.), cloud networks, private networks, public networks, data centers, the Internet, satellites, connected or IoT devices, infrastructure devices/components, and/or the like. In some examples, the computing system 100 can include multiple antennae. The wireless signal 140 may be transmitted via a wireless network. The wireless network may be any wireless network, such as a cellular or telecommunications network (e.g., 3G, 4G, 5G, etc.), wireless local area network (e.g., a WiFi network), a Bluetooth™ network, and/or any other wireless network. In some examples, the one or more wireless transceivers 128 may include a radio frequency (RF) frontend. The RF frontend can include one or more components, such as one or more amplifiers, mixers (also referred to as a signal multiplier) for signal down conversion, frequency synthesizers (also referred to as an oscillator) that provides signals to the one or more mixers, baseband filters, analog-to-digital converters (ADCs), power amplifiers, RF ports (e.g., transmit (Tx) and/or receive (Rx) ports), phase shifters, IQ gain and phase compensators, up samplers, gain controls, digital-to-analog converters (DACs), beamformers, low pass filters, time delay filters, among other components. In some examples, the RF frontend can generally handle selection and conversion of the wireless signals 140 into a baseband or intermediate frequency and can convert the RF signals to the digital domain.

In some cases, the computing system 100 can include a coding-decoding device (or CODEC) configured to encode and/or decode data transmitted and/or received using the one or more wireless transceivers 128. In some cases, the computing system 100 can include an encryption-decryption device or component configured to encrypt and/or decrypt data (e.g., according to the advanced encryption standard (AES), the data encryption standard (DES), and/or any other standard) transmitted and/or received by the one or more wireless transceivers 128.

A SIM is a device (e.g., an integrated circuit) that can securely store an international mobile subscriber identity (IMSI) number and a related key (e.g., an encryption-decryption key) of a particular subscriber or user. The IMSI and key can be used to identify and authenticate the subscriber on a particular UE. In FIG. 1, each of the one or more SIMs 124 can securely store an IMSI number and related key assigned to the user of the mobile device 150. The IMSI and key can be used to identify and authenticate the subscriber when accessing a network provided by a network service provider or operator associated with the one or more SIMs 124.

A modem is a device that modulates one or more carrier wave signals to encode digital information for transmission, and demodulates signals to decode the transmitted information. The one or more modems 126 can modulate one or more signals to encode information for transmission using the one or more wireless transceivers 128. The one or more modems 126 can also demodulate signals received by the one or more wireless transceivers 128 in order to decode the transmitted information. In some examples, the one or more modems 126 can include a 4G (or LTE) modem, a 5G (or new radio (NR)) modem, a modem configured for vehicle-to-everything (V2X) communications, and/or other types of modems. The one or more modems 126 and the one or more wireless transceivers 128 can be used for communicating data for the one or more SIMs 124.

As noted above, the computing system 100 can include one or more sensor systems 102. In some examples, the one or more sensor systems 102 can include one or more image sensors such as image sensors 104A and 104N (collectively "image sensors 104" hereinafter), a location sensor 106 (e.g., an ultrasonic sensor, an infrasonic sensor, a SONAR sensor, an RF-based sensor system (e.g., WiFi, Bluetooth, etc.), a microphone, etc.), an inertial measurement unit (IMU) 108, and/or one or more other sensors. In some cases, the computing system 100 can optionally include one or more other/additional sensors or sensor systems such as, for example and without limitation, a RADAR sensor system, a LIDAR sensor system, an electromagnetic detection and ranging (EmDAR) sensor system, an infrared sensor system, a laser rangefinder system, a sound detection and ranging (SODAR) system, a touch sensor, a pressure sensor (e.g., a barometric air pressure sensor and/or any other pressure sensor), a gyroscope, an accelerometer, a magnetometer, and/or any other sensor. In some examples, the computing system 100 can include additional components such as, for example, a light-emitting diode (LED) device, a cache, a wireless network interface, etc. An example architecture and example hardware components that can be implemented by the computing system 100 are further described below with respect to FIG. 15.

The computing system 100 can include (and/or be in communication with) one or more non-transitory machine-readable storage media or storage devices (e.g., one or more memory devices 132), which can include, for example and without limitation, local and/or network accessible storage, a disk drive, a drive array, an optical storage device, a solid-state storage device such as a RAM and/or a ROM (e.g., which can be programmable and/or flash-updateable), and/or the like. Such storage devices may be configured to implement any appropriate data storage, including without limitation, various file systems, database structures, and/or the like.

In some examples, functions may be stored as one or more computer-program products (e.g., instructions or code) in memory device(s) 132 and executed by the compute components 110. The computing system 100 can also include software elements (e.g., located within the one or more memory devices 132), including, for example, an operating system, device drivers, executable libraries, and/or other code, such as one or more application programs, which may comprise computer programs implementing the functions provided by various embodiments, and/or may be designed to implement methods and/or configure systems, as described herein.

In some implementations, a user equipment (UE) can be configured for Dual SIM Dual Active (DSDA) functionality. For instance, the mobile device 150, the vehicle 202 shown in FIG. 2, and/or other UEs can be equipped with DSDA functionality. A UE with DSDA functionality can be equipped with at least two SIMs. In one illustrative example, a vehicle (e.g., vehicle 202 shown in FIG. 2) and user device (e.g., mobile device 150) with DSDA functionality can enable the vehicle and an occupant (e.g., driver, passenger, etc.) of the vehicle and the user device to choose independent network operator (or provider) subscriptions, with each operator subscription being associated with a particular SIM. For instance, the vehicle can use a first operator for wireless communication access and the user device can use a second operator for wireless communication access.

In some cases, DSDA functionality can support at least two active SIMs for a vehicle, including an OEM SIM and a user SIM, such as those described below with respect to the vehicle computing system 210 of FIG. 2. As noted below, the OEM SIM and/or the user SIM can be used along with one or more modems (e.g., the modem 228 shown in FIG. 2 and/or other modem of the communications system 222 shown in FIG. 2). In some implementations, the OEM SIM, the user SIM, and the modem(s) of the vehicle can be part of a telematic control unit (TCU) of the vehicle or can be part of a network access device (NAD) (also referred to in some cases as a network control unit or NCU) of the TCU (e.g., as part of the communications system 222 of FIG. 2). As described below, the OEM SIM can store information that provides access for performing wireless communications for vehicle-based operations (e.g., for eCall functions, for communicating with the vehicle manufacturer such as for software updates etc., among other operations). The OEM SIM supports various services for the vehicle, including eCall for making emergency calls. The user SIM can be used for performing wireless network access for a UE of a user in order to support a user data connection, such as for facilitating phone calls, messaging, infotainment related services, among others.

DSDA can allow the user SIM and a modem of the vehicle to be used for wireless network access (e.g., for a cellular connection) in place of a SIM and/or modem of a UE. For example, upon being brought into a communication range of the vehicle, a user device (e.g., a mobile device) can connect with the vehicle over an interface (e.g., over Bluetooth™, WiFI™, USB port, lightning port, and/or other wireless or wired interface). Once connected, a communication unit of the user device can transfer the wireless network access functionality from the user device to a communication unit of the vehicle. The communication unit of the vehicle can begin interacting with a base station to perform one or more wireless communication operations, such as facilitating a phone call, transmitting and/or receiving data (e.g., messaging, video, audio, etc.), among other operations. As noted above, a "communication unit" of a device (e.g., a vehicle, user device, other UE, roadside unit (RSU), etc.) can be a TCU, a NAD, a modem, a SIM, a transceiver (or individual receiver and/or transmitter), any combination thereof, and/or other system, device, or component configured to perform wireless communication operations. In one illustrative example, a user SIM (e.g., information stored on the SIM and/or the actual SIM card) of a user device (e.g., a mobile device) can be transferred to a TCU NAD of a vehicle, after which a modem of the vehicle can use the user SIM information to communicate with a wireless network operator for the user.

Figure 2:
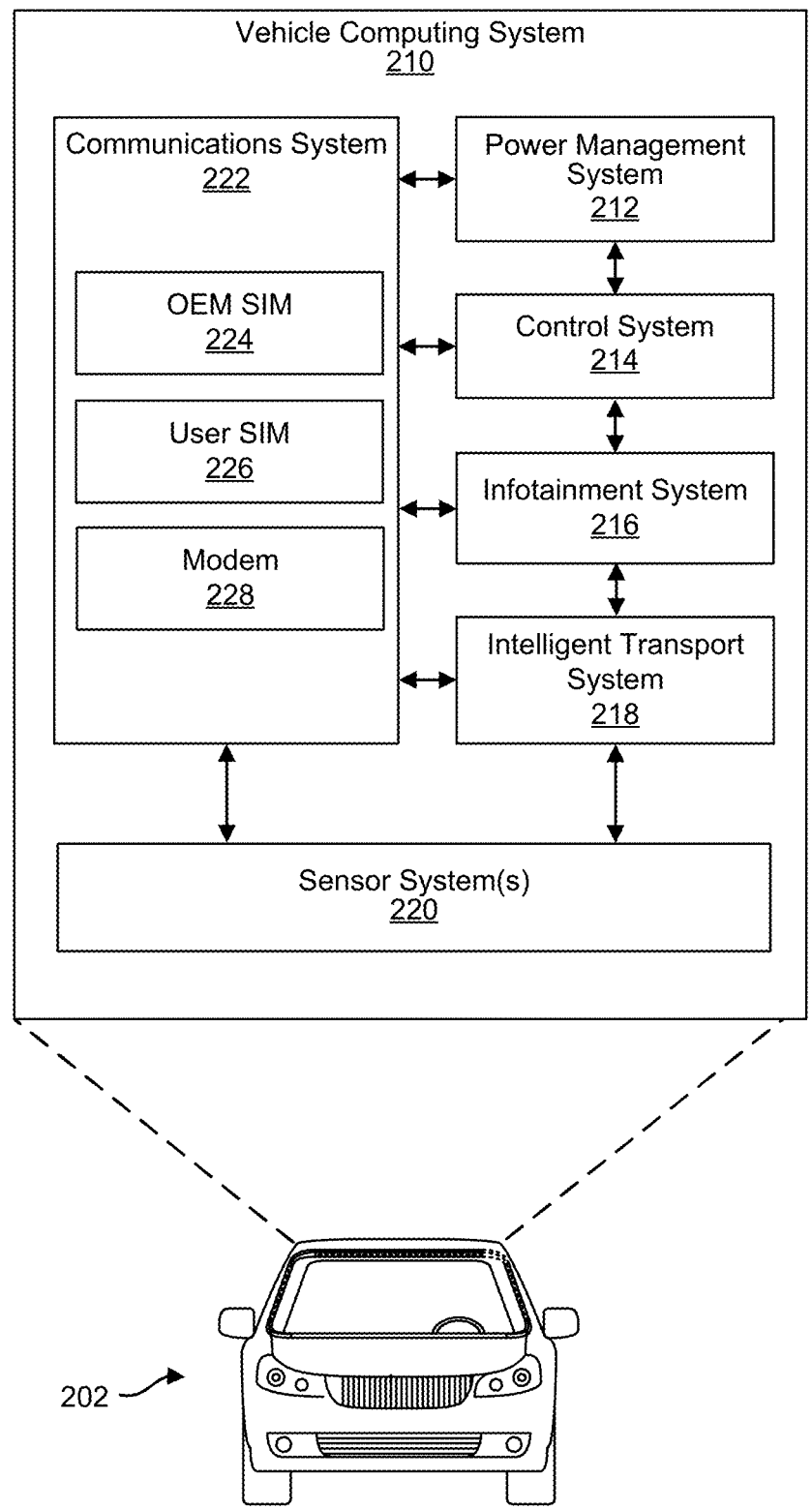
FIG. 2 is a block diagram illustrating an example computing system of a vehicle, in accordance with some examples of the present disclosure.

FIG. 2 is a block diagram illustrating an example of a vehicle computing system 210 of a vehicle 202. The vehicle 202 is an example of a UE that can communicate with a network (e.g., an eNB, a gNB, a positioning beacon, a location measurement unit, and/or other network entity) and/or with other UEs (e.g., mobile device 150) using V2X communications (e.g., over a PC5 interface or other device to device direct interface). As shown, the vehicle computing system 210 can include at least a power management system 212, a control system 214, an infotainment system 216, an intelligent transport system (ITS) 218, one or more sensor systems 220, and a communications system 222. In some cases, the vehicle computing system 210 can include or can be implemented using any type of processing device or system, such as one or more CPUs, DSPs, GPUs, ISPs, ASICs, FPGAs, application processors (APs), vision processing units (VPUs), neural processing units (NPUs), control voltage processors (CVPs), microcontrollers, dedicated hardware, any combination thereof, and/or other processing device or system.

The control system 214 can be configured to control one or more operations of the vehicle 202, the power management system 212, the computing system 210, the infotainment system 216, the ITS 218, and/or one or more other systems of the vehicle 202 (e.g., a braking system, a steering system, a safety system other than the ITS 218, a cabin system, and/or other system). In some examples, the control system 214 can include one or more electronic control units (ECUs). An ECU can control one or more of the electrical systems or subsystems in a vehicle. Examples of specific ECUs that can be included as part of the control system 214 include an engine control module (ECM), a powertrain control module (PCM), a transmission control module (TCM), a brake control module (BCM), a central control module (CCM), a central timing module (CTM), among others. In some cases, the control system 214 can receive sensor signals from the one or more sensor systems 220 and can communicate with other systems of the vehicle computing system 210 to operate the vehicle 202.

The vehicle computing system 210 also includes a power management system 212. In some implementations, the power management system 212 can include a power management integrated circuit (PMIC), a standby battery, and/or other components. In some cases, other systems of the vehicle computing system 210 can include one or more PMICs, batteries, and/or other components. The power management system 212 can perform power management functions for the vehicle 202, such as managing a power supply for the computing system 210 and/or other parts of the vehicle. For example, the power management system 212 can provide a stable power supply in view of power fluctuations, such as based on starting an engine of the vehicle. In another example, the power management system 212 can perform thermal monitoring operations, such as by checking ambient and/or transistor junction temperatures. In another example, the power management system 212 can perform certain functions based on detecting a certain temperature level, such as causing a cooling system (e.g., one or more fans, an air conditioning system, etc.) to cool certain components of the vehicle computing system 210 (e.g., the control system 214, such as one or more ECUs), shutting down certain functionalities of the vehicle computing system 210 (e.g., limiting the infotainment system 216, such as by shutting off one or more displays, disconnecting from a wireless network, etc.), among other functions.

The vehicle computing system 210 can include a communications system 222. The communications system 222 can include software and hardware components for transmitting signals to and receiving signals from a network (e.g., a gNB or other network entity) and/or from other UEs (e.g., to another vehicle or UE over a PC5 interface, WiFi interface, Bluetooth™ interface, and/or other wireless and/or wired interface). For example, the communications system 222 can be configured to transmit and receive information wirelessly over any suitable wireless network (e.g., a 3G network, 4G network, 5G network, WiFi network, Bluetooth™ network, and/or other network). The communications system 222 includes various components or devices used to perform the wireless communication functionalities, including an original equipment manufacturer (OEM) subscriber identity module (referred to as a SIM or SIM card) 224, a user SIM 226, and a modem 228. While the vehicle computing system 210 is shown as having two SIMs and one modem, the computing system 210 can have any number of SIMs (e.g., one SIM or more than two SIMs) and any number of modems (e.g., one modem, two modems, or more than two modems) in some implementations.

As previously explained, a SIM is a device (e.g., an integrated circuit) that can securely store an international mobile subscriber identity (IMSI) number and a related key (e.g., an encryption-decryption key) of a particular subscriber or user. The IMSI and key can be used to identify and authenticate the subscriber on a particular UE. The OEM SIM 224 can be used by the communications system 222 for establishing a wireless connection for vehicle-based operations, such as for conducting emergency-calling (eCall) functions, communicating with a communications system of the vehicle manufacturer (e.g., for software updates, etc.), among other operations. The OEM SIM 224 can be important for the communications system to support critical services, such as eCall for making emergency calls in the event of a car accident or other emergency. For instance, eCall can include a service that automatically dials an emergency number (e.g., "9-1-1" in the United States, "1-1-2" in Europe, etc.) in the event of a vehicle accident and communicates a location of the vehicle to the emergency services, such as a police department, fire department, etc.

The user SIM 226 can be used by the communications system 222 to perform wireless network access functions in order to support a user data connection (e.g., for conducting phone calls, messaging, Infotainment related services, among others). In some cases, a user device of a user can connect with the vehicle computing system 210 over an interface (e.g., over PC5, Bluetooth™, WiFI™, a universal serial bus (USB) port, and/or other wireless or wired interface). Once connected, the user device can transfer wireless network access functionality from the user device to communications system 222 the vehicle, in which case the user device can cease performance of the wireless network access functionality (e.g., during the period in which the communications system 222 is performing the wireless access functionality). The communications system 222 can begin interacting with a base station to perform one or more wireless communication operations, such as facilitating a phone call, transmitting and/or receiving data (e.g., messaging, video, audio, etc.), among other operations. In such cases, other components of the vehicle computing system 210 can be used to output data received by the communications system 222. For example, the infotainment system 216 (described below) can display video received by the communications system 222 on one or more displays and/or can output audio received by the communications system 222 using one or more speakers.

The modem 228 (and/or one or more other modems of the communications system 222) can be used for communication of data for the OEM SIM 224 and/or the user SIM 226. In some examples, the modem 228 can include a 4G (or LTE) modem and another modem (not shown) of the communications system 222 can include a 5G (or NR) modem. In some examples, the communications system 222 can include one or more Bluetooth™ modems (e.g., for Bluetooth™ Low Energy (BLE) or other type of Bluetooth communications), one or more WiFi™ modems (e.g., for dedicated short-range communications (DSRC) and/or other WiFi communications), wideband modems (e.g., an ultra-wideband (UWB) modem), any combination thereof, and/or other types of modems.

In some cases, the modem 228 (and/or one or more other modems of the communications system 222) can be used for performing V2X communications (e.g., with other vehicles for vehicle-to-vehicle (V2V) communications, with other devices for device-to-device (D2D) communications, with infrastructure systems for vehicle-to-infrastructure (V2I) communications, with pedestrian UEs for vehicle-to-pedestrian (V2P) communications, etc.). In some examples, the communications system 222 can include a V2X modem used for performing V2X communications (e.g., sidelink communications over a PC5 interface), in which case the V2X modem can be separate from one or more modems used for wireless network access functions (e.g., for network communications over a network or air interface (e.g., universal mobile telecommunications system (UMTS) interface or "Uu interface", etc.) and/or sidelink communications other than V2X communications).

In some examples, the communications system 222 can be or can include a telematics control unit (TCU). In some implementations, the TCU can include a network access device (NAD) (also referred to in some cases as a network control unit or NCU). In some cases, the NAD can include the modem 228, any other modem not shown in FIG. 2, the OEM SIM 224, the user SIM 226, and/or other components used for wireless communications. In some examples, the communications system 222 can include a Global Navigation Satellite System (GNSS). In some cases, the GNSS can be part of the one or more sensor systems 220, as described below. The GNSS can provide the ability for the vehicle computing system 210 to perform one or more location services, navigation services, and/or other services that can utilize GNSS functionality.

In some cases, the communications system 222 can include one or more wireless interfaces (e.g., including one or more transceivers and one or more baseband processors for each wireless interface) for transmitting and receiving wireless communications, one or more wired interfaces (e.g., a serial interface such as a universal serial bus (USB) input, a lightening connector, and/or other wired interface) for performing communications over one or more hardwired connections, and/or other components that can allow the vehicle 202 to communicate with a network and/or other UEs.

The vehicle computing system 210 can also include an infotainment system 216 that can control content and one or more output devices of the vehicle 202 that can be used to output the content. The infotainment system 216 can also be referred to as an in-vehicle infotainment (IVI) system or an in-car entertainment (ICE) system. The content can include navigation content, media content (e.g., video content, music or other audio content, and/or other media content), among other content. The one or more output devices can include one or more graphical user interfaces, one or more displays, one or more speakers, one or more extended reality devices (e.g., a VR, AR, and/or MR headset), one or more haptic feedback devices (e.g., one or more devices configured to vibrate a seat, steering wheel, and/or other part of the vehicle 202), and/or other output device.

In some examples, the computing system 210 can include the intelligent transport system (ITS) 218. In some examples, the ITS 218 can be used to implement V2X communications. For example, an ITS stack of the ITS 218 can generate V2X messages based on information from an application layer of the ITS. In some cases, the application layer can determine whether certain conditions have been met for generating messages for use by the ITS 218 and/or for generating messages that are to be sent to other vehicles (e.g., for V2V communications), to pedestrian UEs (e.g., for V2P communications), and/or to infrastructure systems (e.g., for V2I communications). In some cases, the communications system 222 and/or the ITS 218 can obtain car access network (CAN) information (e.g., from other components of the vehicle via a CAN bus). In some examples, the communications system 222 (e.g., a TCU NAD) can obtain the CAN information via the CAN bus and can send the CAN information to the ITS stack. The CAN information can include vehicle related information, such as a heading of the vehicle, speed of the vehicle, breaking information, among other information. The CAN information can be continuously or periodically (e.g., every 1 millisecond (ms), every 10 ms, or the like) provided to the ITS 218.

The conditions used to determine whether to generate messages can be determined using the CAN information based on safety-related applications and/or other applications, including applications related to road safety, traffic efficiency, infotainment, business, and/or other applications. In one illustrative example, ITS 218 can perform lane change assistance or negotiation. For instance, using the CAN information, the ITS 218 can determine that the vehicle 202 or a driver of the vehicle 202 is attempting to change lanes from a current lane to another lane such as an adjacent lane (e.g., based on a blinker being activated, based on the user veering or steering into an adjacent lane, etc.). Based on a determination that the vehicle 202 is attempting to change lanes, the ITS 218 can determine a lane-change condition has been met that is associated with a message to be sent to other vehicles that are nearby the vehicle in the adjacent lane. The ITS 218 can trigger the ITS stack to generate one or more messages for transmission to the other vehicles, which can be used to negotiate a lane change with the other vehicles. Other examples of applications include forward collision warning, automatic emergency breaking, lane departure warning, pedestrian avoidance or protection (e.g., when a pedestrian is detected near the vehicle 202, such as based on V2P communications with a UE of the user), traffic sign recognition, among others.

The ITS 218 can use any suitable protocol to generate messages (e.g., V2X messages). Examples of protocols that can be used by the ITS 218 include one or more Society of Automotive Engineering (SAE) standards, such as SAE J2735, SAE J2945, SAE J3161, and/or other standards.

A security layer of the ITS 218 can be used to securely sign messages from the ITS stack that are sent to and verified by other UEs configured for V2X communications, such as other vehicles, pedestrian UEs, and/or infrastructure systems. The security layer can verify messages received from such other UEs. In some implementations, the signing and verification processes can be based on a security context of the vehicle 202. In some examples, the security context may include one or more encryption-decryption algorithms, a public and/or private key used to generate a signature using an encryption-decryption algorithm, and/or other information. For example, each ITS message generated by the ITS stack can be signed by the security layer. The signature can be derived using a public key and an encryption-decryption algorithm. A vehicle, pedestrian UE, and/or infrastructure system receiving a signed message can verify the signature to ensure the message is from an authorized vehicle. In some examples, the one or more encryption-decryption algorithms can include one or more symmetric encryption algorithms (e.g., advanced encryption standard (AES), data encryption standard (DES), and/or other symmetric encryption algorithm), one or more asymmetric encryption algorithms using public and private keys (e.g., Rivest-Shamir-Adleman (RSA) and/or other asymmetric encryption algorithm), and/or other encryption-decryption algorithm.

In some examples, the ITS 218 can determine certain operations (e.g., V2X-based operations) to perform based on messages received from other UEs, such as mobile device 150.

The operations can include, for example and without limitation, safety-related operations, navigation operations, driving operations, and/or other operations, such as operations for road safety, traffic efficiency, navigation, infotainment, business, driving operations, and/or other applications. In some examples, the operations can include causing the vehicle 202 (e.g., the control system 214) to perform automatic functions, such as automatic braking, automatic steering (e.g., to maintain a heading in a particular lane), automatic lane change negotiation with other vehicles, automatic acceleration and/or deceleration, among other automatic functions. In one illustrative example, a message can be received by the communications system 222 from another UE such as another vehicle (e.g., over a PC5 interface) or mobile device. The message can indicate that the other vehicle is coming to a stop. In response to receiving the message, the ITS 218 can generate a message or instruction and send the message or instruction to the control system 214. The message or instruction can cause the control system 214 to automatically brake the vehicle 202 to stop the vehicle 202 (or reduce a speed of the vehicle 202) before making impact with the other vehicle (e.g., before crashing into/with the other vehicle).

In other illustrative examples, the operations can include triggering a presentation/display of a message alerting an occupant (e.g., the driver) of the vehicle 202 of a vehicle-related event, such as that another vehicle is in the lane next to the vehicle 202, a message alerting the occupant (e.g., the driver) to stop the vehicle 202, a message alerting the occupant (e.g., the driver) that a pedestrian is in an upcoming cross-walk (e.g., a cross-walk within a threshold proximity to the vehicle 202 and/or estimated to be nearing and/or approaching by the vehicle 202 within a certain period of time, etc.), a message alerting the occupant (e.g., the driver) that a toll booth is within a certain distance (e.g., within 1 mile or any other distance according to any measurement unit) of the vehicle 202, among others.

The computing system 210 can include one or more sensor systems 220 (e.g., a first sensor system through an Nth sensor system, where N is a value equal to or greater than 2). In some examples, the sensor system(s) 220 can include different types of sensor systems that can be arranged on or in different parts of the vehicle 202. In some examples, the sensor system(s) 220 can include one or more camera sensor systems, LIDAR sensor systems, RADAR sensor systems, EmDAR sensor systems, SONAR sensor systems, SODAR sensor systems, GNSS receiver systems (e.g., one or more GPS receiver systems), accelerometers, speed sensors, gyroscopes, magnetometers, pressure sensor systems, IMUs, infrared sensor systems, radio frequency (RF) sensor systems, laser rangefinder systems, ultrasonic sensor systems, infrasonic sensor systems, microphones, weight sensors, any combination thereof, and/or other sensor systems. It should be understood that any number of sensors or sensor systems can be included as part of the computing system 210 of the vehicle 202.

While the vehicle computing system 210 is shown to include certain components and/or systems, one of ordinary skill will appreciate that the vehicle computing system 210 can include more or fewer components than those shown in FIG. 2. For example, the vehicle computing system 210 can also include one or more input devices and one or more output devices (not shown). In some implementations, the vehicle computing system 210 can also include (e.g., as part of or separate from the control system 214, the infotainment system 216, the communications system 222, and/or the sensor system(s) 220) at least one processor and at least one memory having computer-executable instructions that are executed by the at least one processor. The at least one processor is in communication with and/or electrically connected to (referred to as being "coupled to" or "communicatively coupled") the at least one memory. The at least one processor can include, for example, one or more microcontrollers, one or more CPUs, one or more FPGAs, one or more ASICs, one or more GPUs, one or more NPUs, one or more DSPs, one or more ISPs, one or more VPUs, one or more application processors (Aps) (e.g., for running or executing one or more software applications), and/or other processors. The at least one memory can include, for example, read-only memory (ROM), random access memory (RAM) (e.g., static RAM (SRAM)), electrically erasable programmable read-only memory (EEPROM), flash memory, one or more buffers, one or more databases, and/or other memory. The computer-executable instructions stored in or on the at least memory can be executed to perform one or more of the functions or operations described herein.

Figure 3:
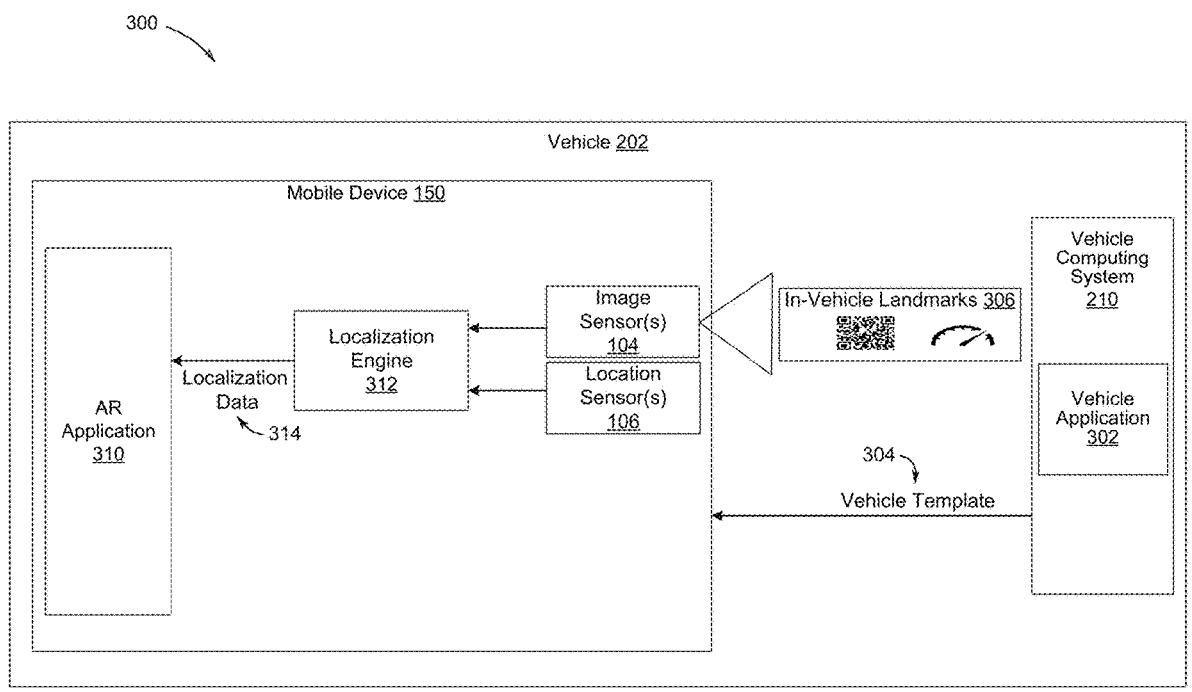
FIG. 3 is a diagram illustrating an example system process for in-vehicle localization, in accordance with some examples of the present disclosure.

FIG. 3 is a diagram illustrating an example system process 300 for in-vehicle localization. In this example, the mobile device 150 is located inside of the vehicle 202. The mobile device 150 can include an AR device worn by an occupant of the vehicle 202, such as a driver of the vehicle 202. The mobile device 150 can use the system process 300 to localize itself within the vehicle 202.

The mobile device 150 can use the in-vehicle localization to understand its pose relative to the vehicle 202, monitor the occupant of the vehicle 202 to detect any occupant impairments (e.g., distractions, intoxication, drowsiness, health emergencies/conditions, stress and/or heightened emotional states, inattention, etc.) of the occupant, monitor occupant activity/events, monitor/detect vehicle events/activity, mitigate vehicle events and/or control an operation of the vehicle 202, determine what (if any) content (e.g., virtual content, events, data, user interface, etc.) to render (and/or filter) for the occupant, etc. In some cases, the content rendered/filtered by the mobile device 150 can include data from (or based on data from) the vehicle 202 and/or the sensor systems 102 on the mobile device 150), such as sensor measurements, detected events, etc.

In some cases, the vehicle 202 can also render/filter content for the occupant. For example, the vehicle 202 can render content using a screen on/at the vehicle 202, a head-up display on/at the vehicle 202, a display on the dashboard of the vehicle 202, a projector device on/at the vehicle 202, and/or any other display device. In some examples, the content rendered by the vehicle 202 can include data from the vehicle 202, data from the sensor systems 102, and/or data from one or more other devices, such as a wearable device, a computing system of another vehicle, etc. In some cases, the vehicle 202 can receive the pose of the mobile device 150 relative to a coordinate system of the vehicle 202 and use the pose information to determine what content to render and/or filter, and/or determine where and/or when to render/filter such content.

As shown, a vehicle application 302 on the vehicle computing system 210 can send a vehicle template 304 to the mobile device 150. The mobile device 150 can use the vehicle template 304 to localize itself within the vehicle 202, as further described herein. The vehicle template 304 can specify and/or describe landmarks/markers 306 inside of the vehicle 202. The vehicle template 304 can also specify the coordinates of the landmarks/markers 306 relative to a coordinate system of the vehicle 202. The coordinates of the landmarks/markers 306 can include a position and/or orientation of the landmarks/markers 306 relative to the coordinate system of the vehicle 202. The landmarks/markers 306 can include any visual landmarks/markers that can be imaged and detected using one or more image sensors (e.g., image sensors 104) on the mobile device 150. For example, the landmarks/markers 306 can include one or more visual patterns inside of the vehicle 202, active illumination inside of the vehicle 202, elements or objects (movable and/or immovable elements) inside of the vehicle 202, devices, portions of an interior of the vehicle 202, and/or any other visual landmarks/markers. In some examples, one or more of the image sensors can be configured to perform RF and/or IR imaging. In these examples, the landmarks/markers 306 can include objects and/or patterns inside of the vehicle 202 that can be sensed in RF and/or IR.

In some examples, the landmarks/markers 306 can include one or more patterns or codes (e.g., quick response (QR) codes, barcodes, patterned designs such as checkerboard patterns, shapes, symbols, etc.) located in and/or affixed to an interior portion of (and/or object inside of) the vehicle 202, lights (e.g., light-emitting diodes (LEDs), lightbulbs, etc.) located in and/or affixed to an interior portion of (and/or object inside of) the vehicle 202, objects inside of the vehicle 202 (e.g., a door, window, seat, headrest, component in a dashboard/panel and/or center console of the vehicle 202 (e.g., instrumentation, radio/media system (and/or component thereof)), steering wheel, horn, signaling system, gear stick, cupholder, controls, etc.), movable and/or immovable elements inside of the vehicle 202 (e.g., a portion such as a corner of an interior portion of the vehicle 202 (e.g., of the windshield, a window, the dash, a door, a side panel, a rear window, etc.), a car seat, a steering wheel, etc).

The mobile device 150 can use one or more image sensors 104 to image the landmarks/markers 306. For example, the mobile device 150 can use the one or more image sensors 104 to capture one or more images depicting the landmarks/markers 306 in the vehicle 202. A localization engine 312 of the mobile device 150 can use the one or more images from the one or more image sensors 104 and the vehicle template 304 to localize itself within the vehicle 202. For example, the mobile device 150 can detect the landmarks/markers 306 depicted in the one or more images captured by the one or more image sensors 104. The localization engine 312 can use the vehicle template 304 to determine the coordinates (and orientations) of the landmarks/markers 306 relative to a coordinate system of the vehicle 202. The localization engine 312 can implement an algorithm, such as a transform, to convert the coordinates of the landmarks 306 relative to the coordinate system of the vehicle 202 to associated coordinates relative to a coordinate system of the mobile device 150. The localization engine 312 can use the coordinates of the landmarks/markers 306 relative to the vehicle 202 and the coordinates of the landmarks/markers 306 relative to the mobile device 150 to determine the pose of the mobile device 150 within the vehicle 202 (e.g., relative to the coordinate system of the vehicle 202).

In some examples, the localization engine 312 can use a tracked location (e.g., based on sensor data from one or more sensors on the mobile device 150) of the mobile device 150 relative to the coordinate system of the mobile device 150 to determine the pose of the mobile device 150 relative to the location and/or orientation of the landmarks/markers 306. The localization engine 312 can use the pose of the mobile device 150 relative to the location and/or orientation of the landmarks/markers 306 to determine the pose of the mobile device 150 relative to the coordinate system of the vehicle 202.

In some cases, the localization engine 312 can use data from the other sensors (e.g., location sensor(s) 106, IMU 108, etc.) to assist in determining the pose of the mobile device 150 within the vehicle 202. For example, the location sensor(s) 106 can use sensor data/signals (e.g., RF signals such as WiFi or Bluetooth, ultrasound signals, etc.) to determine a pose of the mobile device 150 relative to one or more objects in the vehicle 202. The location sensor(s) 106 can provide the determined pose of the mobile device 150 to the localization engine 312. The localization engine 312 can use such pose information as well as location and/or orientation information determined based on the landmarks/markers 306 as previously described, to localize the mobile device 150 within the vehicle 202.

Based on the in-vehicle localization, the localization engine 312 can generate localization data 314 indicating the pose of the mobile device 150 relative to the coordinate system of the vehicle 202. The localization engine 312 can provide the localization data 314 to an AR application 310 on the mobile device 150. In some examples, the AR application 310 can use the localization data 314 to render a user interface for the occupant of the vehicle 202 (e.g., for the user of the mobile device 150), determine what content (if any) to render for the occupant, determine what (if any) content to filter, monitor the occupant (e.g., for impairments, activity/events, etc.), mitigate events, and/or any other outputs and/or decisions as described herein. In some cases, the localization engine 312 and/or the mobile device 150 can provide the localization data 314 to the vehicle computing system 210, and the vehicle application 302 on the vehicle computing system 210 can use the localization data 314 to render a user interface and/or any other data described herein. In some cases, the vehicle application 302 can additionally or alternatively use event data, data about a state of the occupant (e.g., data indicating an impairment of the occupant), vehicle instrumentation data, and/or any other data to render a user interface and/or any other virtual content for the occupant.

In some cases, the mobile device 150 can determine the pose of the mobile device 150 using one or more images and with or without any other data and/or modalities. For example, the mobile device 150 can use one or more images of an interior portion of the vehicle 202 to determine a pose of the mobile device 150 relative to a coordinate system of the vehicle 202. The one or more images can depict one or more landmarks/markers in the interior portion of the vehicle 202. The mobile device 150 can use the one or more images to identify the position of the one or more landmarks/markers relative to itself, which the mobile device 150 can use to determine the pose of the mobile device 150 within the vehicle 202 (e.g., relative to the one or more landmarks/markers and/or relative to a coordinate system of the vehicle 202).

Figure 4A:
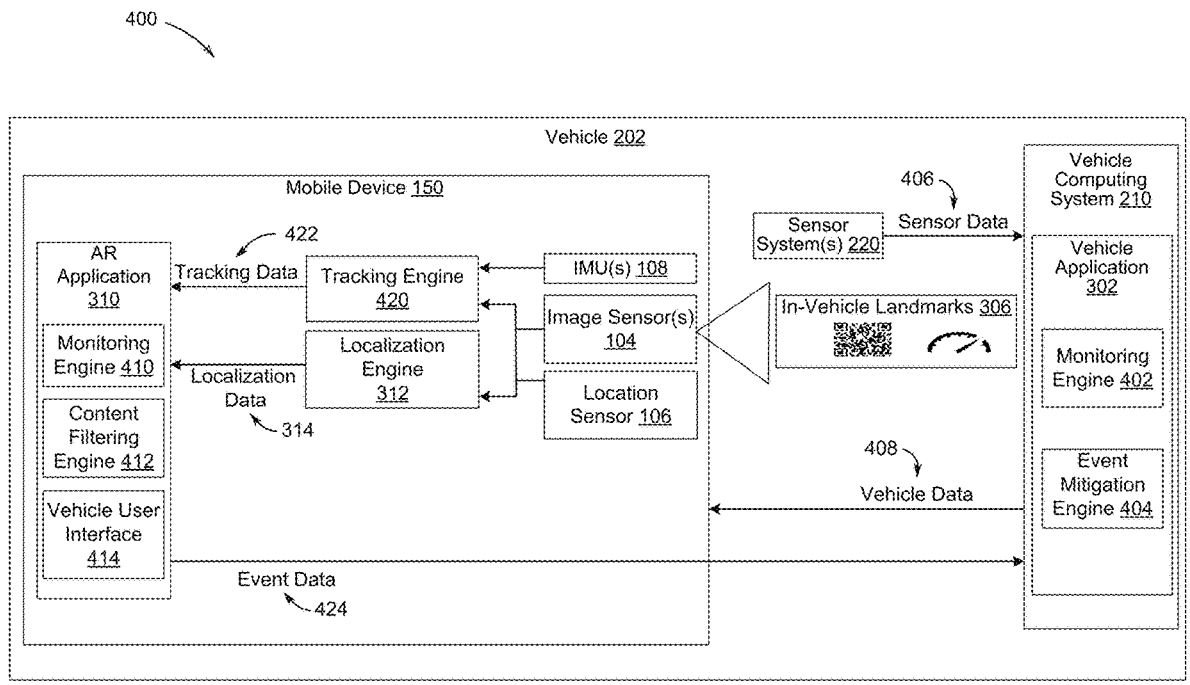
FIG. 4A and FIG. 4B are diagrams illustrating example system processes for augmented reality for vehicle occupant assistance, in accordance with some examples of the present disclosure.

FIG. 4A is a diagram illustrating an example system process 400 for augmented reality for vehicle occupant assistance. In this example, the vehicle 202 can include landmarks 306 as previously described. The vehicle computing system 210 can obtain sensor data 406 from the sensor systems 220 on the vehicle 202. The sensor data 406 can be used to generate at least a portion of vehicle data 408 provided to the mobile device 150, as further described herein. In some examples, the sensor data 406 can also be used by a vehicle monitoring engine 402 of the vehicle application 302 to monitor the vehicle 202 and/or an operation of the vehicle 202, and/or by an event mitigation engine 404 of the vehicle application 302 to perform event mitigation (e.g., assist a driver, correct an error and/or operation initiated/triggered by a driver, etc.). For example, the vehicle monitoring engine 402 can use the sensor data 406 to recognize and/or monitor status events and/or other events (e.g., imminent and/or occurring events) related to the vehicle 202 and its surroundings. As another example, the event mitigation engine 404 can use the sensor data 406 to perform driver event mitigation actions such as, for example and without limitation, preventing and/or implementing one or more vehicle functions, operations, and/or actions; generating warnings/alerts for a driver; correcting an error and/or operation initiated/triggered by a driver; implementing safeguards; activating one or more autonomous driving capabilities; etc. In some examples, the event mitigation engine 404 can perform driver event mitigation actions in response to reception of one or more driver monitoring events from the mobile device 150, as described herein.

The sensor data 406 can provide information about the status/state of the vehicle 202, the status of the vehicle surroundings, navigation information, driving/operating events, safety events, etc. For example, the sensor data 406 can include data indicating an operation of the vehicle 202 (e.g., speed, a heading/direction, acceleration/deceleration, etc.), a location of the vehicle 202, driving/operating statistics associated with the vehicle 202, timestamps associated with detected activity/events associated with the vehicle 202, any condition (e.g., object, lane marking, traffic signal, pedestrian, other vehicle, animal, road condition, traffic, weather, infrastructure condition, lighting, nearby obstruction, etc.) and/or activity/event external to the vehicle 202 (e.g., along a path of the vehicle 202, occurring outside of the vehicle 202, surrounding the vehicle 202, in an environment outside of the vehicle 202, within a proximity to the vehicle 202, etc.), navigation information, etc.

As another example, the sensor data 406 can (additionally or alternatively) include any condition and/or state of the vehicle 202 (e.g., a battery state-of-charge, an amount of fuel remaining, a warning and/or error, a failure or malfunction, etc.), any condition and/or state of one or more components of the vehicle 202 (e.g., a tire, a brake, a vehicle sensor, an engine, a door lock, a radio and/or sound system, a control and/or signaling system, the vehicle computing system 210, a blind spot information system, a driver monitoring system, a braking system, an autonomous driving component, a parking sensor, a driver-assistance system, a navigation system, an automotive heads-up display, a light sensor, a vehicle light, a vehicle communication system (e.g., V2V, V2I, V2X), etc.), any function/action implemented or being implemented by the vehicle 202 (e.g., autopilot, traction control, cruise control, collision avoidance, lane departure, lane centering, stability control, brake assist, traffic alert, lane-keeping, highway assist, parking, traffic sign recognition, blind spot monitoring, driver monitoring, intersection assistance, lane change assistance, intelligent speed adaptation, tire pressure monitoring, turning, acceleration/deceleration, signaling, etc.), any vehicle safety-related events (e.g., imminent collision, operating error, violation of one or more regulations (e.g., a speed limit, a seat belt regulation, lane crossing regulation, road safety regulations, etc.), an impact and/or shock event, etc.

In some cases, the sensor data 406 can include measurements associated with an occupant of the vehicle 202. For example, the sensor data 406 can include measurements from one or more weight sensors on one or more seats of the vehicle 202. The measurements from the one or more weight sensors can indicate that the occupant is in a particular seat of the vehicle 202. In some examples, the measurements of the one or more weight sensors can be used to aid in determining the position of the occupant and/or the mobile device 150, as further explained herein. For example, the measurements may indicate that the occupant is in a particular seat of the vehicle 202. The mobile device 150 can confirm the location/position of the occupant using one or more sensors, as further described herein.

The vehicle 202 can include landmarks 306 as previously described. The vehicle computing system 210 can provide vehicle data 408 to the mobile device 150. The vehicle data 408 can include a vehicle template (e.g., vehicle template 304). In some examples, the vehicle data 408 can also include any of the sensor data 406 and/or data generated based on the sensor data 406. In some cases, the data generated based on the sensor data 406 can include, for example and without limitation, a description of information in the sensor data 406 (e.g., a description of sensor measurements and/or as vehicle instrumentation), one or more determinations and/or predictions generated from the sensor data 406 (e.g., a determined and/or predicted event occurring in an environment of the vehicle 202 and/or estimated to impact an operation (and/or associated safety risk) of the vehicle 202, etc.), one or more outputs and/or inferences generated from the sensor data 406, statistics and/or metrics associated with the sensor data 406, events identified and/or described by the sensor data 406, status information associated with the vehicle 202 (e.g., a status/state of the vehicle 202), one or more attributes of the sensor data 406, etc.

For example, in some cases, the vehicle data 408 can include a vehicle template and at least one of event data included in and/or generated from the sensor data 406 and/or vehicle status information included in and/or generated from the sensor data 406. In some cases, the event data can include an indication of an event (e.g., an incoming/nearing event, an outgoing event, a stationary event, a moving event, a predicted event, etc.) in an environment surrounding and/or associated with the vehicle 202, such as one or more objects and/or subjects (e.g., a pedestrian, an animal, an infrastructure object, a building, a device, a bicycle, a motorcycle, traffic, a gate, a sign, etc.), obstacles (e.g., a pothole, a curb, a cone, a tree, road work, an accident, a road block, an electrical cable, roadside litter or objects, debris, water, ice, snow, etc.), an incident (e.g., a collision, a close or imminent encounter, a maneuver by another vehicle, roadside activity, an emergency or emergency vehicle, etc.), another vehicle, etc.

In some cases, the event can include one or more events based on a location/trajectory of the one or more events and/or the vehicle and/or a relevance to the operation/navigation of the vehicle 202. For example, the event can include an event detected in/along a path of the vehicle 202 and/or predicted to be in/along a path of the vehicle 202 within a threshold period of time or a threshold traveling distance by the vehicle 202, an event within a threshold proximity/distance to the vehicle 202 and/or the path of the vehicle 202, an event estimated to trigger/prompt a maneuver (e.g., acceleration, deceleration, turning, braking, lane centering, collision avoidance, stopping, signaling, etc.) by the vehicle 202 and/or a change in the operation (e.g., the policy) of the vehicle 202 (e.g., a route change, a change in or implementation of an autonomous driving function, a change in one or more driving parameters and/or threshold, etc.), etc.

The vehicle template in the vehicle data 408 can include an indication of the landmarks 306 in the vehicle 202 and the coordinates and/or orientation of the landmarks/markers 306 relative to a coordinate system of the vehicle 202 (e.g., relative to a coordinate system of the vehicle computing system 210 on the vehicle 202). For example, the vehicle template can include a description of a landmark/marker in the vehicle 202 and the coordinates and/or orientation of the landmark/marker relative to a coordinate system of the vehicle 202. The mobile device 150 can use the vehicle template in the vehicle data 408 (and any other portion of the vehicle data 408) to localize itself within the vehicle 202, as previously described. In some examples, the mobile device 150 can also use the vehicle data 408 to perform any of the functions described herein such as, for example, any of the AR, monitoring, rendering, control, communication, driver assistance, and/or mitigation functions described herein.

The localization engine 312 can generate localization data 314 that localizes the mobile device 150 within the vehicle 202. The localization engine 312 can provide the localization data 314 to the AR application 310 for use by the monitoring engine 410, the content filtering engine 412, and/or the vehicle user interface 414 as further described herein. The localization data 314 can include a pose of the mobile device 150 relative to a coordinate system of the vehicle 202. In some examples, the localization engine 312 can generate the localization data 314 based on the vehicle data 408 (e.g., based on the vehicle template in the vehicle data 408) and image data from one or more image sensors 104 of the mobile device 150.

For example, the localization engine 312 can obtain, from the one or more image sensors 104, one or more images of the landmarks/markers 306. The one or more images can depict one or more of the landmarks/markers 306. The localization engine 312 can detect the landmarks/markers 306 depicted in the one or more images. The localization engine 312 can use the vehicle template to determine the coordinates and/or orientation of any detected landmarks/markers referenced/described in the vehicle template. Based on the coordinates and/or orientation in the vehicle template, the localization engine 312 can determine the position and/or orientation of the detected landmarks/markers relative to the coordinate system of the vehicle 202.

In some cases, the localization engine 312 can also use tracking data 422 from the tracking engine 420 to determine the pose of the mobile device 150. In some examples, the tracking data 422 can include a pose of the mobile device 150 in physical space, as further described below. In some cases, the localization engine 312 can determine the pose of the mobile device 150 relative to the detected landmarks to determine the pose of the mobile device 150 relative to the coordinate system of the vehicle 202. For example, the localization engine 312 can use the one or more images depicting the landmarks/markers 306 to determine a position and/or orientation of the landmarks/markers 306 relative to the coordinate system of the mobile device 150. The localization engine 312 can use the position and/or orientation of the landmarks/markers 306 and a pose of the mobile device 150 indicated in the tracking data 422 from the tracking engine 420, to determine the pose of the mobile device 150 relative to the landmarks/markers 306. The localization engine 312 can use the relative pose of the mobile device 150 and the landmarks/markers 306 to determine the pose of the mobile device 150 relative to the coordinate system of the vehicle 202.

In some examples, to determine the pose of the mobile device 150 relative to the coordinate system of the vehicle 202, the localization engine 312 can transform (e.g., convert, translate, etc.) the coordinates of the detected landmarks relative to the coordinate system of the vehicle 202 to corresponding coordinates relative to a coordinate system of the mobile device 150. For example, in some cases, the localization engine 312 can determine the coordinates relative to the coordinate system of the mobile device 150 that correspond to the coordinates of the detected landmarks/markers relative to the coordinate system of the vehicle 202. The localization engine 312 can use the location (e.g., the coordinates) of the detected landmarks/markers relative to the coordinate system of the vehicle 202, and the location (e.g., coordinates) of the mobile device 150 relative to the coordinate system of the mobile device 150 relative to the location (e.g., coordinates) of the detected landmarks/markers relative to the coordinate system of the mobile device 150, to determine the pose of the mobile device 150 relative to the coordinate system of the vehicle 202.

In some cases, the localization engine 312 can also use data from the location sensor 106 to assist in generating the localization data 314, as previously described. For example, in some cases, the location sensor 106 can determine a pose of the mobile device 150 and/or one or more of the landmarks/markers 306 using one or more localization signals/algorithms such as, for example, RF-based localization/positioning, ultrasound-based localization/positioning, etc.

In some cases, the sensor data 406 can include measurements from one or more weight sensors on one or more seats of the vehicle 202. The measurements from the one or more weight sensors can indicate that an occupant holding or wearing the mobile device 150 is in a particular seat of the vehicle 202. This information can be used to confirm the location/position of the mobile device 150 determined by the mobile device 150 as previously explained.

The tracking engine 420 can obtain sensor data and use the sensor data to perform tracking operations. The tracking operations can track a pose (e.g., location, orientation, etc.) of the mobile device 150, the occupant (and/or one or more body parts of the occupant such as hands, eyes, fingers, a head pose, etc.) of the vehicle 202, etc. The sensor data can include image data from the one or more image sensors 104, position information (e.g., angular rate, linear acceleration, orientation; and/or changes in pitch, roll, and yaw) from the IMU 108, and/or data from one or more other sensors, such as the location sensor 106, of the mobile device 150 and/or the vehicle 202. In some examples, the tracking engine 420 can use data from the one or more image sensors 104, the IMU 108, and/or the location sensor 106 to perform positional tracking (e.g., six degrees of freedom (6DOF) positional tracking, etc.) of the mobile device 150 to determine the pose of the mobile device 150. The tracking engine 420 can generate tracking data 422 and provide the tracking data 422 to the AR application 310 for use by the monitoring engine 410, the content filtering engine 412, and/or the vehicle user interface 414. In some examples, the tracking data 422 can include a pose of the mobile device 150 relative to a coordinate system of the mobile device 150.

The tracking engine 420 can use one or more tracking algorithms, such as a Kalman filter, a hand tracking algorithm, a machine learning algorithm, a ray tracing algorithm, a gaze and/or eye tracking algorithm, a computer vision algorithm, a position tracking algorithm, etc., to track the mobile device 150 and/or one or more body parts (e.g., eyes, hands, fingers, head, etc.) of an occupant of the vehicle 202. The occupant can include a driver or passenger of the vehicle 202. The tracking engine 420 can provide tracking data 422 to the AR application 310. The tracking data 422 can include position and/or orientation information as further described herein.

In some cases, the tracking engine 420 can perform multiple tracking operations. For example, the tracking engine 420 can track the mobile device 150 and one or more body parts (e.g., a hand, eyes, a head, a finger, a posture, etc.) of the occupant of the vehicle 202. In some examples, the tracking engine 420 can track a hand(s) of the occupant of the vehicle 202. In some examples, the tracking engine 420 can track the eyes and/or an eye gaze of the occupant of the vehicle 202.

Figure 4B:
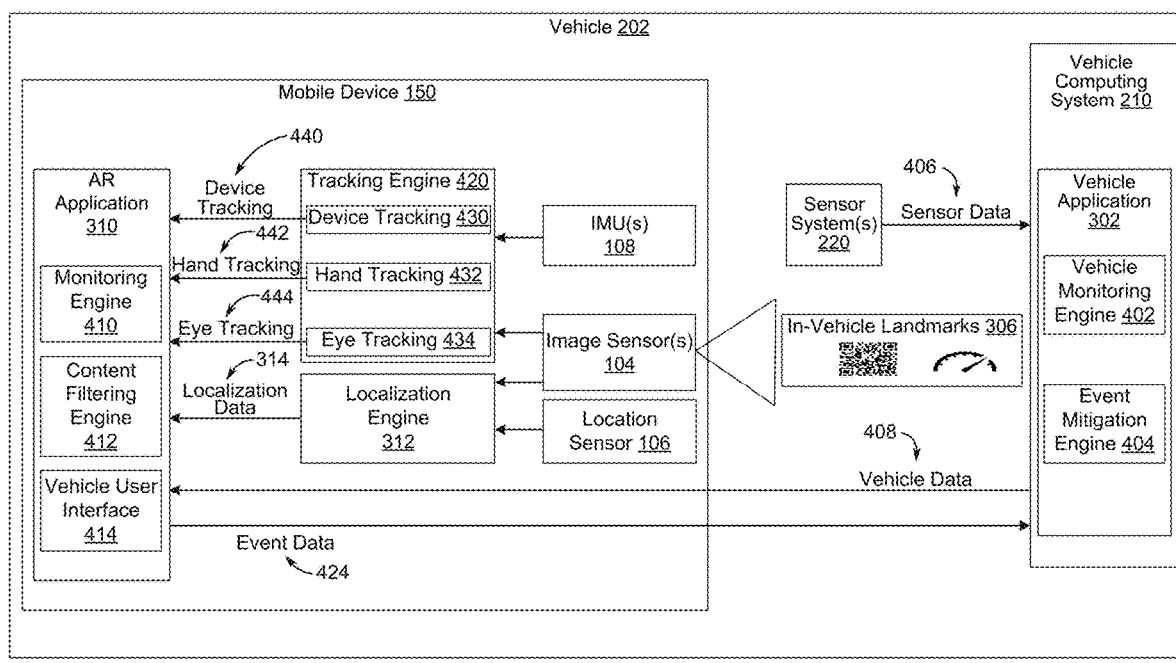

To illustrate, with reference to FIG. 4B, the tracking engine 420 can include a device tracking engine 430, a hand tracking engine 432, and/or an eye tracking engine 434. The device tracking engine 430 can track a position and/or orientation of the mobile device 150 as previously explained. The device tracking engine 430 can generate device tracking data 440 for the AR application 310. In some cases, the device tracking data 440 can include or represent at least a portion of the tracking data 422 shown in FIG. 4A.

The device tracking engine 430 can use one or more images from the one or more image sensors 104 and/or inertial sensor data from the IMU 108 to track the pose of the mobile device 150. In some cases, the device tracking engine 430 can (additionally or alternatively) use data from one or more additional sensors, such as the location sensor 106, to track the pose of the mobile device 150. For example, the location sensor 106 can obtain one or more RF signals and generate pose information associated with the mobile device 150 based on a round trip time (RTT) associated with the one or more RF signals, a time of arrival (TOA) associated with the one or more RF signals, a received signal strength indicator (RSSI) associated with the one or more RF signals, etc. The device tracking engine 430 can use the pose information from the location sensor 106 to track the pose of the mobile device 150.

The hand tracking engine 432 can track one or more hands of the occupant associated with the mobile device 150. The hand tracking engine 432 can generate hand tracking data 442 for the AR application 310. In some cases, the hand tracking data 442 can include or represent at least a portion of the tracking data 422 shown in FIG. 4A. The hand tracking engine 432 can use image data from the one or more image sensors 104 to track one or more hands of the occupant. The image data can include one or more images of the one or more hands of the occupant. The hand tracking engine 432 can detect the one or more hands in the one or more images and determine a pose of the one or more hands in physical space based on the one or more images depicting the one or more hands. In some cases, the hand tracking engine 432 can (additionally or alternatively) use data from one or more additional sensors, such as the location sensor 106, to track the pose of the one or more hands. For example, the location sensor 106 can obtain one or more RF signals and generate pose information associated with the one or more hands based on an RTT associated with the one or more RF signals, a TOA associated with the one or more RF signals, an RSSI associated with the one or more RF signals, etc. The hand tracking engine 432 can use the pose information from the location sensor 106 to track the one or more hands.

The hand tracking engine 432 can use one or more tracking algorithms, such as a hand tracking algorithm, a machine learning algorithm, a ray tracing algorithm, a computer vision algorithm, etc., to track the one or more hands. The hand tracking engine 432 can provide hand tracking data 442 to the AR application 310. The hand tracking data 442 can include a pose of the one or more hands in physical space.

The eye tracking engine 434 can use image data from the one or more image sensors 104 to track the eyes and/or an eye gaze of the occupant. The eye tracking engine 434 can generate eye tracking data 444 for the AR application 310. The eye tracking data 444 can include an eye gaze of the occupant determined at one or more times or time periods. In some cases, the eye tracking data 444 can include or represent at least a portion of the tracking data 422 shown in FIG. 4A.

The image data can include one or more images depicting the eyes of the occupant. The eye tracking engine 434 can detect the eyes in the one or more images and determine an eye gaze of the occupant based on the detected eyes in the one or more images. In some examples, the eye tracking engine 434 can use the one or more images and one or more algorithms, such as a ray tracing algorithm, a machine learning algorithm, a computer vision algorithm, etc., to detect an eye gaze of the occupant. The eye tracking engine 434 can provide the eye tracking data 444 to the AR application 310, as previously mentioned.

The AR application 310 can use the localization data (e.g., localization data 314) and the tracking data (e.g., tracking data 422, device tracking data 440, hand tracking data 442, and/or eye tracking data 444) to perform various functions such as, for example, occupant monitoring (e.g., via monitoring engine 410), virtual content filtering (e.g., via content filtering engine 412), content rendering (e.g., via vehicle user interface 414), a combination thereof, and/or other functions as described herein. For example, in some cases, the AR application 310 can implement a monitoring engine 410 configured to monitor events associated with the vehicle 202 and/or the occupant associated with the mobile device 150.

The AR application 310 can additionally or alternatively implement a content filtering engine 412 configured to use the localization data (e.g., localization data 314), the tracking data (e.g., tracking data 422, device tracking data 440, hand tracking data 442, and/or eye tracking data 444), occupant data from the monitoring engine 410, vehicle state data and/or event data from the vehicle data 408 and/or the monitoring engine 402 on the vehicle application 302, sensor data, and/or any other data, to filter/block virtual content from being rendered for the occupant and/or switch from a virtual content rendering to live content such as a live camera feed.

The AR application 310 can additionally or alternatively implement a vehicle user interface 414 configured to render data such as virtual content, live content (e.g., a camera feed, etc.) and/or user interface elements. The vehicle user interface 414 can render data based on the localization data (e.g., localization data 314), the tracking data (e.g., tracking data 422, device tracking data 440, hand tracking data 442, and/or eye tracking data 444), occupant data from the monitoring engine 410, vehicle and/or event data from the vehicle data 408 and/or the monitoring engine 402 on the vehicle application 302, sensor data, and/or any other data.

The monitoring engine 410 can monitor an occupant associated with the mobile device 150 and detect a state of the occupant. In some examples, the state of the occupant can include an eye gaze of the occupant, a pose of the occupant, an activity of the occupant, any impairments of the occupant, and/or any other information about the occupant. An impairment of the occupant can include any event, activity, distraction, state, attribute, behavior, and/or condition (e.g., cognitive, emotional or psychological, physiological, visual, audio, and/or situational events, conditions, attributes, activities, behaviors, distractions, and/or states) that can impact/influence the occupant's ability to safely operate (e.g., drive, control, manage, etc.) the vehicle 202. For example, an impairment can include anything that can negatively impact/influence the occupant's ability to (and/or associated response/reaction times) operate (e.g., drive, control, manage, etc.) the vehicle 202, detect/recognize any events/conditions encountered by the vehicle 202 during an operation of the vehicle 202, avoid and/or react to events/conditions encountered by the vehicle 202 during an operation of the vehicle 202, maintain a threshold amount of attention/focus on (and/or maintain an attention/focus for a threshold duration) operating the vehicle 202 (and/or any events/conditions associated with the vehicle 202, an operation of the vehicle 202, the environment/surroundings of the vehicle 202, etc.), and/or the like.

In some examples, an impairment can include a distraction (e.g., from an operation of the vehicle 202 and/or associated vehicle and/or relevant events), a state of drowsiness, a state of intoxication, a health emergency (e.g., a stroke, a heart attack, a seizure, a catatonic state, a loss of consciousness, etc.), a state of emotional or psychological stress, a heightened emotional state, loss of consciousness, incapacitation, a physiological state, an occupant context (e.g., an occupant position/posture, an occupant behavior, occupant movements, occupant activity, occupant engagement with the vehicle 202 and/or an environment of the occupant, occupant apparel such as apparel that restrains/restricts the occupant's freedom of movement or flexibility and/or reduces a reaction time of the occupant, a failure to wear a medical or safety device such as prescription glasses or a seat belt, items that reduce a visibility of the occupant such as sunglasses in poor visibility conditions or apparel that can block or partially block a visibility of the occupant, etc.) that may increase a safety risk and/or decrease an ability of the occupant to control the vehicle 202 and/or respond to driving- and/or vehicle-related events, a cognitive state of the occupant, high noise levels within the vehicle 202 (e.g., which may limit the occupant's ability to concentrate and/or hear relevant sounds), etc.

In some cases, an impairment can include a state of distraction of the occupant with respect to an operation of the vehicle 202 and/or an event associated with the vehicle 202, an intoxicated state of the occupant, a health condition of the occupant, a wakefulness state of the occupant, a detected emotional state of the occupant, an impaired position (of the occupant) to control the vehicle 202 (e.g., bending over while driving, leaning away from one or more controls of the vehicle 202, one or more hands occupied with one or more objects other than driving controls for controlling an operation/behavior of the vehicle 202, etc.), an impaired view (e.g., an obstruction of a view/visibility of the road and/or environment, an obstruction or reduction of light and/or visibility conditions, etc.), and/or any other impairments.

In some examples, the monitoring engine 410 can use the localization data (e.g., localization data 314), the tracking data (e.g., tracking data 422, device tracking data 440, hand tracking data 442, and/or eye tracking data 444), and/or any other event, state, and/or sensor data, such as the vehicle data 408 (or a portion thereof), to monitor an occupant (e.g., a driver, a passenger, etc.) and detect any impairment(s) of the occupant. For example, the monitoring engine 410 can determine any impairments of the occupant based on a context (related to, characterizing, and/or affecting the occupant's ability to safely operate the vehicle, e.g., state/status, operation, vehicle event, etc.) of the vehicle 202 (e.g., determined from the vehicle data 408 and/or the sensor data 406), a pose of the occupant (e.g., determined from the localization data (e.g., localization data 314), the tracking data (e.g., tracking data 422, device tracking data 440, hand tracking data 442, and/or eye tracking data 444), and/or data from the one or more image sensors 104, IMUs 108, the location sensor 106, and/or any other sensor and/or data), any virtual content rendered by the mobile device 150 for the occupant and/or any detected user interactions (e.g., occupant interactions) (e.g., inputs, eye gaze and/or focusing, gestures, etc.) with the rendered virtual content, eye tracking data, inertial sensor data, driving statistics, other sensor data, any combination thereof, and/or any other data.

For example, the context of the vehicle 202 may indicate a particular event (e.g., affecting a safe operation of the vehicle) has occurred or is expected to occur. The monitoring engine 410 may determine that, in order to control the vehicle 202 in response to the particular event and/or avoid safety issues and/or risks associated with the particular event, the occupant should be focused on and/or attentive to the event (and/or a particular area/direction associated with the event), should not be distracted by virtual content (or other content), should not be moving in certain ways, should not be engaged with certain virtual content, should be paying attention to the operation of the vehicle 202, should not be engaged in certain activities unrelated to certain operations of the vehicle 202, should be facing a certain direction, should be positioned in a certain way to allow the occupant to respond to the particular event (and/or operation of the vehicle 202), etc. Otherwise, the monitoring engine 410 can determine that the occupant is impaired based on the state/status of the vehicle 202 and/or the position, attention/focus, eye gaze, orientation, motion, content engagement, activity, etc., of the occupant.

In some cases, a context of the vehicle 202 can include a state/status of the vehicle 202, a vehicle event, etc. In some examples, an event associated with the vehicle 202 (e.g., a vehicle event) can include an obstruction within a path of the vehicle 202, an obstruction within a threshold proximity to the path of the vehicle 202, a different vehicle (e.g., a car, a bus, a motorcycle, an off-road vehicle, a bicycle, a train, a truck, etc.) within the path of the vehicle 202, a different vehicle within a threshold proximity to the vehicle 202, a traffic control (e.g., a traffic sign, a guide sign, a variable-message sign, a traffic cone, an arrow board, a construction barrel, a barricade, a traffic marker, a temporary raised island, a traffic light, etc.) associated with the path of the vehicle 202 (e.g., in/along the path of the vehicle 202, within a proximity to the path of the vehicle 202, etc.), a failure by the vehicle 202 to remain within a speed limit, a failure by the vehicle 202 to remain within a lane or lane marking, a failure by the vehicle 202 to remain within a road, a traffic event (e.g., an accident, a traffic re-routing, a stoppage, a traffic increase, a road closure, etc.), etc. In some examples, an obstruction can include a pedestrian, an animal, an object, another vehicle, a road condition, a tree, an obstacle, etc.

In some cases, a state of the vehicle 202 can include an operation and/or status of the vehicle 202 such as, for example and without limitation, an acceleration, a deceleration, a signaling (e.g., turn signal, etc.), a selected/active gear, a warning (e.g., engine warning, battery warning, fuel warning, tire warning, light warning, etc.), a maneuver (e.g., a turn, an exit/egress, an entrance/ingress, a u-turn, stopping/braking, etc.), a vehicle and/or vehicle component condition/status (e.g., a condition/status of an engine, a battery, one or more vehicle lights (e.g., a headlight, tail light, daytime running light, reverse light, emergency light, fog light, off-road light, signal light, brake light, etc.), a tire(s) (e.g., a tire pressure, a tire warning, a flat tire condition, etc.), a condition/status of one or more brakes or brake systems, a fuel status and/or fuel gauge reading, etc.), a failure or specific operation of one or more vehicle components/functions, a driving state, an autonomous state, a vehicle function state, etc.

In some cases, the monitoring engine 410 can determine a state of the occupant (e.g., an impairment of the occupant) based on various cues (e.g., visual and/or audio cues) and/or information about the occupant such as a state, characteristic, and/or condition of the occupant; any activity/motion of the occupant; a behavior of the occupant; an eye gaze of the occupant; etc. For example, the monitoring engine 410 can determine an impairment based on an eye gaze or a pattern of eye movements of the occupant (e.g., irregular eye movements, reduced responsiveness to stimuli, prolonged eye gazes, erratic eye gazes, focusing on certain locations or directions, etc.), characteristics of the eyes (e.g., redness, pupil size, glassy eyes, etc.), a reaction time(s) and/or characteristics (e.g., exaggerated reactions, lowered reaction times, etc.) by the occupant to one or more events, a facial expression of the occupant, a head pose and/or head movement of the occupant (e.g., hypnic jerks, head rolling, tilted or slumped head, etc.), a pose or posture of the occupant (e.g., slumped, crouched, body lean, irregular posture, etc.), a movement by the occupant (e.g., jerks, motor functions, exaggerated movements, etc.), hand gestures by the occupant, a driving posture of the occupant (e.g., in view of the current state/status/operation of the vehicle 202 and/or in general), a driving pattern of the occupant (e.g., a pattern of acceleration/deceleration, a pattern of lane changes, a pattern of braking, a pattern of signaling (or lack thereof), a pattern of vehicle maneuvers, a pattern of turning, etc).

In some cases, the monitoring engine 410 can determine an impairment of the occupant based on audio cues (in addition to visual cues or instead of visual cues). For example, in some cases, the monitoring engine 410 can obtain audio data from one or more sensors, such as microphones, of the mobile device 150 and/or the vehicle 202 and determine an impairment based on the audio data. To illustrate, the monitoring engine 410 can determine an impairment based on one or more speech characteristics (e.g., slurred speech, fast speech, etc.), a voice of the occupant (e.g., loudness or softness of voice, etc.), a content of recognized speech of the occupant, etc.

In some cases, the monitoring engine 410 can determine an impairment based on the state/status of the vehicle 202 and/or the content rendered by the mobile device 150. For example, if the state of the vehicle 202 indicates that the vehicle is traveling at a high speed, traveling in an environment with poor visibility, traveling in challenging conditions (e.g., wet or icy conditions, inclement weather conditions, sharp turns, heavily transited areas, high amounts of pedestrian and/or other traffic, etc.), performing a maneuver, etc., the monitoring engine 410 can determine an impairment of the occupant if the occupant is determined to be focused for a threshold period of time on virtual content rendered by the mobile device 150 or focused away from certain areas/locations (e.g., the road, the location of a vehicle event, etc.) for a threshold period of time, if the occupant is determined to be engaged in other activities (e.g., unrelated to the operation or safe operation (e.g., driving) of the vehicle 202), if the occupant is determined to be positioned more than a distance away from certain vehicle controls, if the occupant is determined to have a certain posture/position determined to decrease a driving safety or increase a driving risk (e.g., slouching, bending, turning, etc.), if the occupant is not wearing a seat belt, if the occupant is operating the vehicle 202 without vehicle lights (e.g., headlights, fog lights, tail lights, brake lights, etc.) in poor visibility conditions (e.g., at night, during inclement weather conditions, during heavy fog, etc.), etc. The monitoring engine 410 can determine the impairment based on the state/status of the vehicle 202 and/or the content rendered by the mobile device 150 in addition to or without any cues (visual and/or audio) about the occupant as previously described.

In some cases, the vehicle monitoring engine 402 of the vehicle application 302 can similarly determine any impairment of the occupant. The vehicle monitoring engine 402 can determine any impairments in addition to or in lieu of, any impairment information determined by the monitoring engine 410 of the AR application 310. For example, in some cases, the vehicle monitoring engine 402 can determine impairment information in combination with impairment information determined by the monitoring engine 410 of the AR application 310. As another example, in some cases, the vehicle monitoring engine 402 can determine impairment information separate from and/or without any impairment information determined by the monitoring engine 410 of the AR application 310. Moreover, the vehicle monitoring engine 402 can determine any impairments in addition to any vehicle data, such as data indicating a context of the vehicle 202, as further described below.

In some examples, the content filtering engine 412 can use the localization data (e.g., localization data 314), the tracking data (e.g., tracking data 422, device tracking data 440, hand tracking data 442, and/or eye tracking data 444), impairment information from the monitoring engine 410 (and/or the vehicle monitoring engine 402) and/or any other event, state, and/or sensor data, such as the vehicle data 408 (or a portion thereof), to determine/select content to filter/block and/or render for the occupant. For example, the content filtering engine 412 can use a pose of the mobile device 150 relative to a coordinate system of the vehicle 202 (e.g., of the vehicle computing system 210) and vehicle data indicating a context of the vehicle 202 (e.g., a state/status of the vehicle 202, a vehicle event/operation, etc.) to filter/block certain content that may distract the occupant from an operation of the vehicle 202 and/or a vehicle event and/or that may obstruct a view of the occupant to the vehicle event and/or a certain region outside of the vehicle 202 that the content filtering engine 412 determines should remain visible to the occupant. In some cases, instead of or in addition to filtering/blocking content, the content filtering engine 412 can replace virtual content rendered by the mobile device 150 with live content (e.g., a live camera feed) that may not obstruct a view of the occupant to a vehicle event or an environment outside of the vehicle 202. As another example, the content filtering engine 412 can use the pose of the mobile device 150 and information about the state of the vehicle 202 to render virtual content that draws the occupant's attention in a certain direction and/or to a certain location, such as the direction/location of a particular event.

In some cases, the content filtering engine 412 can use the pose of the mobile device 150 relative to the coordinate system of the vehicle 202 to correlate information from and/or associated with the vehicle 202 with a pose of the mobile device 150. For example, the state/status of the vehicle 202 may indicate a location of a vehicle event reported by the vehicle computing system 210. The location of the vehicle event may be relative to the coordinate system of the vehicle. Thus, the pose of the mobile device 150 can be correlated to the location of the vehicle event as both are known relative to the coordinate system of the vehicle. The content filtering engine 412 can use the pose of the mobile device 150 relative to the coordinate system of the vehicle 202 to determine whether any virtual content rendered for the occupant would obstruct the occupant's view to an event reported by the vehicle 202 relative to a coordinate system of the vehicle 202. If the content filtering engine 412 determines to block content at a specific location relative to the coordinate system of the vehicle 202, the content filtering engine 412 can use the pose of the mobile device 150 relative to the coordinate system of the vehicle 202 to filter/block any content from being rendered at the specific location.

In some examples, the content filtering engine 412 can filter any virtual content distracting the occupant or determined to distract the occupant. For example, the content filtering engine 412 can determine that video game content (or any other content) can distract the occupant and filter any video game content to prevent such content from being rendered for the occupant while operating the vehicle 202. In other examples, the content filtering engine 412 can filter any virtual content determined to block/obstruct a view/visibility of the occupant to a particular event, such as an obstruction along a path (or within a proximity to a path) of the vehicle 202, a traffic event, or any vehicle event described herein. For example, the content filtering engine 412 can determine that a view of the occupant to a vehicle event identified in the vehicle data 408 would be obstructed by virtual content based on the pose of the mobile device 150 relative to the coordinate system of the vehicle 202 and the location of the vehicle event relative to the coordinate system of the vehicle 202 (e.g., which can be indicated in the vehicle data 408). The content filtering engine 412 can then filter/block such virtual content to prevent the view of the occupant to the vehicle event from being obstructed and/or may switch from rendering the virtual content to providing a live feed. In some examples, the live feed may depict the vehicle event or may not obstruct the vehicle event.

The vehicle user interface 414 can render content and/or user interface elements for the occupant. In some examples, the vehicle user interface 414 can render or generate content and/or user interface elements based on a state/status of the vehicle 202. In some examples, the vehicle user interface 414 can use impairment information to determine whether to render content and/or what content to render for the occupant. For example, if the impairment information from the monitoring engine 410 indicates that the occupant is distracted, the vehicle user interface 414 can use such information to stop rendering content that may distract (or continue to distract) the occupant or to render content configured to draw the occupant's attention to a specific location and/or action/operation (and away from a different location and/or action/operation causing the occupant's distraction).

The vehicle user interface 414 can use the pose of the mobile device 150 relative to the coordinate system of the vehicle 202 to determine where (or if) to render content for the occupant. For example, to render content at a specific location to draw the occupant's attention to something relative to the coordinate system of the vehicle 202, the vehicle user interface 414 can use the pose of the mobile device 150 relative to the coordinate system of the vehicle 202 to render the content at that specific location. As another example, if the vehicle computing system 210 reports certain data associated with a specific location relative to the coordinate system of the vehicle 202, the vehicle user interface 414 can use the pose of the mobile device 150 relative to the coordinate system of the vehicle to render the data at that specific location relative to the coordinate system of the vehicle 202 or to render the data at a different location that is determined relative to that specific location relative to the coordinate system of the vehicle 202.

In some examples, the vehicle user interface 414 can use the pose of the mobile device 150 relative to the coordinate system of the vehicle 202 to determine where to render content for the occupant. For example, the vehicle user interface 414 can render virtual content (e.g., an arrow, a bounding box, an image, a pulsing light, etc.) in a specific location associated with a vehicle event to draw the occupant's attention to the vehicle event. As another example, the vehicle user interface 414 can render virtual content in a different location than a location of a vehicle event to prevent the virtual content from obstructing a view of the occupant to the vehicle event. In some examples, the vehicle user interface 414 can select the specific content to render for the occupant based on the state of the occupant and/or the context of the vehicle 202. For example, to avoid obstructing a view of the occupant to a particular event, the vehicle user interface 414 may render live content (e.g., a live camera feed) rather than virtual content. As another example, to avoid distracting the occupant, the vehicle user interface 414 may render virtual content rather than live content. To illustrate, if the context of the vehicle 202 indicates that another vehicle is broken down on the side of the road or pulled over by the police, the vehicle user interface 414 may render virtual content (or no content) rather than live content to prevent rubbernecking by the occupant. Alternatively, the content filtering engine 412 may filter out live content to prevent the rubbernecking, and the vehicle user interface 414 may instead render virtual content or no content at all. In some cases, the live content can include a live feed from the one or more image sensors 104 on the mobile device 150 and/or one or more image sensors of the vehicle 202.

In some cases, the AR application 310 can generate event data 424. The AR application 310 can also send the event data 424 to the vehicle computing system 210. In some cases, the AR application 310 can generate the event data 424 based on the localization data (e.g., localization data 314); the tracking data (e.g., tracking data 422, device tracking data 440, hand tracking data 442, and/or eye tracking data 444); any outputs and/or data from the monitoring engine 410, the content filtering engine 412, and/or the vehicle user interface 414; data from any sensors of the mobile device 150 (e.g., image sensors 104, location sensor 106, IMU 108, etc.); application data; user inputs; and/or any other data. In some cases, the event data 424 can include the localization data (e.g., localization data 314); the tracking data (e.g., tracking data 422, device tracking data 440, hand tracking data 442, and/or eye tracking data 444); any outputs and/or data from the monitoring engine 410, the content filtering engine 412, and/or the vehicle user interface 414; data from any sensors of the mobile device 150 (e.g., image sensors 104, location sensor 106, IMU 108, etc.); application data; user inputs; and/or any other data. In some cases, the event data 424 can additionally or alternatively include events generated from, and/or descriptions of, the localization data (e.g., localization data 314); the tracking data (e.g., tracking data 422, device tracking data 440, hand tracking data 442, and/or eye tracking data 444); any outputs and/or data from the monitoring engine 410, the content filtering engine 412, and/or the vehicle user interface 414; data from any sensors of the mobile device 150 (e.g., image sensors 104, location sensor 106, IMU 108, etc.); application data; user inputs; and/or any other data.

In some examples, the event data 424 can include, indicate, and/or describe a state of the occupant determined by the monitoring engine 410 as described above, content from the AR application 310, any combination thereof, and/or any other occupant and/or device information. In some examples, the state of the occupant can include an impairment(s) of the occupant determined by the monitoring engine 410. In some cases, the state of the occupant can additionally or alternatively include a pose of the occupant (e.g., a location, an orientation, a posture, etc.), any motion of the occupant, any activity by the occupant, an eye gaze of the occupant, a head pose of the occupant, any information about the occupant, and/or any other information indicative of an attention/focus of the occupant, activity of the occupant, movement of the occupant, visibility or field-of-view (FOV) of the occupant, behavior of the occupant, position (e.g., location, orientation, posture, etc.) of the occupant, reach (e.g., a reach to one or more vehicle controls) of the occupant, engagement of the occupant, and/or ability (and/or likelihood) of the occupant to control an operation(s) of the vehicle 202 and/or react to events associated with the vehicle 202.

As previously noted, the AR application 310 can send the event data 424 to the vehicle 202. For example, the AR application 310 can send the event data 424 to the vehicle computing system 210. In some cases, the vehicle computing system 210 can receive the event data 424 and provide the event data 424 to the vehicle application 302 for processing/analysis. In some cases, the vehicle application 302 can control a behavior, operation, function, and/or state of the vehicle 202 based on the event data 424 and/or the sensor data 406.

For example, in some cases, the event mitigation engine 404 of the vehicle application 302 can control (e.g., modify, implement, enable, disable, manage, etc.) a behavior, operation, function, and/or state of the vehicle 202 based on the event data 424 and/or the sensor data 406. In some examples, the event mitigation engine 404 can control and/or engage one or more vehicle functions, vehicle systems, autonomous capabilities, etc. For example, the event mitigation engine 404 can control and/or engage an autopilot function, a traction control function, a cruise control function, a collision avoidance function, a lane departure function, a lane centering function, a brake assist function, a lane-keeping function, a highway assist function, a lane change assistance function, a speed adaptation function, a signaling function, an intersection assistance function, a blind spot monitoring system, a driver monitoring system (e.g., monitoring engine 402 and/or any driver monitoring system), a braking system, an autonomous driving control system, a driver assistance system, a navigation system, a steering control system, a vehicular communication system, an automotive heads-up display, and/or any other vehicle system, function, and/or capability.

In some cases, the event mitigation engine 404 can control the vehicle 202 based on the event data 424 to mitigate any events and/or risks resulting from a state of the occupant and/or other information about the occupant included in the event data 424. In some examples, the event mitigation engine 404 can activate one or more driver-assistance functions, such as functions perform by one or more advance driver-assistance systems (ADAS), of the vehicle and/or increase a policy/level of autonomous driving of the vehicle based on the event data 424. To illustrate, if the event data 424 indicates that the occupant of the vehicle 202 is impaired (e.g., distracted, intoxicated, etc.), the event mitigation engine 404 can engage an autonomous capability of the vehicle 202 and/or modify an autonomous driving policy/level of the vehicle 202 to take at least partial control of the operation of the vehicle 202 while the occupant is impaired. As another example, if the event data 424 indicates that the occupant of the vehicle 202 is not paying attention to a nearby obstruction identified in the sensor data 406 or is unable to see the nearby obstruction (e.g., because the eye gaze of the occupant is in a different direction, because the view of the occupant is obstructed, because of poor visibility conditions, etc.), the event mitigation engine 404 can engage an autonomous capability of the vehicle 202 and/or modify an autonomous driving policy/level of the vehicle 202 to take at least partial control of the operation of the vehicle 202 until at least the obstruction is avoided or no longer a potential issue.

In some examples, the event mitigation engine 404 can notify/warn other external devices of any detected impairments of the occupant. For example, the event mitigation engine 404 can notify other vehicles, one or more remote computing devices associated with other users (e.g., a pedestrian, an occupant of another vehicle, a traffic guard/controller, etc.), vehicle infrastructure (e.g., a traffic light, a traffic camera, a streetlight, a signage, a parking meter, a lane marker, etc.), one or more emergency response systems and/or personnel, etc.

The monitoring engine 402 of the vehicle application 302 can use the sensor data 406 to monitor and/or detect a context of the vehicle 202 (related to, characterizing, and/or affecting the occupant's ability to (safely) operate the vehicle). As previously explained, in some examples, the context of the vehicle 202 can include a state (e.g., a status, an operation, a behavior, a trajectory, a condition, a configuration, an operating metric, a circumstance, a vehicle parameter, a function, etc.) of the vehicle 202, a vehicle event, etc. For example, the context of the vehicle 202 can indicate a particular vehicle event (affecting a safe operation of the vehicle, e.g., a particular activity, condition, incident, circumstance, operation, etc.) has occurred or is expected to occur. As another example, the context of the vehicle 202 can indicate an operation, behavior, and/or status of the vehicle 202. In some examples, the monitoring engine 402 can use the sensor data 406 to determine any aspects of a context of the vehicle 202 such as, for example, a state of the vehicle 202, a vehicle event, etc.

For example, the monitoring engine 402 can determine a context of the vehicle 202 by detecting, recognizing, and/or localizing one or more items (e.g., objects, events, people, animals, roads, vehicles, scenes, activities, traffic controls, structures, obstacles, devices, gestures, etc.) depicted in on one or more images (e.g., one or more images of a scene and/or portion of an environment outside of the vehicle 202 that are captured by one or more image sensors of the sensor systems 220) in the sensor data 406, determining inertial sensor data from the sensor data 406 that includes one or more motion measurements (e.g., velocity, angular rate, orientation, heading, acceleration, deceleration, etc.), determining location information (e.g., from one or more location devices such as a global positioning system (GPS) receiver or a global navigation satellite system (GNSS) receiver) in the sensor data 406, and/or determining additional location information (e.g., from one or more sensors such as, for example, a RADAR, a LIDAR, an image sensor, an RF-based positioning system, etc.) in the sensor data 406 that indicates/describes a location/position of one or more items (e.g., objects, events, people, animals, roads, trees, vehicles, scenes, traffic controls, activities, gestures, devices, structures, obstacles, etc.) relative to the vehicle 202 and/or proximity/distance of the one or more items to the vehicle 202, etc.

In some cases, the monitoring engine 402 can also use the event data 424 from the AR application 310 of the mobile device 150 to monitor and/or detect a context of the vehicle 202. For example, the monitoring engine 402 can account for a state of the occupant (e.g., an impairment, an eye gaze, a position, an activity, etc.) indicated in the event data 424, when determining the context of the vehicle 202.

Figure 5:
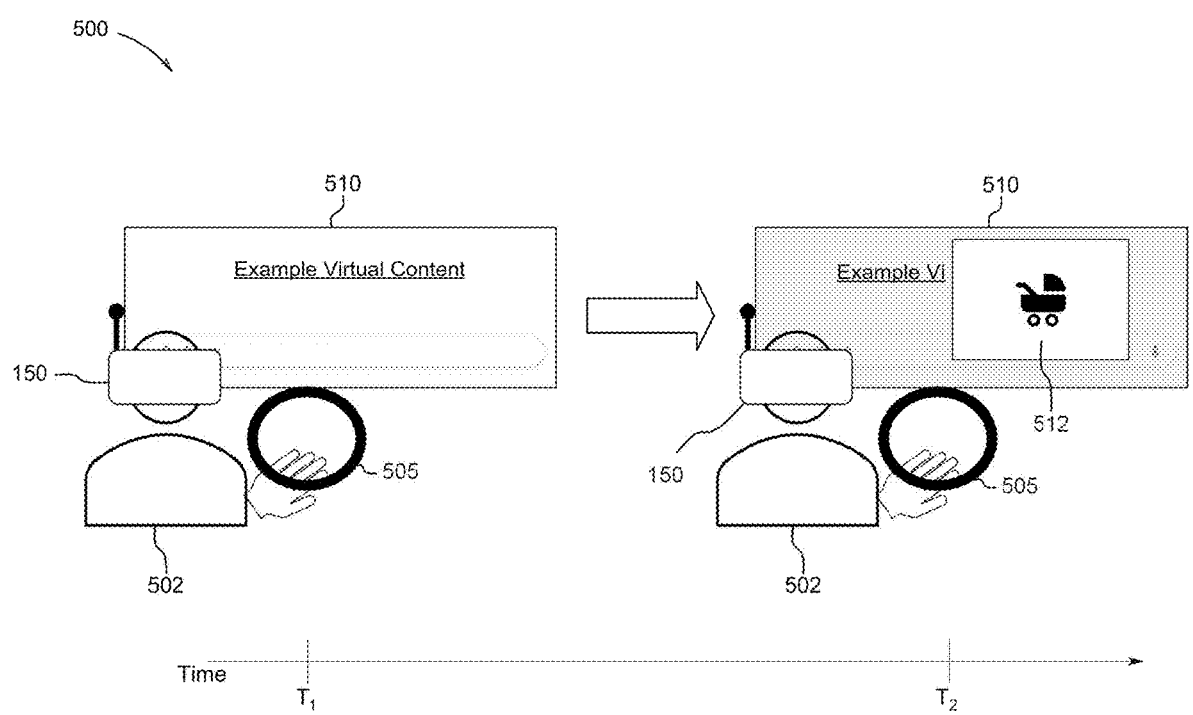
FIG. 5 is a diagram illustrating an example use case for modulating virtual content rendered for an occupant of a vehicle, in accordance with some examples of the present disclosure.

FIG. 5 is a diagram illustrating an example use case 500 for modulating virtual content rendered for an occupant 502 of a vehicle (e.g., vehicle 202). As previously explained, the AR application 310 can modulate/modify (e.g., via the content filtering engine 412 and/or the vehicle user interface 414) virtual content rendered by the mobile device 150. The AR application 310 can modulate (e.g., via the content filtering engine 412 and/or the vehicle user interface 414) virtual content based on the state of the occupant determined by the monitoring engine 410 of the AR application 310 and/or a context of the vehicle 202 identified in the vehicle data 408 and/or determined by the monitoring engine 402 of the vehicle application 302.

In some examples, the AR application 310 can modulate virtual content by disabling, dimming, or adjusting a characteristic(s) (e.g., a size, a brightness, a transparency, a location, an orientation, etc.) of the virtual content. In some cases, the AR application 310 can modulate all virtual content for a period of time, all virtual content during a particular context of the vehicle 202, all virtual content during a state of the occupant, all virtual content except a subset of virtual content marked as excepted or needed (e.g., HUD content, vehicle instrumentation content, navigation content, emergency alerts, etc.), any portion of virtual content on which the occupant is focused, any virtual content that is obscuring a vehicle event, etc.

For example, the AR application 310 can modulate virtual content by filtering/blocking (e.g., via the content filtering engine 412) one or more virtual content items (or all virtual content) rendered by the mobile device 150. As another example, the AR application 310 can modulate virtual content by controlling (e.g., via the vehicle user interface 414) what virtual content is presented, when the virtual content is presented, where the virtual content is presented, one or more characteristics (e.g., a transparency, a size, a brightness, a location, an orientation, etc.) of the virtual content presented, etc. In some examples, AR application 310 can filter/block (e.g., via the content filtering engine 412) virtual content based on the state of the occupant determined by the monitoring engine 410 of the AR application 310 and/or a context of the vehicle 202 identified in the vehicle data 408 and/or determined by the monitoring engine 402 of the vehicle application 302. In some examples, the AR application 310 can modulate (e.g., via the vehicle user interface 414) virtual content presented by the mobile device 150 based on the state of the occupant determined by the monitoring engine 410 and/or a context of the vehicle 202 identified in the vehicle data 408 and/or determined by the monitoring engine 402.

In the example use case 500 shown in FIG. 5, the occupant 502 of the vehicle 202 is wearing the mobile device 150, such as an HMD or smart glasses, while using a steering wheel 505 of the vehicle 202 to drive the vehicle 202. At time $T_1$, the mobile device 150 is rendering virtual content 510 while the occupant 502 is driving the vehicle 202. The mobile device 150 then determines (e.g., based on vehicle data 408 or a notification from the monitoring engine 402 of the vehicle application 302) that an event 512 that requires the attention and/or interaction of the occupant 502 is occurring or is imminent (e.g., will occur within a threshold period of time and/or within a threshold amount of traveling distance by the vehicle 202). In some cases, the mobile device 150 can determine the location of the event 512 (e.g., based on vehicle data 408 or a notification from the monitoring engine 402 of the vehicle application 302). In this example, the location of the event 512 is a location outside of the vehicle 202, and the event 512 is a stroller crossing a path of the vehicle 202. The event 512 here is merely one illustrative example provided for explanation purposes. Accordingly, other examples may include other events and/or types of events. In some examples, events can be categorized as requiring the attention and/or interaction of the occupant 502 by the monitoring engine 402 of the vehicle application 302 and/or the vehicle user interface 414, e.g., via a machine learning classifier trained on positive and negative examples.

The location of the virtual content 510 relative to a coordinate system of the mobile device 150 is associated with the location of the event 512 relative to the coordinate system of the vehicle 202. In the present example, the virtual content 510 is located within/along a line-of-sight from the location of the mobile device 150 to the location of the event 512. Thus, the line-of-sight from the mobile device 150 and/or a view/visibility of the event 512 from the mobile device 150 is/are blocked/obstructed by the virtual content 510 being rendered.

To prevent the virtual content 510 from obstructing/blocking an ability of the occupant 502 to see the event 512, the mobile device 150 can adjust one or more characteristics of the virtual content 510. In this example, at time $T_2$, the mobile device 150 increases a transparency of the virtual content 510 to enable visibility of the event 512 through the virtual content 510. As shown, at time $T_2$, the event 512 is visible through the virtual content 510 after its transparency has been increased. This allows the occupant 502 to see (and monitor/track) the event 512 and make any adjustments to the operation of the vehicle 202 that the occupant 502 deems necessary based on the event 512. For example, the occupant 502 can stop the vehicle 202 to allow the stroller associated with the event 512 to pass. The occupant 502 can drive away once the stroller has passed. As another example, the occupant 502 can accelerate/decelerate the vehicle 202 and/or implement any maneuver(s) that may allow the vehicle 202 to avoid the stroller associated with the event 512.

On the other hand, if the virtual content 510 were not adjusted as described above to allow the occupant 502 to see the event 512, the occupant 502 could potentially miss/overlook the event 512. Without seeing the event 512 (or without seeing the event 512 in time to react), the occupant 502 may otherwise not have been able to avoid the stroller associated with the event 512 or may have reacted abruptly and/or from a closer distance, which could have created a danger or may not have been timely enough to avoid the stroller.

Figures 6A, 6B:
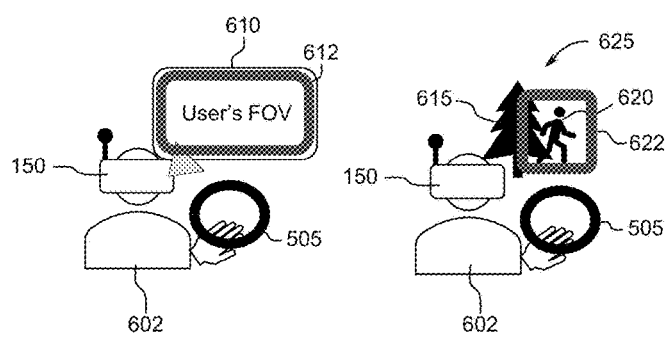
FIG. 6A through FIG. 6E are diagrams illustrating example use cases for modulating virtual content, in accordance with some examples of the present disclosure.

FIG. 6A through FIG. 6E are diagrams illustrating example use cases for modulating virtual content. With reference to FIG. 6A, the mobile device 150 in this example has determined that an occupant 602 of the vehicle 202 is distracted and an event will occur within a field-of-view (FOV) 610 of the occupant 602. In the present disclosure, the FOV 610 of the occupant 602 can be modified or defined by the mobile device 150. More specifically, the FOV 610 can be defined by the field-of-view visible on or through the respective display area of the mobile device 150. By way of example, the FOV 610 of an occupant 602 wearing smart glasses can be defined by the FOV through the smart glasses which is generally reduced as compared to the FOV of the occupant's naked eyes. In another example, the physiological/anatomical FOV of an occupant can be enlarged by displaying a larger FOV on displays of an HMD. In some examples, the FOV 610 can be the FOV on which the mobile device 150 can render virtual content. To emphasize the event within the FOV 610 and/or draw the attention of the occupant 602 to the event within the FOV 610, the mobile device 150 can render event-related virtual content 612 within the FOV 610. In this example, the virtual content 612 includes pulsing of the edges (or an outline) of the FOV 610. The pulsing of the edges can emphasize the area within the pulsed edges and draw the attention of the occupant 602 to that area.

In FIG. 6B, the mobile device 150 has detected, e.g., based on vehicle data 408, a vehicle event 625 where a pedestrian 620 has appeared from behind a tree 615 and is moving towards (or into) a path of the vehicle 202. The pedestrian 620 was previously blocked by the tree 615 and was not visible to the occupant 602 or the mobile device 150 or the vehicle 202 until the pedestrian 620 moved past the tree 615 and towards (or into) the path of the vehicle 202. To draw the attention of the occupant 602 to the vehicle event 625 (including the pedestrian 620) and/or to emphasize the location of the vehicle event 625 (including the pedestrian 620), the mobile device 150 has rendered a highlight 622 around the location of the vehicle event 625 and, more specifically, around the location of the pedestrian 620 associated with the vehicle event 625.

In some examples, the mobile device 150 can render a bounding box (or any other shape/geometry) around the vehicle event 625 and/or a portion thereof such as the pedestrian 620. In some cases, the mobile device 150 can render the highlight 622 according to one or more characteristics intended to draw (or further draw) the attention of the occupant 602. For example, the mobile device 150 can render the highlight 622 according to a certain size, color, pattern, shape, transparency, brightness, thickness, animation, and/or any other characteristics for rendering the highlight 622 to better draw the attention of the occupant 602.

Figures 6C, 6D, 6E:
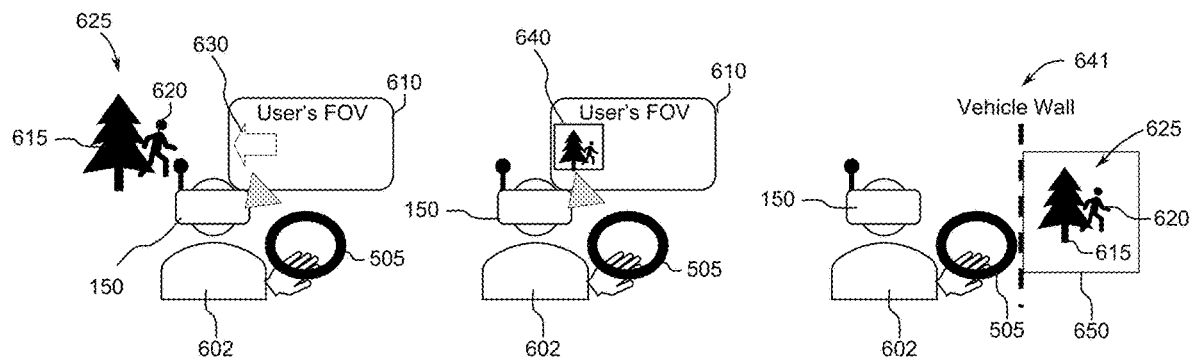

FIG. 6C illustrates another example for rendering content to draw the attention of the occupant 602 to the vehicle event 625 (including the pedestrian 620) and/or emphasizing the vehicle event 625 (including the pedestrian 620). In this example, the mobile device 150 has rendered a directional indicator 630 within the FOV 610 of the occupant 602. The directional indicator 630 directs the head and gaze of the occupant 602 in the direction of the vehicle event 625, including the pedestrian 620. The directional indicator 630 is shown in this example as a head-locked arrow. However, other examples can include other types and/or configurations of directional indicators.

In some cases, the mobile device 150 can render the directional indicator 630 according to one or more characteristics intended to draw/capture (or further draw/capture) the attention of the occupant 602. For example, the mobile device 150 can render the directional indicator 630 according to a certain size, color, pattern, shape, transparency, brightness, thickness, animation, and/or any other characteristics. In some cases, the mobile device 150 can pulse the periphery of the vision/view of the occupant 602 to further draw/capture the attention of the occupant 602.

FIG. 6D illustrates an example of live content corresponding to a vehicle event presented by the mobile device 150 for the occupant 602 of the vehicle 202. The vehicle event in this example includes the pedestrian 620 crossing/passing from behind the tree 615, as previously described. However, in this case, instead of rendering virtual content for the occupant 602, the mobile device 150 has presented a camera feed 640 obtained by the mobile device 150 from a vehicle camera (e.g., a backup camera, a side-view camera, a front camera, etc.) of the vehicle 202. The camera feed 640 can depict the vehicle event, including the pedestrian 620, and thus may allow the occupant 602 to observe the vehicle event.

For example, the vehicle camera can stream its feed to the mobile device 150. The mobile device 150 can then present the camera feed 640 from the vehicle camera, for consumption by the occupant 602. The camera feed 640 can depict the vehicle event, including the pedestrian 620. Thus, the camera feed 640 presented by the mobile device 150 can allow the occupant 602 to view the vehicle event (including the pedestrian 620) from the camera feed 640 presented by the mobile device 150.

FIG. 6E illustrates an exterior view 650 of the vehicle event 625 rendered by the mobile device 150. The exterior view 650 in this example is locked to (and/or projected on) a vehicle wall 641. In some examples, the vehicle wall 641 may be based on the vehicle template previously described herein. The vehicle wall 641 is shown as an interior wall on a passenger side of the vehicle 202. However, the exterior view 650 can be rendered on and/or locked to any wall, side, or portion of the vehicle interior.

The exterior view 650 can depict the vehicle event 625, including the pedestrian 620. In some examples, the exterior view 650 can include a virtual content rendering of the vehicle event 625. In other examples, the exterior view 650 can include a live content rendering (e.g., a camera feed) of the vehicle event 625. The exterior view 650 can be rendered such that the vehicle wall 641 appears transparent or translucent to the occupant 602 and the vehicle event 625 appears visible to the occupant 602 (e.g., as rendered by the exterior view 650). In some cases, the exterior view 650 can be warped and/or perspective corrected based on a position of the mobile device 150 (and thus the occupant 602 wearing the mobile device 150) relative to the coordinate system of the vehicle and/or a position of the vehicle event 625 relative to the coordinate system of the vehicle.

In some cases, the content rendered by the mobile device 150 can include vehicle data (e.g., vehicle data 408) or a portion of vehicle data. For example, the content rendered in any of the examples shown in FIG. 6A through 6E can include vehicle data or a portion of vehicle data such as, for example, vehicle status information, vehicle instrumentation data, vehicle information, data from one or more sensors of the vehicle 202, etc. To illustrate, the content rendered by the mobile device 150 can include an indication of a speed of the vehicle 202, a direction of the vehicle 202, a route of the vehicle 202, a battery status of the vehicle 202, a fuel state of the vehicle 202, an oil state of the vehicle 202, a mileage associated with the vehicle 202, navigation data associated with the vehicle 202, a tire pressure (and/or a tire state/status) associated with one or more tires of the vehicle 202, an indication of a control signal that is active/on/enabled at the vehicle 202, information about vehicle brakes, vehicle warnings, vehicle errors, information (e.g., a state/status, a warning, etc.) about one or more vehicle lights (e.g., a headlight, tail light, reverse light, daytime running light, fog light, off-road light, signal light, brake light, emergency light, etc.), information about a steering system, information about one or more vehicle systems and/or autonomous functions, cruise control status information, seat belt information, and/or any other vehicle information and/or instrumentation.

In some cases, the mobile device 150 can render vehicle information (e.g., vehicle status information, instrumentation, navigation information, etc.) streamed from the vehicle 202. In some examples, the mobile device 150 can present the vehicle information as a head-locked HUD or a world-locked user interface (UI) element(s). In some cases, the mobile device 150 can render virtual content to replace real-world content and/or events that may be distracting to the occupant, such as billboards, accidents, etc. In some aspects, the mobile device 150 can render any of the virtual content described herein using a deep neural network trained to generate "deepfaked" (e.g., synthetic) virtual content from a database of images. In some cases, the "deepfaked" virtual content can be rendered in the style observed by the mobile device 150 and/or the vehicle 202.

As previously mentioned, the monitoring engine 410 of the AR application 310 of the mobile device 150 can monitor and understand a state of one or more occupants of the vehicle 202. In some cases, the monitoring engine 402 of the vehicle application 302 of the vehicle computing system 210 can alternatively or additionally (e.g., in combination with the monitoring engine 410 of the AR application 310 or separately) monitor and understand the state of one or more occupants of the vehicle 202. In some examples, the state of an occupant can include one or more characteristics of the occupant such as, for example, a detected impairment, an eye gaze, a location, a pose (e.g., orientation, location, etc.) of the occupant, a head pose of the occupant, a gesture, a facial expression, a hand gesture, an activity, an emotion, a motion, an intent to perform an action, and/or other characteristics of the occupant.

For instance, the monitoring engine 410 and/or the monitoring engine 402 (alone or in combination with data from the mobile device 150 such as the monitoring engine 410) can detect and/or recognize various states of an occupant of a vehicle. FIG. 7A through FIG. 7I are diagrams illustrating different example states of an occupant 750 driving the vehicle 202, as detected by the monitoring engine 410 of the AR application 310 of the mobile device 150 and/or the monitoring engine 402 of the vehicle 202. The occupant 750 in the examples shown in FIG. 7A through FIG. 7I is a driver of the vehicle 202 wearing the mobile device 150.

Figure 7A:
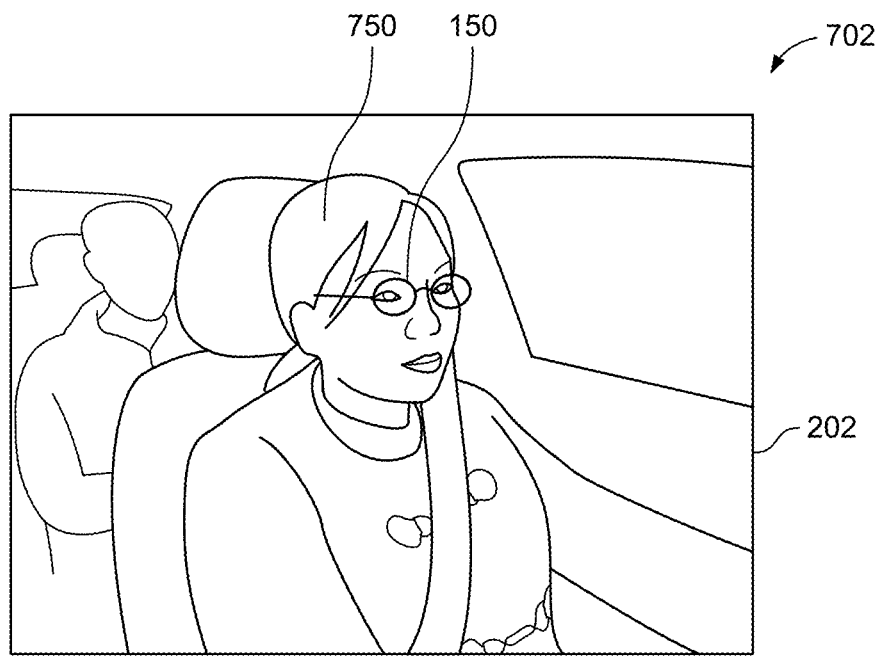
FIG. 7A through FIG. 7I are diagrams illustrating different example states of an occupant driving a vehicle, in accordance with some examples of the present disclosure.

In the example shown in FIG. 7A, the occupant 750 is wearing the mobile device 150, such as smart glasses, and performing a normal driving activity 702. The monitoring engine 410 can determine that the occupant 750 is performing the normal driving activity 702. As shown, the normal driving activity 702 in this example includes the occupant 750 looking directly out of the windshield of the vehicle 202 with both hands on the steering wheel. Moreover, during the normal driving activity 702, the occupant 750 is not impaired (e.g., distracted, etc.).

Figure 7B:
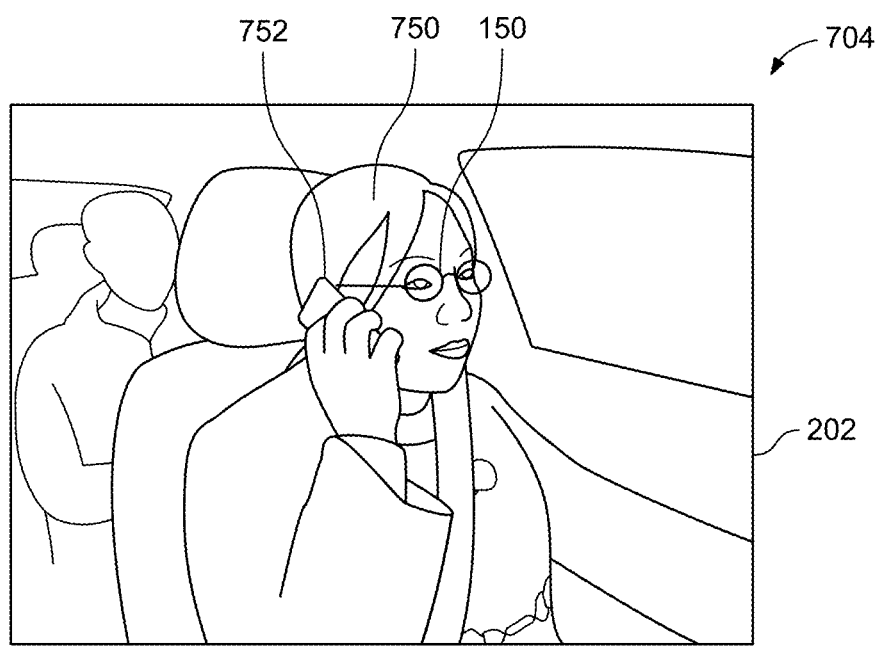

FIG. 7B illustrates an example state 704 of the occupant 750 while driving the vehicle 202. In this example, the state 704 includes the occupant 750 using a mobile phone 752 by holding the mobile phone 752 to her ear while driving the vehicle 202. In some cases, the monitoring engine 410 can determine that the occupant 750 is using the mobile phone 752 and determine that the use of the mobile phone 752 can impair (e.g., distract) the occupant 750. Thus, in some examples, the monitoring engine 410 can determine an impairment of the occupant 750 based on the use of the mobile phone 752. The impairment in this example includes a distraction. The monitoring engine 410 can also determine that, if the occupant 750 needs to use the hand holding the mobile phone 752 to take control of the steering wheel and/or any other vehicle controls, having that hand occupied can delay (and thus impair) the occupant's ability to take control of the steering wheel and/or any other vehicle controls, and therefore increases the risk of an accident. Generally, the monitoring engine 410 can detect a state of impairment based on a location and/or activity of one or both hands of the occupant, e.g., based on determining that at least one hand is not on the steering wheel. In some examples, the monitoring engine 410 can detect a state of impairment based on the occupant operating a mobile phone.

Figure 7C:
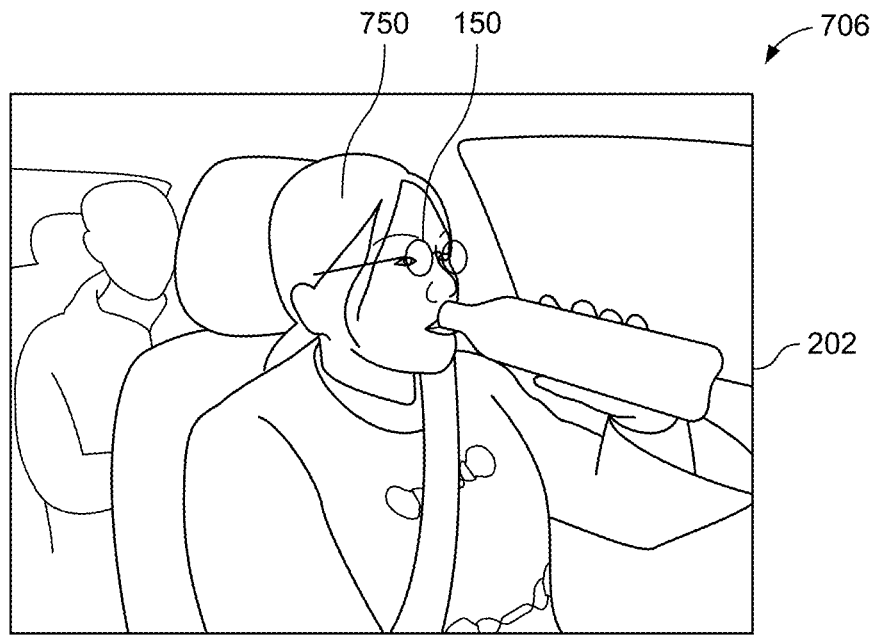

FIG. 7C illustrates another example state 706 of the occupant 750 driving the vehicle 202. In this example, the state 706 of the occupant 750 includes the occupant 750 drinking a beverage. The monitoring engine 410 can determine that the occupant 750 is drinking the beverage as shown in FIG. 7C. In some cases, the monitoring engine 410 can determine that the drinking of the beverage impairs the occupant 750 (e.g., impairs an ability of the occupant 750 to drive the vehicle 202, impairs a reaction and/or reaction time of the occupant 750 to vehicle events, increases the difficulty of driving the vehicle 202, increases the risk of an accident, etc.). For example, the monitoring engine 410 can determine that the drinking of the beverage distracts the occupant 750 and/or occupies at least one of the hands of the occupant 750, and thus prevents the occupant 750 from using that hand to operate the vehicle 202 and/or respond to vehicle events. The monitoring engine 410 can also determine that, if the occupant 750 needs to use that hand to take control of the steering wheel and/or any other vehicle controls, having that hand occupied can delay (and thus impair) the occupant's ability to take control of the steering wheel and/or any other vehicle controls, and therefore increases the risk of an accident. Generally, the monitoring engine 410 can detect a state of impairment based on a location and/or activity of one or both hands of the occupant, e.g., based on determining that at least one hand is not on the steering wheel.

Figure 7D:
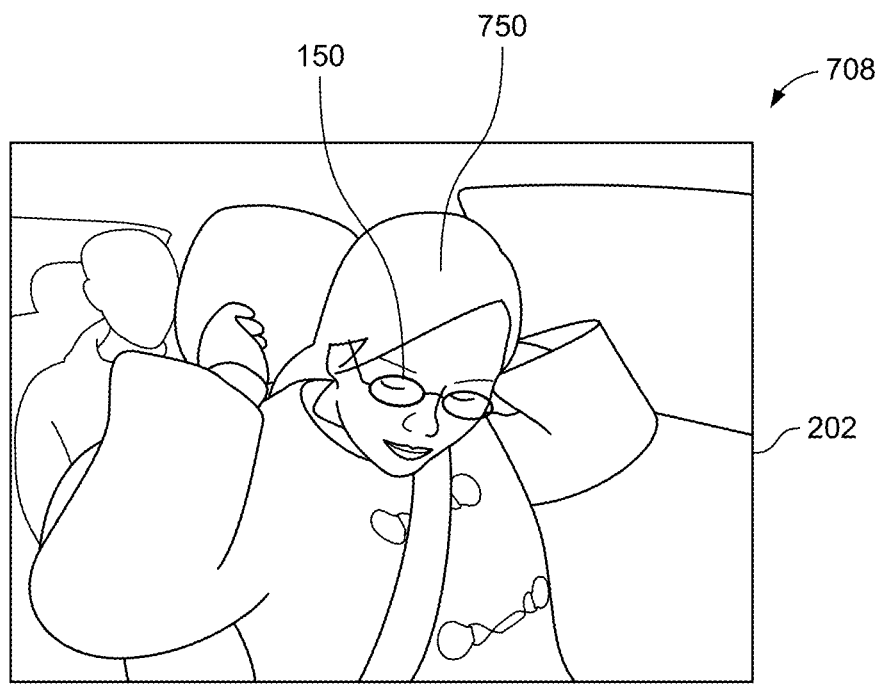

FIG. 7D illustrates another example state 708 of the occupant 750 driving the vehicle 202. In this example, the state 708 includes the occupant 750 adjusting her hair. As shown, the occupant 750 has both hands off the steering wheel of the vehicle 202 while she adjusts her hair. The monitoring engine 410 can determine that the occupant 750 is adjusting her hair and has both hands off the steering wheel. In some cases, the monitoring engine 410 can determine that having both hands off the steering wheel impairs the occupant 750 (e.g., impairs an ability of the occupant 750 to drive the vehicle 202, impairs a reaction and/or reaction time of the occupant 750 to vehicle events, increases the difficulty of driving the vehicle 202, increases the risk of an accident, etc.). For example, the monitoring engine 410 can determine that adjusting the hair distracts the occupant 750 and/or that having both hands off the steering wheel prevents the occupant 750 from using the hands to operate the vehicle 202 and/or respond to events. The monitoring engine 410 can also determine that, if the occupant 750 needs to take control of the steering wheel (and/or any other vehicle controls), having her hands off the steering wheel to adjust her hair can delay (and thus impair) her ability to take control of the steering wheel (and/or any other vehicle controls), and therefore increases the risk of an accident. Generally, the monitoring engine 410 can detect a state of impairment based on a location and/or activity of one or both hands of the occupant, e.g., based on determining that at least one hand is not on the steering wheel.

Figure 7E:
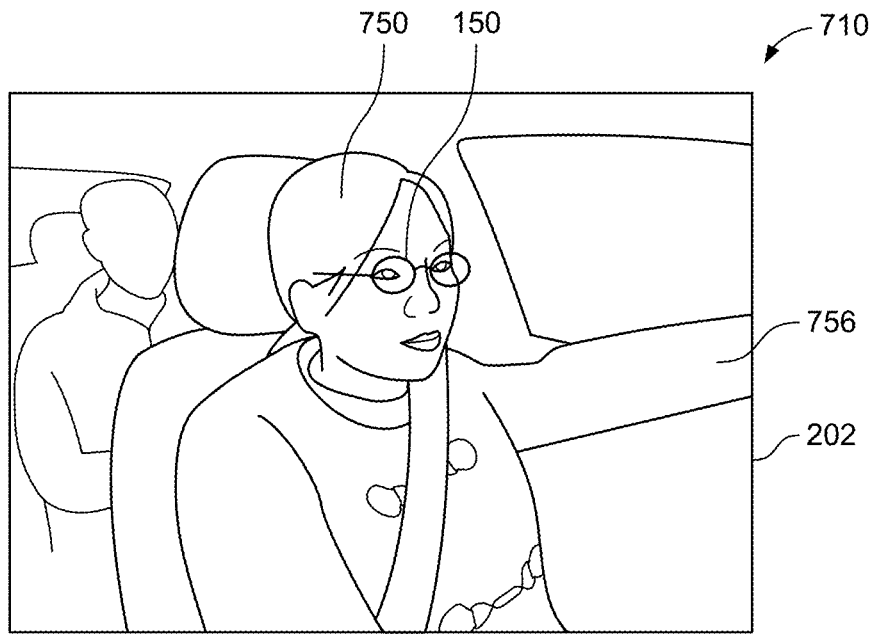

FIG. 7E illustrates another example state 710 of the occupant 750 driving the vehicle 202. In this example, the state 710 includes extending an arm 756 out of the driver's side window of the vehicle 202. As shown, the occupant 750 has the arm 756 extended outside of the driver's side window, leaving the hand of that arm 756 off the steering wheel and any other vehicle controls. The monitoring engine 410 can determine that the occupant 750 has the arm 756 extended outside of the driver's side window and the hand of that arm 756 off the steering wheel and any other vehicle controls. In some cases, the monitoring engine 410 can determine that having the arm 756 out of the driver's side window and the hand of that arm 756 off the steering wheel and any other vehicle controls impairs the occupant 750 (e.g., impairs an ability of the occupant 750 to drive the vehicle 202, impairs a reaction and/or reaction time of the occupant 750 to vehicle events, increases the difficulty of driving the vehicle 202, increases the risk of an accident, etc.). For example, the monitoring engine 410 can determine that having the arm 756 out of the driver's side window and the hand of that arm 756 off the steering wheel and any other vehicle controls prevents the occupant 750 from quickly using that hand to operate the vehicle 202 and/or respond to events. In some examples, the monitoring engine 410 can determine that, if the occupant 750 needs to use the hand of the arm 756 to take control of the steering wheel and/or any other vehicle controls, having the arm 756 and the hand of that arm 756 temporarily unavailable (e.g., extended outside of the driver's side window) can delay (and thus impair) the occupant's ability to take control of the steering wheel and/or any other vehicle controls, and therefore increases the risk of an accident. Generally, the monitoring engine 410 can detect a state of impairment based on a location and/or activity of one or both hands of the occupant, e.g., based on determining that at least one hand is not on the steering wheel.

Figure 7F:
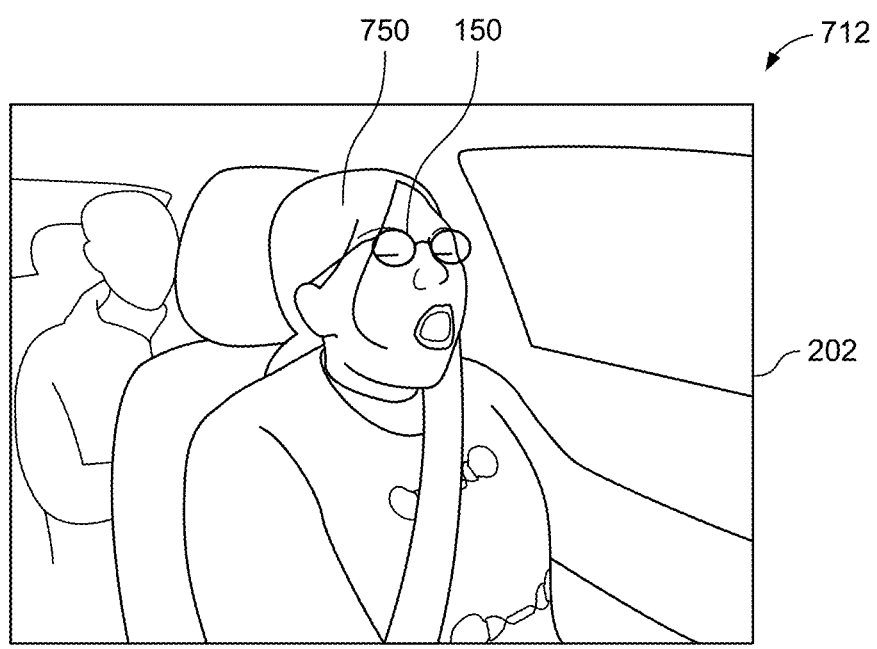

FIG. 7F illustrates another example state 712 of the occupant 750 driving the vehicle 202. In this example, the state 712 includes yawning while driving the vehicle 202. The monitoring engine 410 can determine that the occupant 750 is yawning while driving the vehicle 202. In some cases, the monitoring engine 410 can determine that the yawning indicates an impairment of the occupant 750. For example, the monitoring engine 410 can determine that yawning indicates a sleepy/drowsy state and/or a limited focus/attention that may negatively affect the ability of the occupant 750 to drive the vehicle 202 and/or respond to vehicle events. Generally, the monitoring engine 410 can detect a state of impairment based on a facial expression, such as yawning, closed/drooping eyes/eyelids, etc., and/or a body posture of the occupant indicating a state of the occupant with limited/reduced focus/attention.

Figure 7G:
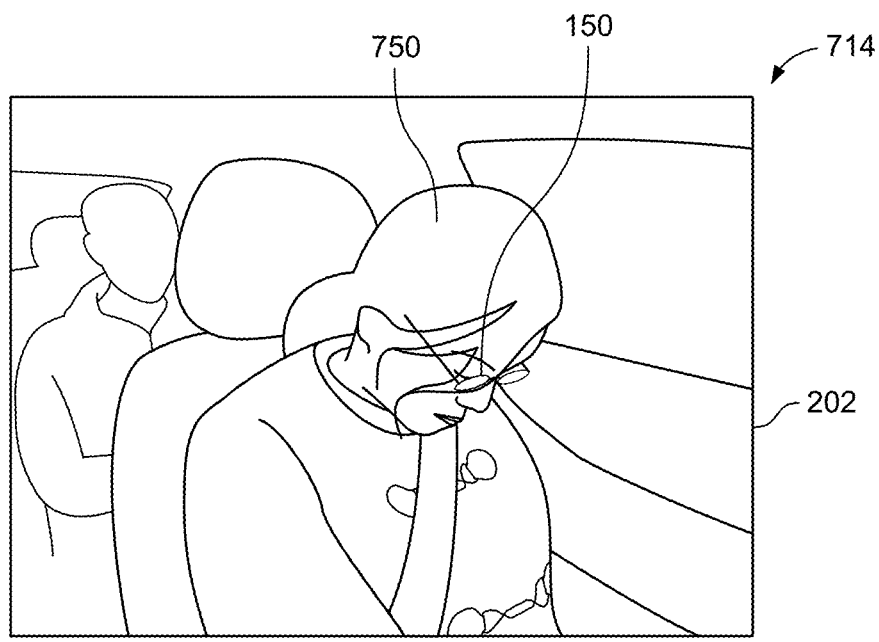

FIG. 7G illustrates another example state 714 of the occupant 750 driving the vehicle 202. In this example, the state 714 includes the occupant 750 looking down toward the lap of the occupant 750 while driving the vehicle 202. The monitoring engine 410 can determine that the occupant 750 is looking down toward the lap of the occupant 750 while driving the vehicle 202. In some cases, the monitoring engine 410 can determine that looking down toward the lap of the occupant 750 while driving impairs the ability of the occupant 750 to operate the vehicle 202 and/or respond to vehicle events. For example, the monitoring engine 410 can determine that looking down toward the lap of the occupant 750 distracts the occupant 750 and prevents the occupant 750 from seeing the road and outside environment and quickly detecting and responding to vehicle events associated with the driving of the vehicle 202. Generally, the monitoring engine 410 can detect a state of impairment based on a facial expression, such as yawning, closed/drooping eyes/eyelids, etc., and/or a body posture of the occupant indicating a state of the occupant with limited/reduced focus/attention.

Figure 7H:
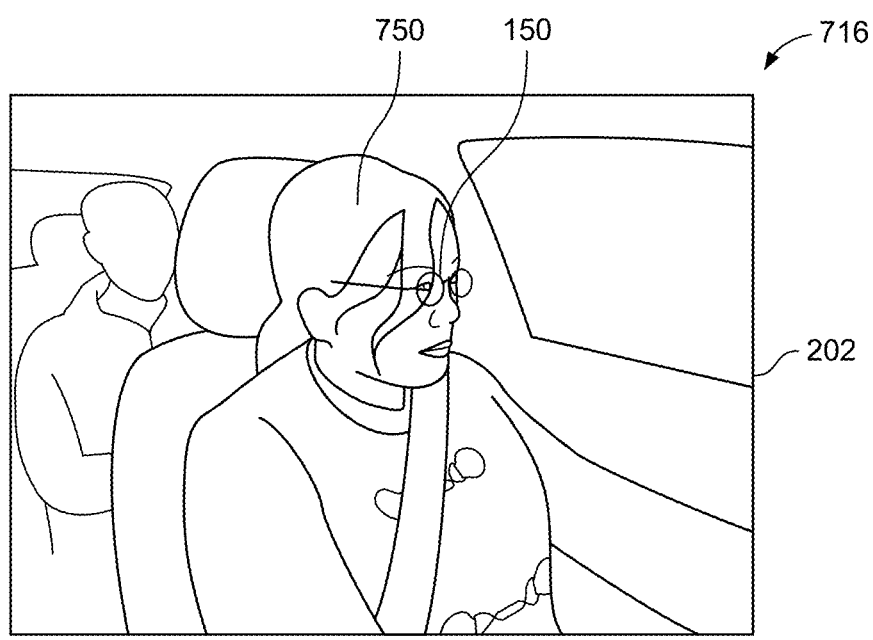

FIG. 7H illustrates another example state 716 of the occupant 750 driving the vehicle 202. In this example, the state 716 includes the occupant 750 looking to her left and outside of the driver's side window of the vehicle 202 while driving the vehicle 202. The monitoring engine 410 can determine that the occupant 750 is looking to her left and outside of the driver's side window of the vehicle 202 while driving the vehicle 202. In some cases, depending on the context of the vehicle 202, the monitoring engine 410 can determine that looking to her left and outside of the driver's side window of the vehicle 202 while driving impairs the ability of the occupant 750 to operate the vehicle 202 and/or respond to vehicle events. For example, depending on the context of the vehicle 202, the monitoring engine 410 can determine that looking to her left and outside of the driver's side window of the vehicle 202 distracts the occupant 750 and prevents the occupant 750 from seeing the road ahead and/or anything along the forward path of the vehicle 202, and impairs the ability of the occupant 750 to detect and respond to vehicle events along a forward path of the vehicle 202. Generally, the monitoring engine 410 can detect a state of impairment based on an eye gaze of the occupant, such as looking in/focusing on a direction away from the road ahead.

In other cases, depending on the context of the vehicle 202, the monitoring engine 410 can determine that looking to her left and outside of the driver's side window of the vehicle 202 while driving does not impair the ability of the occupant 750 to operate the vehicle 202 and/or respond to vehicle events. For example, if the context of the vehicle 202 indicates that a vehicle event has occurred outside of the driver's side window and the occupant 750 should be aware of and/or respond to the vehicle event, the monitoring engine 410 can determine that looking to her left and outside of the driver's side window of the vehicle 202 allows the occupant 750 to see the vehicle event and determine how (or if) to respond to the vehicle event. Accordingly, the monitoring engine 410 may determine that, in this example context, the occupant 750 looking to her left and outside of the driver's side window of the vehicle 202 while driving is appropriate and should not be classified or treated as an impairment.

Figure 7I:
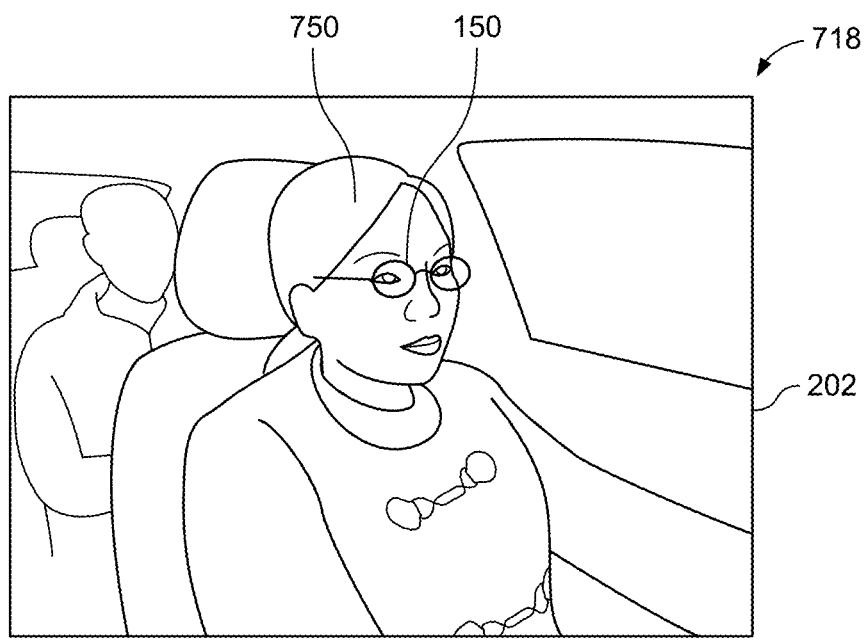

FIG. 7I illustrates another example state 718 of the occupant 750 driving the vehicle 202. In this example, the state 718 includes the occupant 750 with no seat belt fastened while driving the vehicle 202. The monitoring engine 410 can determine that the occupant 750 does not have the seat belt fastened while driving the vehicle 202. In some cases, the monitoring engine 410 can determine that not having the seat belt fastened while driving the vehicle 202 is an impairment if it increases the risk to the safety of the occupant 750 and others (e.g., any other passengers of the vehicle 202 and any other people in an environment of the vehicle 202, such as occupants of other vehicles, pedestrians, etc.). In other cases, the monitoring engine 410 may determine that not having the seat belt fastened while driving the vehicle 202 is not an impairment if it does not impair the ability of the occupant 750 to drive the vehicle 202 or respond to vehicle events.

Figure 8:
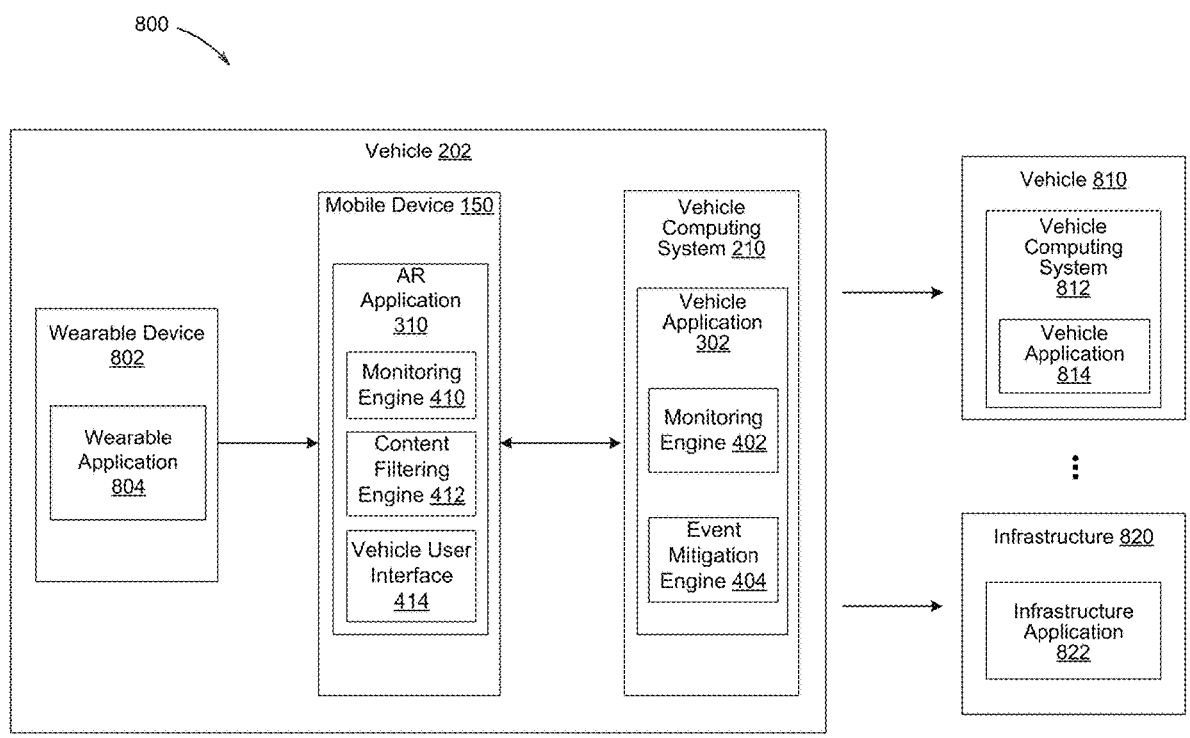
FIG. 8 is a diagram illustrating example of vehicle-to-everything communications including occupant monitoring events, in accordance with some examples of the present disclosure.

FIG. 8 is a diagram illustrating example of V2X communications 800 including occupant monitoring events. In this example, the mobile device 150 is a wearable augmented reality (AR) device, such as an HMD or AR glasses, worn by an occupant of the vehicle 202. The occupant of the vehicle 202 is also wearing a wearable device 802, such as a smart or connected watch, a health tracker/monitor device, a smart or connected bracelet device, a wearable medical device, or any other wearable device.

The mobile device 150 and the vehicle computing system 210 can exchange data as previously described, such as vehicle data (e.g., vehicle context information, vehicle template, vehicle sensor data, etc.), event data, and/or occupant data (e.g., occupant state information, occupant sensor measurements, occupant health measurements, etc.). The wearable device 802 can include a wearable application 804 that can track/measure information about the occupant, such as health metrics, biometrics, etc. The wearable device 802 can include health and other sensors such as, for example and without limitation, an oximeter, a skin sensor, an optical heart sensor, a photoplethysmography sensor, an electrical heart sensor, an accelerometer, a gyroscope, an electrocardiogram sensors, a temperature sensor, a blood pressure sensor, a galvanic skin response sensor, an electroencephalogram sensor, and/or any other sensors.

In some examples, the wearable device 802 can have additional and/or redundant sensor modalities (e.g., relative to sensor modalities of the mobile device 150) that can aid the occupant monitoring. The wearable device 802 can send such data (or a digest of relevant events) to the mobile device 150 to aid in its occupant monitoring process. In some examples, the wearable device 802 can send to the mobile device 150 sensor data such as, for example, inertial sensor data, heart rate measurements, blood pressure measurements, galvanic skin response measurements, ECG/EKG/EEG data, temperature data, oxygen levels, motion information, sleep tracking information, etc. In some cases, the data from the wearable device 802 can indicate and/or can be used to determine (e.g., via a machine learning classifier trained on positive and negative examples) impairments such as drowsiness, intoxication, a health emergency, stress, a heightened emotional state, loss of consciousness, etc.

The wearable application 804 of the wearable device 802 can obtain health measurements and any other measurements from the one or more sensors on the wearable device

802. The wearable device 802 can send any health measurements to the mobile device 150. The mobile device 150 can use the health measurements to monitor a state of the occupant. The mobile device 150 can use the health measurements alone or in combination with other measurements from the mobile device 150, such as any measurements previously described with respect to the monitoring engine 410. In some examples, the mobile device 150 can perform sensor data fusion and use the combination of health measurements from the wearable device 802 and any occupant monitoring measurements and/or data from the mobile device 150 to determine a state of the occupant. The mobile device 150 can use the monitoring engine 410 to determine the state of the occupant as previously described. The monitoring engine 410 can use any of the data from the mobile device 150 and/or the wearable device 802 to determine the state of the occupant.

In some cases, the mobile device 150 can send the determined state of the occupant to the vehicle computing system 210. The mobile device 150 can additionally or alternatively send any event data to the vehicle computing system 210, as previously described. In some cases, the mobile device 150 can send the determined state of the occupant to other devices such as, for example, vehicle 810 (e.g., vehicle computing system 812), infrastructure 820, and/or any other device. The infrastructure 820 can include any infrastructure system(s), device(s), and/or component(s) such as, for example and without limitation, a traffic light, a traffic camera, a streetlight, a signage, a parking meter, a lane marker, one or more emergency response systems, a combination thereof, and/or any other infrastructure system, device, and/or component. In some cases, the vehicle computing system 210 can send/forward the determined state of the occupant to other device such as, for example, vehicle 810 (e.g., vehicle computing system 812), infrastructure 820, and/or any other device.

In some cases, the vehicle computing system 210 can also determine (e.g., via the monitoring engine 402) a state of the occupant using data from one or more sensors of the vehicle 202, such as one or more image sensors, inertial sensors, weight sensors, pressure sensors, audio sensors, etc., and/or event data 424 from the mobile device 150. For example, in some cases, the vehicle computing system 210 can determine a state of the occupant in addition to the determination of the state of the occupant made by the mobile device 150. In some examples, the vehicle computing system 210 can use sensor data from the mobile device 150, the wearable device 802, and/or one or more sensors of the vehicle 202 to determine the state of the occupant. For example, the vehicle computing system 210 can fuse sensor data from the mobile device 150, the wearable device 802, and/or one or more sensors of the vehicle 202 to determine the state of the occupant. In some cases, the vehicle computing system 210 can use the state of the occupant received from the mobile device 150 to aid its own determination of the state of the occupant. In other cases, the vehicle computing system 210 can separately determine the state of the occupant without the state of the occupant determined by the mobile device 150 and/or sensor data from the mobile device 150.

The vehicle computing system 210 of the vehicle 202 can communicate any vehicle and/or occupant data to other devices such as, for example, the vehicle 810 and/or the infrastructure 820. For example, the vehicle computing system 210 can send a determined state of the occupant to the vehicle 810 and/or the infrastructure 820 (e.g., in addition to or instead of the mobile device 150 sending a state of the occupant to the vehicle 810 and/or the infrastructure 820). The vehicle 810 and/or the infrastructure 820 can use any state information of the occupant received from the mobile device 150 and/or the vehicle 202 to seek assistance to the occupant if the state information indicates an impairment of the occupant and/or to perform any actions to prevent any accidents or collisions with the vehicle 202 operated by the occupant while impaired.

For example, the vehicle application 814 of the vehicle computing system 812 of the vehicle 810 can use the data from the vehicle 202 and/or the mobile device 150 to adjust an operation/behavior of the vehicle 810 to avoid any accidents or collisions with the vehicle 202. In some cases, the vehicle application 814 of the vehicle computing system 812 of the vehicle 810 can use the data from the vehicle 202 and/or the mobile device 150 to re-route the vehicle 810 to avoid the vehicle 202 and/or maintain at least a certain distance from the vehicle 202. The vehicle computing system 812 can be configured and comprise the same or similar components as the vehicle computing system 210 previously described in combination with FIG. 2.

As another example, the infrastructure application 822 of the infrastructure 820 can use the data from the vehicle 202 and/or the mobile device 150 to adjust an operation/behavior of the infrastructure 820. To illustrate, the infrastructure application 822 of the infrastructure 820 can use the data from the vehicle 202 and/or the mobile device 150 to adjust traffic controls/signals associated with the infrastructure 820 based on an impairment of the occupant of the vehicle 202 and/or to report the impairment of the occupant of the vehicle 202 to law enforcement and/or other emergency or assistance personnel and/or systems.

In some examples, the vehicle computing system 210 can also send other information to the vehicle 810 and/or the infrastructure 820. For example, the vehicle computing system 210 can send sensor data from the vehicle 202 and/or a determined context of the vehicle 202 to the vehicle 810 and/or the infrastructure 820. In some cases, the vehicle computing system 210 can send such information in addition to any state information about the occupant of the vehicle 202.

Figure 9:
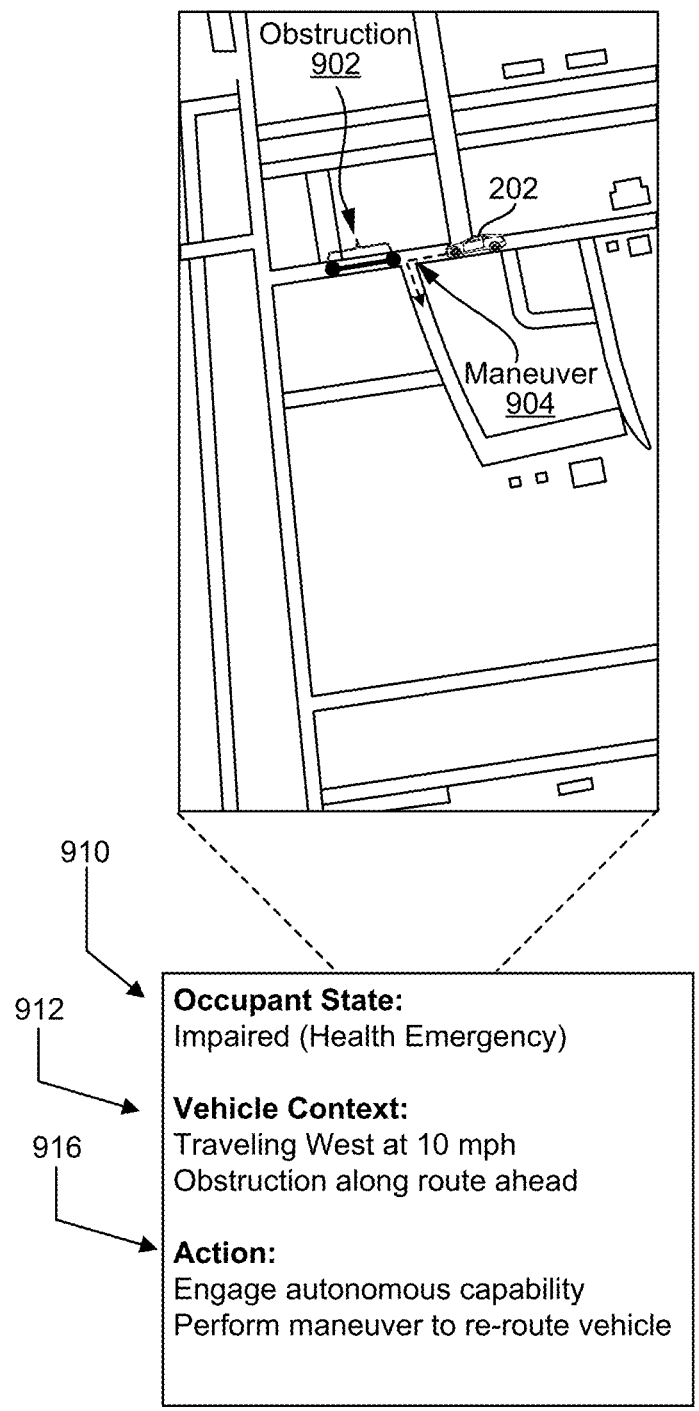
FIG. 9 and FIG. 10 are diagrams illustrating example vehicle mitigation events based on an occupant state determined by the mobile device worn by an occupant driving the vehicle, in accordance with some examples of the present disclosure.

FIG. 9 is a diagram illustrating an example vehicle mitigation event based on an occupant state determined by the mobile device 150 worn by an occupant driving the vehicle 202. In this example, the mobile device 150 has determined (e.g., via monitoring engine 410, and possibly based on data from the wearable device 802) an occupant state 910 that indicates that the occupant driving the vehicle 202 is impaired by a health emergency. The mobile device 150 can send the occupant state 910 to the vehicle computer system (e.g., vehicle computing system 210) of the vehicle 202 to notify the vehicle 202 that the occupant is impaired by a health emergency.

The vehicle computer system (e.g., vehicle computing system 210) of the vehicle 202 determines a vehicle context 912 describing a state of the vehicle 202, such as a state of movement of the vehicle 202. In this example, the vehicle context 912 indicates that the vehicle 202 is traveling west at 10 miles per hour (mph) and has encountered a vehicle event ahead. The vehicle event in this example is an obstruction 902 along a route of the vehicle 202.

Based on the occupant state 910 obtained from the mobile device 150 and the vehicle context 912, the vehicle computing system (e.g., via an event mitigation engine such as event mitigation engine 404) of the vehicle 202 can trigger an action 916. In this example, the action 916 includes engaging an autonomous capability of the vehicle 202 to take control of the vehicle 202 while the occupant is impaired by the health emergency. In some examples, the vehicle 202 can use the autonomous capability to drive the occupant to the destination route. In other examples, the vehicle 202 can use the autonomous capability to re-route the vehicle 202 and drive the occupant to a hospital/clinic or a location where the occupant can obtain treatment for the health emergency. In some cases, the vehicle 202 can also send a message/notification to a remote system, such as a health emergency system, indicating that the occupant is experiencing a health emergency and/or requesting help for the health emergency.

The action 916 also includes performing a maneuver 904 to avoid the obstruction 902. The vehicle 202 can use the autonomous capability to perform the maneuver 904 to avoid the obstruction 902. In this example, the maneuver 904 includes turning left on a road prior to the obstruction 902.

The obstruction 902, maneuver 904, occupant state 910, vehicle context 912, and action 916 shown in FIG. 9 are merely illustrative examples provided for explanation purposes. Other examples can include the same or different and/or additional obstructions, maneuvers, occupant states, vehicle contexts, actions, etc.

In some examples, a vehicle context can include information related to the operation/driving of vehicle; an event or vehicle event can include information related to a vehicle safety, a vehicle safety event/condition, etc.; and a state of an occupant can include and/or relate to a distraction or health condition of the occupant. In some cases, the distraction or health condition can include a transient distraction or health condition of the occupant.

Figure 10:
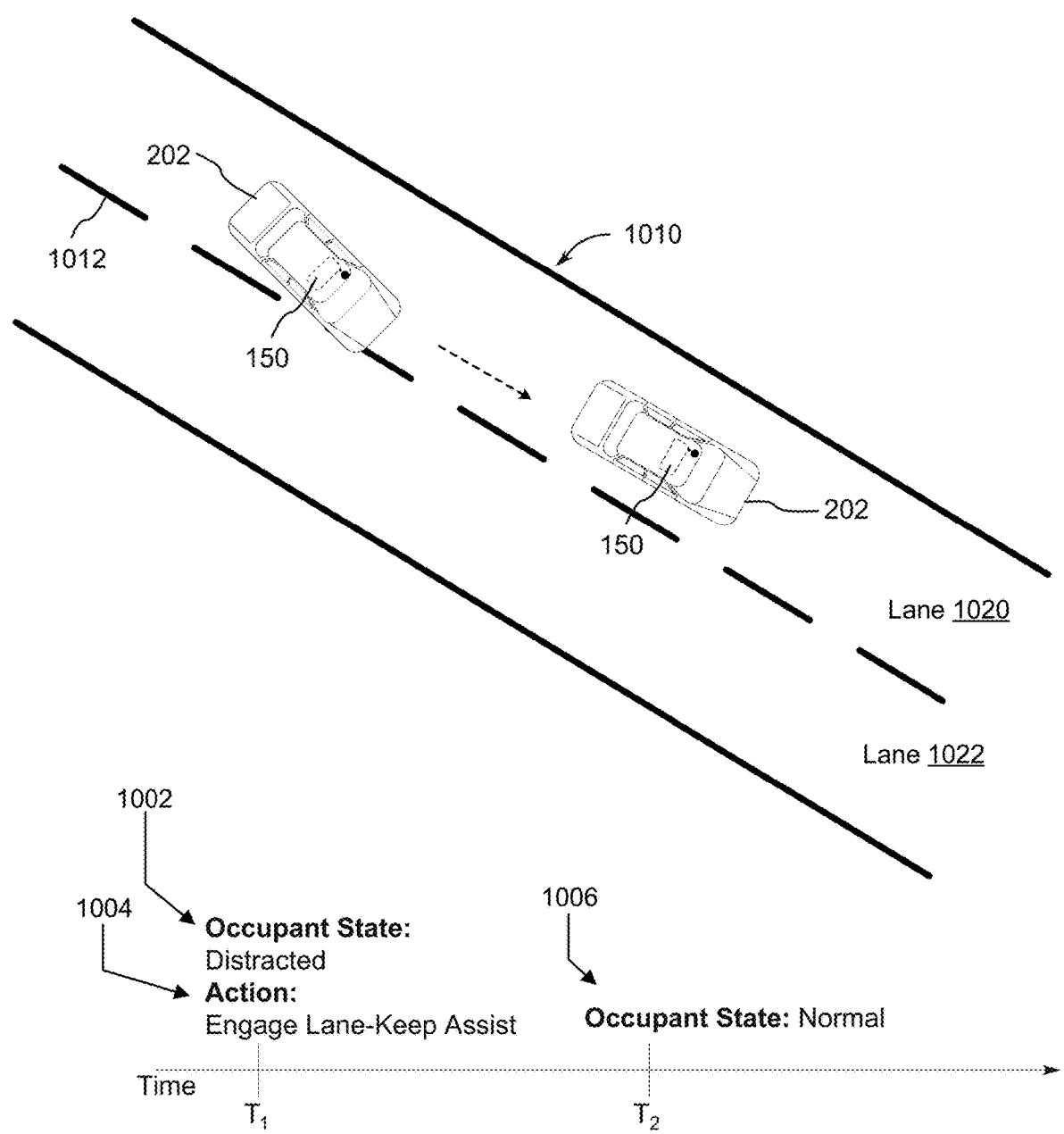

FIG. 10 is a diagram illustrating another example vehicle mitigation event based on an occupant state determined by the mobile device 150 worn by an occupant driving the vehicle 202. In this example, the mobile device 150 has determined (e.g., via monitoring engine 410) an occupant state 1002 that indicates that the occupant driving the vehicle 202 is distracted. The mobile device 150 can send the occupant state 1002 to the vehicle computer system (e.g., vehicle computing system 210) of the vehicle 202 to notify the vehicle 202 that the occupant is distracted.

The vehicle 202 can detect (e.g., via a monitoring engine such as monitoring engine 402) that the vehicle 202 is crossing the center lane 1012 or a lane divider of the road 1010 the vehicle 202 is traveling on. Based on the occupant state 1002 indicating that the occupant is distracted and the determination that vehicle 202 is crossing the center lane 1012 of the road 1010, at time $T_1$, the vehicle 202 can trigger (e.g., via an event mitigation engine such as event mitigation engine 404) an action 1004 to assist the distracted occupant. In this example, the action 1004 includes engaging a lane-keep assist function of the vehicle 202 to take corrective action to keep the vehicle 202 in its lane 1020 and avoid the vehicle 202 from crossing into another lane 1022.

At time $T_2$, after the vehicle 202 has engaged the lane-keep assist function and taken corrective action, the vehicle 202 is now traveling within its lane 1020. As shown in FIG. 10, the occupant state 1006 also indicates that the occupant of the vehicle is in a normal state (e.g., is not impaired) at time $T_2$. The vehicle 202 can allow the occupant to drive the vehicle 202 with or without autonomous assistance, can continue to implement one or more autonomous driving operations, or can provide the occupant an option to choose whether to manually control the vehicle 202 (fully or partially), to allow the vehicle 202 to operate autonomously, etc.

Figure 11:
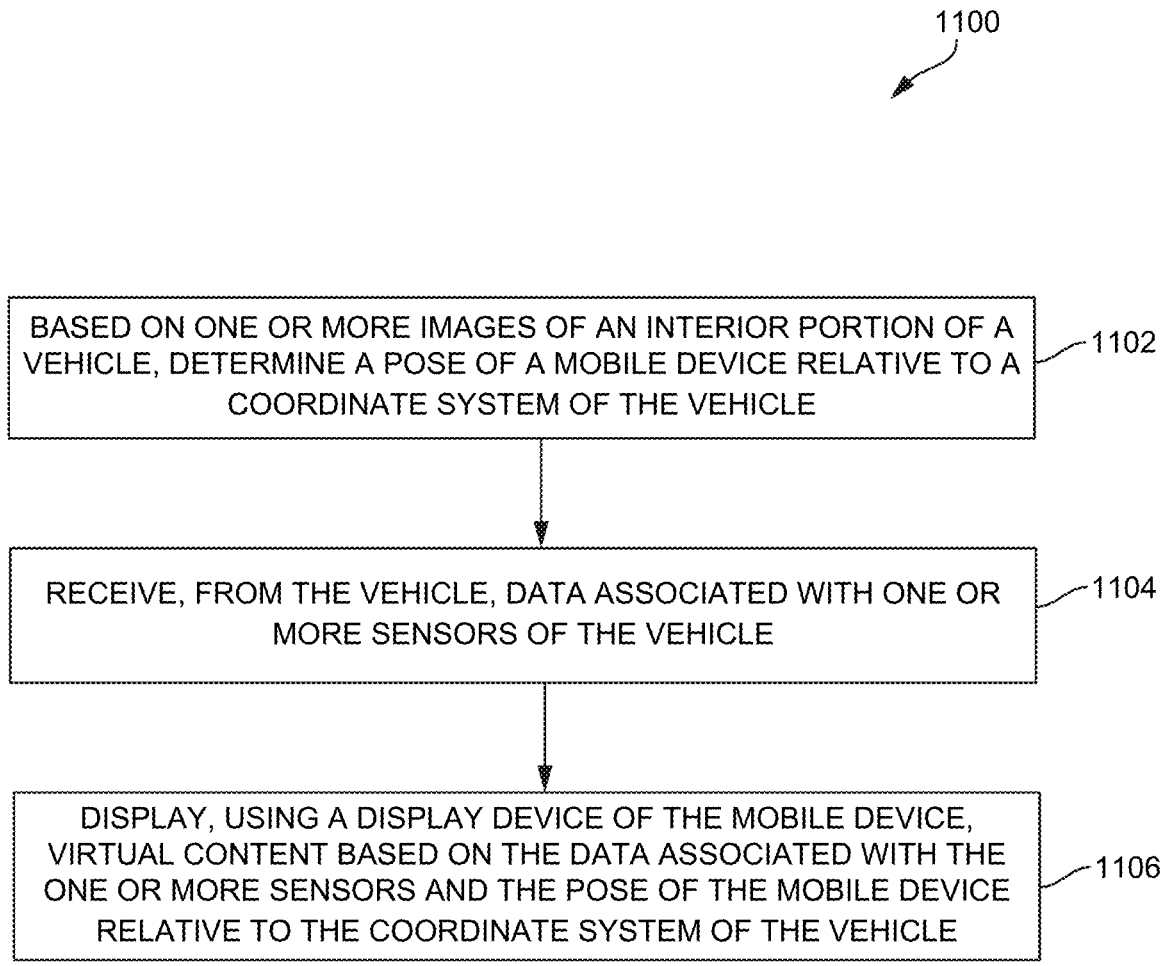
FIG. 11 is a flowchart illustrating an example process for controlling a presentation of virtual content during an operation of a vehicle, in accordance with some examples of the present disclosure.

FIG. 11 is a flowchart illustrating an example process 1100 for controlling a presentation of virtual content during an operation of a vehicle. At block 1102, the process 1100 can include determining, based on one or more images of an interior portion of a vehicle (e.g., vehicle 202), a pose of a mobile device (e.g., mobile device 150) relative to a coordinate system of the vehicle.

At block 1104, the process 1100 can include receiving, from the vehicle, data associated with one or more sensors of the vehicle.

At block 1106, the process 1100 can include displaying, using a display device of the mobile device, virtual content based on the data associated with the one or more sensors and the pose of the mobile device relative to the coordinate system of the vehicle.

In some aspects, the process 1100 can include determining a context of the vehicle based on the data associated with the one or more sensors. In some examples, the context can include an event related to the vehicle.

In some aspects, the process 1100 can include associating a location of the virtual content relative to a coordinate system of the mobile device with a location of the event relative to the coordinate system of the vehicle; and based on the association of the location of the virtual content relative to the coordinate system of the mobile device with the location of the event relative to the coordinate system of the vehicle, display a live content feed from one or more visual image sensors of the mobile device.

In some examples, displaying the live content feed can include determining a pose of the mobile device relative to the event based on the pose of the mobile device relative to the coordinate system of the vehicle and a pose of the vehicle relative to the event; and based on the pose of the mobile device relative to the event and the association of the location of the virtual content relative to the coordinate system of the mobile device with the location of the event relative to the coordinate system of the vehicle, determining that the virtual content at least partly occludes the event in a field-of-view of an occupant of the vehicle.

In some aspects, the process 1100 can include associating a location of a virtual content item relative to a coordinate system of the mobile device with a location of the event relative to the coordinate system of the vehicle; and filtering or modifying the virtual content item based on the association of the location of the virtual content relative to the coordinate system of the mobile device with the location of the event relative to the coordinate system of the vehicle.

In some examples, filtering or modifying the virtual content item can include modifying one or more characteristics of the virtual content item. In some cases, the one or more characteristics can include at least one of a transparency, a size, a location of the virtual content item, and a brightness level of the virtual content item.

In some examples, filtering or modifying the virtual content item can include determining an eye gaze of an occupant of the vehicle, the occupant being associated with the mobile device; determining a visibility of the event to the occupant based on the eye gaze of the occupant and the location of the event; and filtering or modifying the virtual content item further based on the visibility of the event to the occupant.

In some examples, the event can include at least one of a presence of an object within a path of the vehicle or a threshold proximity to the path of the vehicle, a traffic control associated with the path of the vehicle, and a failure by the vehicle to remain within at least one of a speed limit and a lane marking. In some cases, the object within the path of the vehicle or the threshold proximity to the path of the vehicle comprises at least one of a pedestrian, an animal, and another vehicle.

In some aspects, the process 1100 can include determining an eye gaze of an occupant of the vehicle, wherein the occupant is associated with the mobile device; and rendering virtual content within a direction of the eye gaze of the occupant of the vehicle.

In some cases, rendering the virtual content within the direction of the eye gaze of the occupant can include rendering a virtual content overlay including a virtual indicator of at least one of the event, a location of the event, and a direction of the event.

In some cases, rendering the virtual content within the direction of the eye gaze of the occupant can include modifying one or more characteristics of the virtual content. In some cases, the one or more characteristics can include at least one of a transparency, a size, a location of the virtual content, and a brightness level.

In some aspects, the process 1100 can include filtering, based on a context of the vehicle and the pose of the mobile device, at least a portion of the virtual content.

In some cases, filtering at least a portion of the virtual content can include enabling a presentation of a subset of the virtual content. In some examples, the subset of virtual content can include at least one of an indication of a status of the vehicle and vehicle instrumentation information.

In some aspects, displaying the virtual content can include rendering a virtual content item associated with the vehicle, the virtual content item being rendered relative to a surface of the vehicle.

In some cases, the rendered virtual content item can include at least one of a first indication of an event identified in the data associated with the one or more sensors, a second indication of a context of the vehicle, and an alert associated with the context of the vehicle.

In some aspects, rendering a virtual content item can include receiving a camera feed from a camera device of the vehicle; and displaying at least a portion of the camera feed within a display region of the mobile device.

In some cases, determining the pose of the mobile device can include obtaining one or more radio frequency (RF) signals; and determining the pose of the mobile device based on the one or more images and at least one of a round trip time associated with the one or more RF signals, a time of arrival associated with the one or more RF signals, and a received signal strength indicator (RSSI) associated with the one or more RF signals.

In some cases, determining the pose of the mobile device can include receiving, from the vehicle, a vehicle template that includes one or more markers associated with the vehicle; and determining the pose of the mobile device relative to the coordinate system of the vehicle based on the one or more images and the vehicle template.

In some examples, the one or more markers can include at least one of a visual pattern on at least one of an area within the interior portion of the vehicle and an object affixed to the interior portion of the vehicle, an element of the interior portion of the vehicle, a surface within the interior portion of the vehicle, and an illuminated object inside of the vehicle.

In some cases, determining the pose of the mobile device can include detecting the one or more markers in the one or more images; and determining the pose of the mobile device relative to the coordinate system of the vehicle based on the detected one or more markers and the vehicle template.

In some aspects, the process 1100 can include using one or more image sensors of the mobile device, a set of images of an interior portion of the vehicle, the set of images depicting one or more markers associated with the vehicle; and generating, based on the set of images, a vehicle template including the one or more markers.

Figure 12:
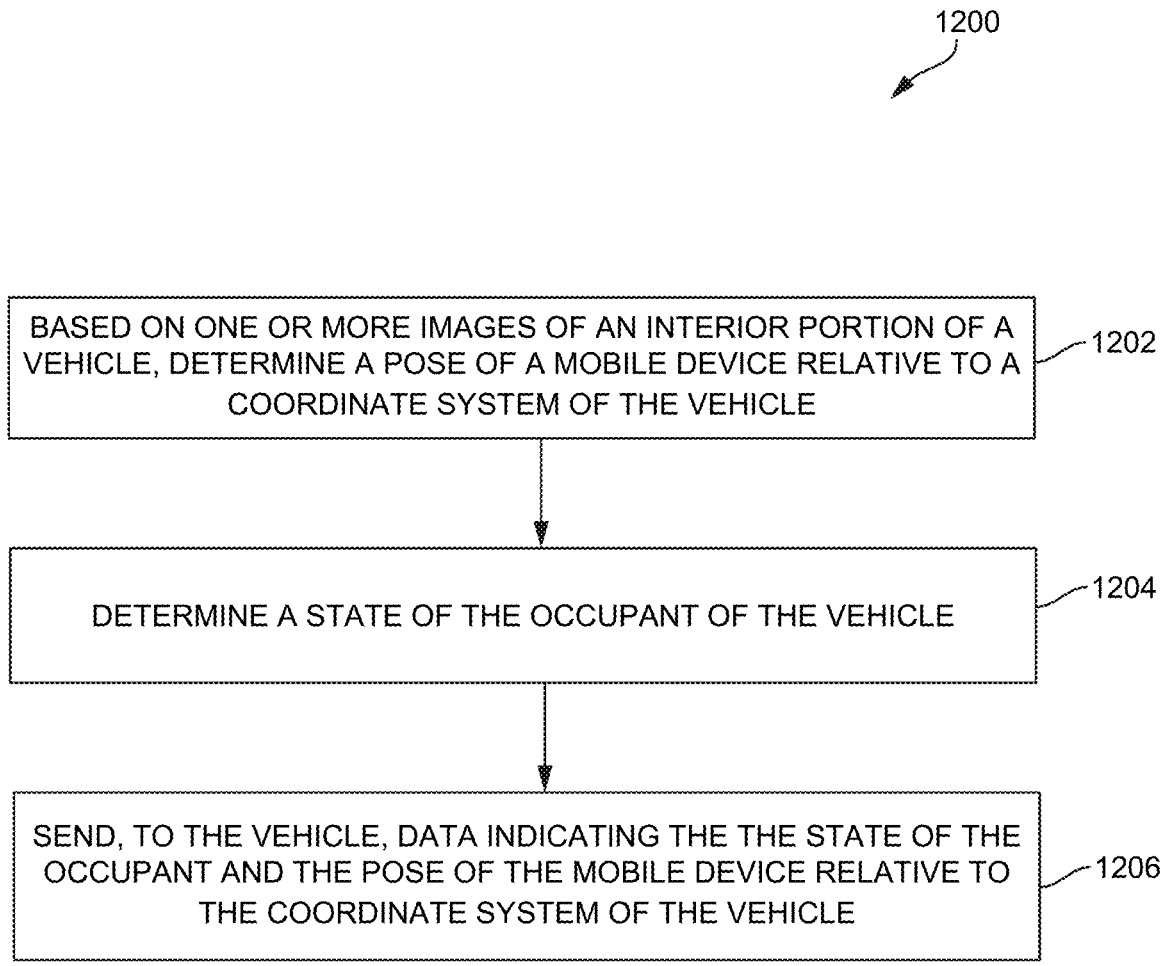
FIG. 12 is a flowchart illustrating an example process for monitoring an occupant of a vehicle, in accordance with some examples of the present disclosure.

FIG. 12 is a flowchart illustrating an example process 1200 for monitoring an occupant of a vehicle. At block 1202, the process 1200 can include determining, based on one or more images of an interior portion of a vehicle, a pose of a mobile device relative to a coordinate system of the vehicle. In some cases, the impairment can include at least one of a state of distraction with respect to at least one of an operation of the vehicle and an event associated with the vehicle, an intoxicated state, a health condition, a wakefulness state, a detected emotional state, an impaired position to control the vehicle, and an impaired view.

At block 1204, the process 1200 can include determining a state of an occupant of the vehicle. In some examples, the state of the occupant can include an impairment of the occupant with regard to operating the vehicle.

At block 1206, the process 1200 can include sending, to the vehicle, data indicating the state of the occupant and the pose of the mobile relative to the coordinate system of the vehicle.

In some examples, determining the state of the occupant can include receiving, from the vehicle, data associated with one or more sensors of the vehicle; and determining the state of the occupant based on the data associated with the one or more sensors of the vehicle and the pose of the mobile device.

In some cases, the data associated with the one or more sensors of the vehicle indicates at least one of a state of the vehicle and an event associated with the vehicle.

In some cases, the event associated with the vehicle can include at least one of a presence of an object within a path of the vehicle or a threshold proximity to the path of the vehicle, a traffic control associated with the path of the vehicle, and a failure by the vehicle to remain within at least one of a speed limit and a lane marking.

In some examples, the object within the path of the vehicle or the threshold proximity to the path of the vehicle can include at least one of a pedestrian, an animal, and another vehicle.

In some cases, the impairment of the occupant includes any event, activity, distraction, state, attribute, behavior, and/or condition that would negatively impact the occupant's ability to safely operate the vehicle.

In some aspects, the process 1200 can include determining an eye gaze of the occupant of the vehicle. In some cases, the state of the occupant can include the eye gaze of the occupant, and the occupant can be associated with the mobile device. For example, the occupant can be a user wearing the mobile device.

In some cases, determining the state of the occupant can include receiving, from one or more sensors associated with at least one of the mobile device and a wearable device worn by the occupant, one or more health measurements associated with the occupant; and determining the state of the occupant based on the one or more health measurements.

In some examples, the one or more health measurements can include at least one of a heart rate, a blood pressure, a body temperature, a galvanic skin response, a measurement of an electrical signal from a heart of the occupant, a measurement of electrical activity of a brain of the occupant, an amount of eye redness, and a pupil size.

In some cases, determining the state of the occupant can include determining that an eye gaze of the occupant is focused away from a road ahead of the vehicle for a period of time; and determining an impaired state of the occupant based on the eye gaze of the occupant being focused away from the road ahead of the vehicle for the period of time and a determination that the period of time exceeds a threshold period of time.

In some examples, determining that the eye gaze of the occupant is focused away from the road ahead of the vehicle for the period of time can include determining that the eye gaze of the occupant is focused on virtual content rendered by the mobile device for at least a portion of the period of time.

In some cases, determining that the eye gaze of the occupant is focused away from the road ahead of the vehicle for the period of time can include determining that the eye gaze of the occupant is focused in a different direction than a direction of an obstacle within a path of the vehicle or a threshold proximity to the path of the vehicle.

In some aspects, the process 1200 can include sending an indication of the state of the occupant to at least one of a second vehicle, a vehicle infrastructure system, a first remote device associated with a second occupant of the second vehicle, and a second remote device associated with a pedestrian.

In some cases, determining the state of the occupant can include determining an eye gaze of the occupant wearing the mobile device; and determining the state of the occupant based on the pose of the mobile device and the eye gaze of the occupant.

In some cases, determining the pose of the mobile device can include receiving, from the vehicle, a vehicle template that includes one or more markers associated with the vehicle; and determining the pose of the mobile device relative to the coordinate system of the vehicle based on the one or more images and the vehicle template.

In some cases, the one or more markers can include at least one of a visual pattern on at least one of an area within the interior portion of the vehicle and an object affixed to the interior portion of the vehicle, an element of the interior portion of the vehicle, a surface within the interior portion of the vehicle, and an illuminated object inside of the vehicle.

In some cases, the one or more images depict the one or more markers, and determining the pose of the mobile device can include detecting the one or more markers in the one or more images; and determining the pose of the mobile device relative to the coordinate system of the vehicle based on the detected one or more markers and the vehicle template.

In some aspects, the process 1200 can include obtaining, using one or more image sensors of the mobile device, a set of images of the interior portion of the vehicle, the set of images depicting one or more visual landmarks associated with the vehicle; and generating a vehicle template based on the set of images, the vehicle template including the one or more visual landmarks.

In some cases, determining the pose of the mobile device can include obtaining inertial sensor data associated with the mobile device; and determining the pose of the mobile device based on the one or more images and the inertial sensor data.

Figure 13:
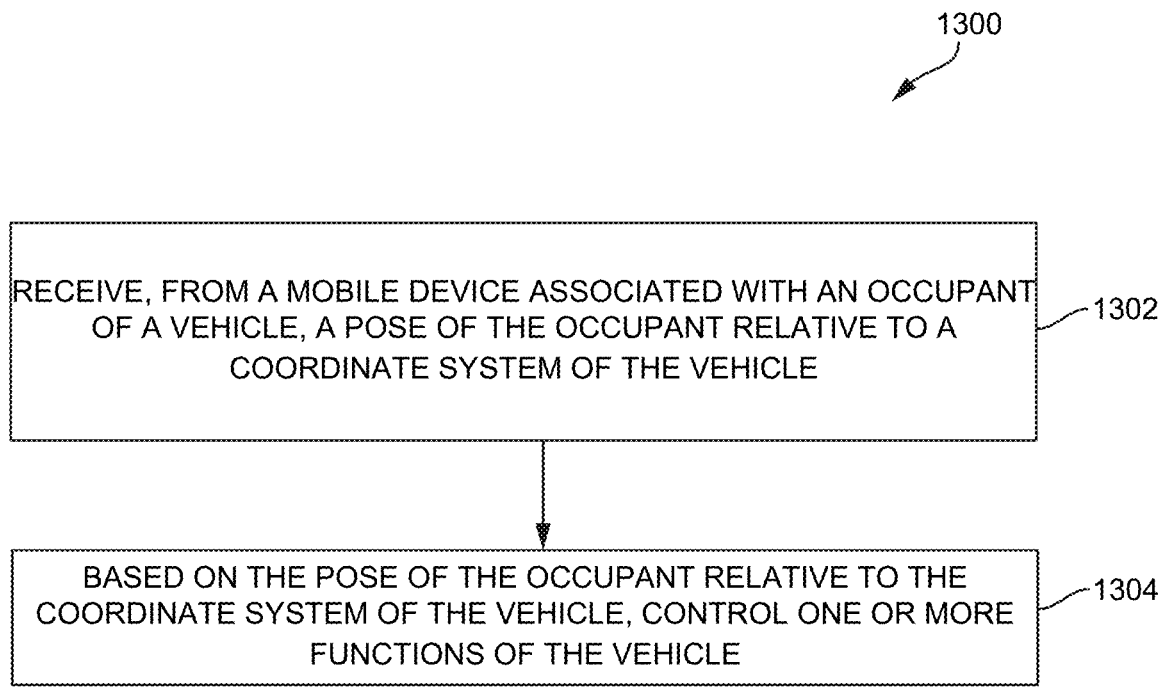
FIG. 13 is a flowchart illustrating an example process for controlling an operation of a vehicle, in accordance with some examples of the present disclosure.

FIG. 13 is a flowchart illustrating an example process 1300 for controlling an operation of a vehicle. At block 1302, the process 1300 can include receiving, from a mobile device associated with an occupant of a vehicle, a pose of the occupant relative to a coordinate system of the vehicle. At block 1304, the process 1300 can include controlling, based on the pose of the occupant relative to the coordinate system of the vehicle, one or more functions of the vehicle.

In some examples, controlling the one or more functions of the vehicle can include engaging one or more vehicle functions of the vehicle. In some examples, the one or more vehicle functions can include at least one of an autopilot function, a traction control function, a cruise control function, a collision avoidance function, a lane departure function, a lane centering function, a brake assist function, a lane-keeping function, a highway assist function, a lane change assistance function, a speed adaptation function, and an intersection assistance function.

In some examples, controlling the one or more functions of the vehicle can include controlling or engaging one or more autonomous vehicle systems of the vehicle. In some examples, the one or more autonomous vehicle systems can include at least one of a blind spot monitoring system, a driver monitoring system, a braking system, an autonomous driving control system, a driver assistance system, a navigation system, a steering control system, a vehicular communication system, and an automotive head-up display.

In some aspects, the process 1300 can include sending data associated with one or more sensors of the vehicle to at least one of the mobile device, a second vehicle, a vehicle infrastructure system, a first remote device associated with a second occupant of the second vehicle, and a second remote device associated with a pedestrian.

In some aspects, the process 1300 can include sending data indicating a state of the occupant to at least one of a second vehicle, a vehicle infrastructure system, a first remote device associated with a second occupant of the second vehicle, and a second remote device associated with a pedestrian.

In some aspects, the process 1300 can include sending, to the mobile device, a vehicle template for determining the pose of the occupant relative to the coordinate system of the vehicle, the vehicle template including one or more markers associated with the vehicle.

In some examples, the one or more markers can include at least one of a visual pattern on at least one of an area within an interior portion of the vehicle and an object affixed to the interior portion of the vehicle, an element of the interior portion of the vehicle, a surface within the interior portion of the vehicle, and an illuminated object inside of the vehicle.

In some aspects, the process 1300 can include generating an output based at least partly on the pose of the occupant relative to the coordinate system of the vehicle. In some examples, the output can include at least one of a communication to the mobile device, an instruction to modify the one or more functions of the vehicle, and an indication of a state of the occupant.

In some cases, the communication to the mobile device can include at least one of a virtual content item and a request to display the virtual content item.

In some aspects, the process 1300 can include receiving, from the mobile device, data indicating a state of the occupant of the vehicle. In some cases, the data can include at least one of sensor data from one or more sensors of the mobile device and processed data generated based on the sensor data from the one or more sensors of the mobile device.

In some cases, the processed data can include at least one of a description of the state of the occupant and a classification output identifying the state of the occupant.

In some aspects, the process 1300 can include receiving, from the mobile device, data indicating a state of the occupant of the vehicle. In some cases, the data can include at least one of an indication of an eye gaze of the occupant, the pose of the method relative to the coordinate system of the vehicle, and one or more health measurements associated with the occupant.

In some cases, the one or more health measurements can include at least one of a heart rate, a blood pressure, a body temperature, a galvanic skin response, a measurement of an electrical signal from a heart of the occupant, a measurement of electrical activity of a brain of the occupant, an amount of eye redness, and a pupil size.

In some aspects, the process 1300 can include obtaining, from one or more sensors of the vehicle, sensor data including at least one of an indication of an event related to an operation of the vehicle, an indication of one or more driving patterns during one or more operations of the vehicle controlled at least partly by the occupant, and vehicle instrumentation data. In some cases, the process 1300 can include controlling the one or more functions of the vehicle further based on the sensor data.

In some aspects, the process 1300 can include determining a state of the occupant. In some cases, determining the state of the occupant can include receiving, from one or more health sensors associated with at least one of the mobile device and a wearable device, one or more health measurements associated with the occupant; and determine the state of the occupant based on the one or more health measurements associated with the occupant.

In some aspects, the process 1300 can include obtaining a state of the occupant. In some examples, the state of the occupant can include an impairment of the occupant with regard to operating the vehicle. In some examples, the impairment of the occupant can include a transient impairment of the occupant. In some cases, the impairment can include at least one of a state of distraction with respect to at least one of an operation of the vehicle and an event associated with the vehicle, an intoxicated state, a health condition, a wakefulness state, a detected emotional state, an impaired position to control the vehicle, and an impaired view. In some cases, the impairment of the occupant includes any event, activity, distraction, state, attribute, behavior, and/or condition that would negatively impact the occupant's ability to safely operate the vehicle.

In some examples, the event can include at least one of a presence of an object within a path of the vehicle or a threshold proximity to the path of the vehicle, a traffic control associated with the path of the vehicle, and a failure by the vehicle to remain within at least one of a speed limit and a lane marking. In some examples, the object can include at least one of a pedestrian, an animal, and another vehicle.

In some aspects, the process 1300 can include obtaining one or more images of an interior portion of the vehicle, the one or more images depicting one or more visual landmarks associated with the vehicle; and generating a vehicle template based on the one or more images, the vehicle template describing the one or more visual landmarks.

In some aspects, the process 1300 can include sending the vehicle template to the mobile device; and receiving, from the mobile device, the pose of the occupant relative to one or more coordinates defined in the vehicle template. In some examples, the one or more coordinates are relative to the one or more visual landmarks and correspond to the coordinate system of the vehicle.

In some aspects, the process 1300 can include receiving, from the mobile device, data indicating a state of the occupant. In some cases, controlling one or more functions of the vehicle can include controlling one or more functions of the vehicle based on the pose of the occupant and the data indicating the state of the occupant.

In some aspects, the process 1300 can include generating an output based at least partly on the pose of the occupant relative to the coordinate system of the vehicle. In some examples, the output can include at least one of an instruction to modify the one or more functions of the vehicle and an updated state of the occupant.

In some examples, the one or more functions of the vehicle can be controlled via a computer system of the vehicle configured to control at least one of the one or more functions of the vehicle and one or more autonomous vehicle systems of the vehicle.

Figure 14:
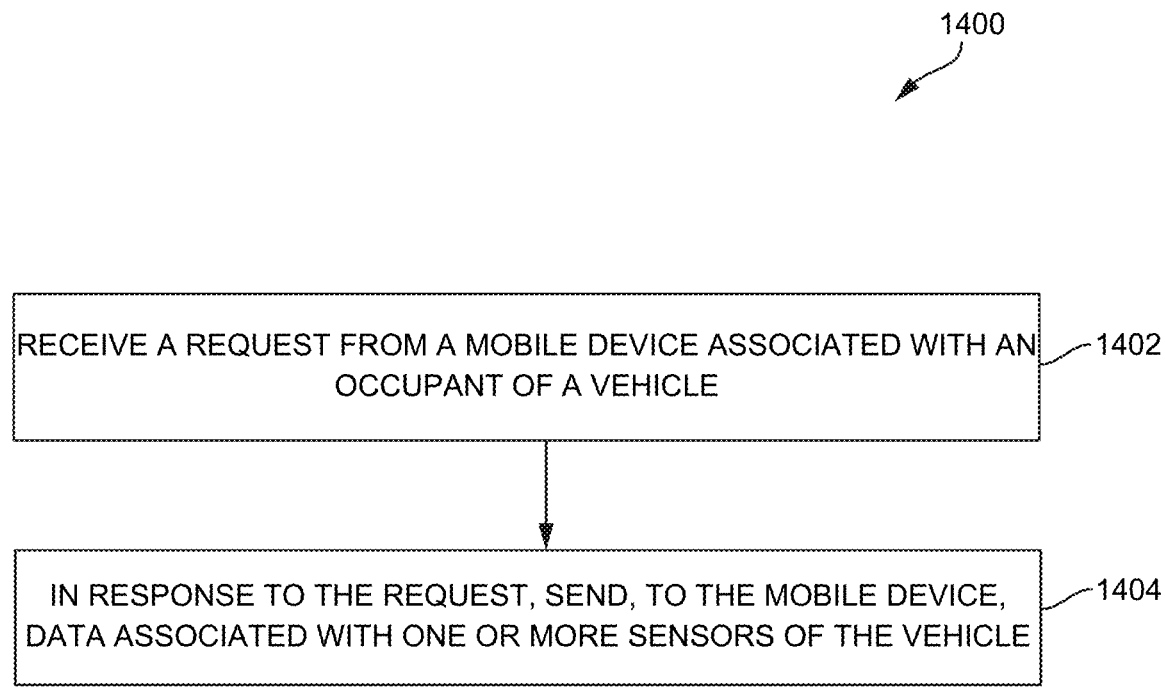
FIG. 14 is a flowchart illustrating an example process for interfacing a vehicle with a mobile device associated with an occupant of the vehicle, in accordance with some examples of the present disclosure.

FIG. 14 is a flowchart illustrating an example process 1300 for interfacing a vehicle with a mobile device associated with an occupant of the vehicle. At block 1402, the process 1400 can include receiving a request from an augmented reality (AR) device connected with a computer system of a vehicle. In some examples, the request can request data generated and/or obtained by the vehicle such as, for example, data from one or more sensors of the vehicle.

At block 1404, the process 1400 can include, in response to the request, sending, to the AR device, data associated with one or more sensors of the vehicle. In some examples, the data can include vehicle data indicating a context of the vehicle. In some examples, the context of the vehicle can include at least one of a state of the vehicle and one or more events encountered by the vehicle or determined to occur during one or more operations of the vehicle.

In some examples, the one or more events can include at least one of a presence of an object within a path of the vehicle or a threshold proximity to the path of the vehicle, a traffic control associated with the path of the vehicle, and a failure by the vehicle to remain within at least one of a speed limit and a lane marking. In some cases, the object within the path of the vehicle or the threshold proximity to the path of the vehicle can include at least one of a pedestrian, an animal, and another vehicle.

In some aspects, the process 1400 can include sending, to the AR device, display data for presentation at a location relative to at least one of a pose of the AR device relative to a coordinate system of the vehicle and a respective location of the one or more events. In some examples, the display data can include at least a portion of the vehicle data.

In some aspects, the process 1400 can include sending, to the AR device, an indication of the respective location of the one or more events. In some aspects, the process 1400 can include sending, to the AR device, a vehicle template for determining a pose of the AR device relative to a coordinate system of the vehicle. In some examples, the vehicle template can describe one or more markers in an interior portion of the vehicle.

In some examples, the one or more markers can include at least one of a visual pattern on at least one of an area within the interior portion of the vehicle and an object affixed to the interior portion of the vehicle, an element of the interior portion of the vehicle, a surface within the interior portion of the vehicle, and an illuminated object inside of the vehicle.

In some aspects, the process 1400 can include receiving, from the AR device, the pose of the AR device relative to the coordinate system of the vehicle.

In some aspects, the process 1400 can include controlling, based on at least one of the data associated with the one or more sensors and the pose of the AR device relative to the coordinate system of the vehicle, a presentation by the computer system of virtual content associated with the vehicle. In some cases, controlling the presentation of virtual content can include based on the pose of the AR device relative to the coordinate system of the vehicle, providing, to the AR device, a live content feed from one or more image sensors of the vehicle.

In some cases, providing the live content feed can include determining a pose of the AR device relative to the vehicle event based on the pose of the AR device relative to the coordinate system of the vehicle and a position of the vehicle relative to the vehicle event; and based on the pose of the AR device relative to the vehicle event, determining that virtual content associated with at least one of the computer system and the AR device at least partly occludes the vehicle event in a field-of-view of the AR device.

In some examples, controlling the presentation of virtual content can include associating a location of a virtual content item rendered by the computer system with a location of the vehicle event relative to the coordinate system of the vehicle; and filtering or modifying the virtual content item based on the association of the location of the virtual content with the location of the vehicle event relative to the coordinate system of the vehicle.

In some cases, filtering or modifying the virtual content item can include modifying one or more characteristics of the virtual content item. In some examples, the one or more characteristics can include at least one of a transparency, a size, a location of the virtual content item, and a brightness level.

In some examples, filtering or modifying the virtual content item can include receiving an eye gaze of the occupant of the vehicle; determining a visibility of the vehicle event to the occupant based on the eye gaze of the occupant and the location of the vehicle event; and filtering or modifying the virtual content item further based on the visibility of the vehicle event to the occupant.

In some cases, controlling the presentation of virtual content can include receiving an eye gaze of the occupant of the vehicle; and rendering virtual content within a direction of the eye gaze of the occupant of the vehicle.

In some examples, rendering the virtual content can include rendering a virtual content overlay comprising a virtual indicator of at least one of a vehicle event, a location of the vehicle event, and a direction of the vehicle event.

In some cases, rendering the virtual content can include modifying one or more characteristics of the virtual content. In some examples, the one or more characteristics can include at least one of a transparency, a size, a location of the virtual content, and a brightness level.

In some aspects, the process 1400 can include sending, to one or more display devices, an instruction to display, a virtual content item that provides information about an operation of the vehicle. In some cases, the instruction can indicate a placement of the virtual content item relative to a location in the vehicle that is within a field-of-view of the occupant.

In some examples, the virtual content item can include at least one of a first indication of a vehicle event detected by the computer system, a second indication of a context of the vehicle, and an alert associated with the context of the vehicle.

In some aspects, the process 1400 can include receiving a camera feed from a camera device on the vehicle; and sending, to the AR device, at least a portion of the camera feed for display.

In some aspects, the process 1400 can include sending, to the AR device, an indication of a state of the occupant. In some examples, the state of the occupant can include an impairment of the occupant with regard to operating the vehicle. In some examples, the impairment can include a transient impairment. In some cases, the impairment can include at least one of a state of distraction with respect to at least one of an operation of the vehicle and an event associated with the vehicle, an intoxicated state, a health condition, a wakefulness state, a detected emotional state, an impaired position to control the vehicle, and an impaired view.

In some aspects, the process 1400 can include controlling an operation of the vehicle based on the impairment of the occupant. In some examples, the impairment of the occupant includes any event, activity, distraction, state, attribute, behavior, and/or condition that would negatively impact the occupant's ability to safely operate the vehicle.

In some aspects, the process 1400 can include generating display data based on the impairment of the occupant. In some examples, the display data can include at least one of a vehicle event and vehicle instrumentation data.

In some aspects, the process 1400 can include sending, to the AR device, display data based on the impairment of the occupant. In some examples, the display data can include at least one of a vehicle event and vehicle instrumentation data.

In some examples, the computer system is configured to control at least one of one or more autonomous functions of the vehicle and one or more autonomous vehicle systems of the vehicle.

In some examples, the AR device can include a head-mounted display. In some examples, the AR device can include a wearable AR device.

In some examples, any of the processes 1100, 1200, 1300, and/or 1400 may be performed by one or more computing devices or apparatuses. In one illustrative example, any of the processes 1100, 1200, 1300, and/or 1400 can be performed by the mobile device 150 shown in FIG. 1 and/or the vehicle 202 (and/or the vehicle computing system 210) shown in FIG. 2. In some examples, any of the processes 1100, 1200, 1300, and/or 1400 can be performed by one or more computing devices with the computing device architecture 1500 shown in FIG. 15. In some cases, such a computing device or apparatus may include a processor, microprocessor, microcomputer, or other component of a device that is configured to carry out the steps of any of the processes 1100, 1200, 1300, and/or 1400. In some examples, such computing device or apparatus may include one or more sensors configured to capture image data and/or other sensor measurements. For example, the computing device can include a smartphone, a head-mounted display, a mobile device, or other suitable device. In some examples, such computing device or apparatus may include a camera configured to capture one or more images or videos. In some cases, such computing device may include a display for displaying images. In some examples, the one or more sensors and/or camera are separate from the computing device, in which case the computing device receives the sensed data. Such computing device may further include a network interface configured to communicate data.

The components of the computing device can be implemented in circuitry. For example, the components can include and/or can be implemented using electronic circuits or other electronic hardware, which can include one or more programmable electronic circuits (e.g., microprocessors, graphics processing units (GPUs), digital signal processors (DSPs), central processing units (CPUs), and/or other suitable electronic circuits), and/or can include and/or be implemented using computer software, firmware, or any combination thereof, to perform the various operations described herein. The computing device may further include a display (as an example of the output device or in addition to the output device), a network interface configured to communicate and/or receive the data, any combination thereof, and/or other component(s). The network interface may be configured to communicate and/or receive Internet Protocol (IP) based data or other type of data.

The processes 1100, 1200, 1300, and 1400 are illustrated as logical flow diagrams, the operations of which represent sequences of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

Additionally, any of the processes 1100, 1200, 1300, and/or 1400 may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable or machine-readable storage medium, for example, in the form of a computer program comprising a plurality of instructions executable by one or more processors. The computer-readable or machine-readable storage medium may be non-transitory.

Figure 15:
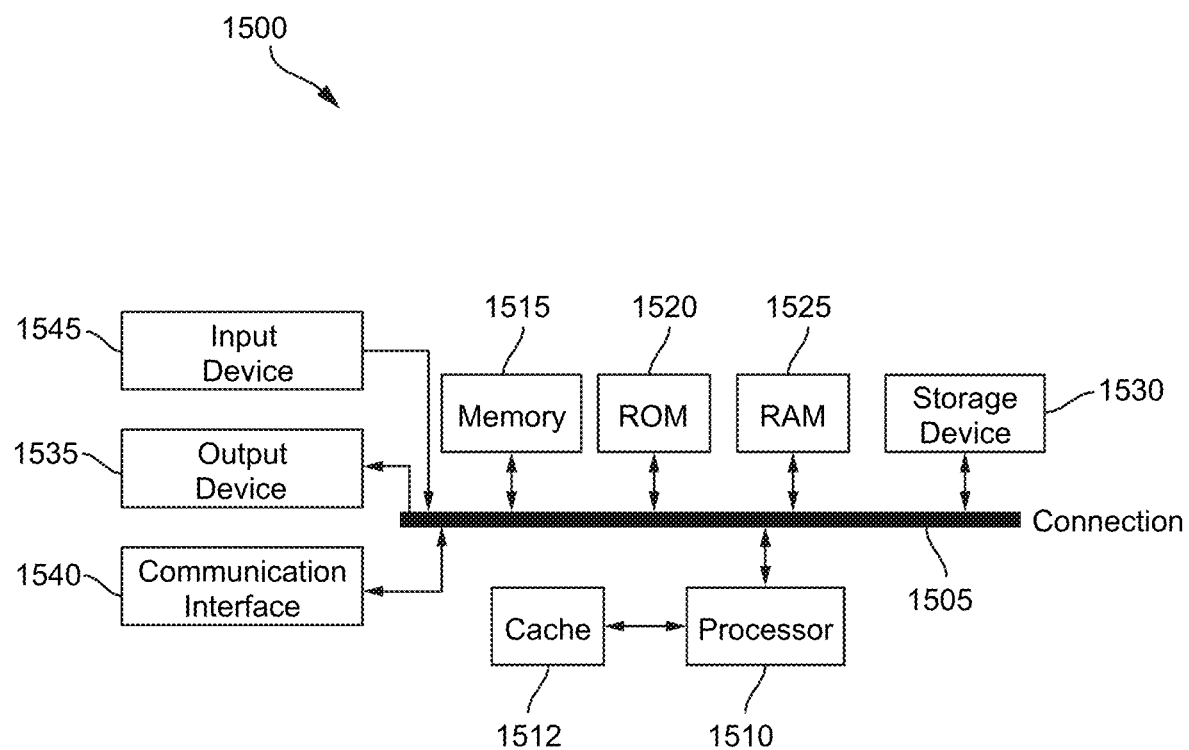
FIG. 15 illustrates an example computing device architecture, in accordance with some examples of the present disclosure.

FIG. 15 illustrates an example computing device architecture 1500 of an example computing device which can implement various techniques described herein. For example, the computing device architecture 1500 can implement at least some portions of the computing system 100 shown in FIG. 1 or the computing system 210 shown in FIG. 2. The components of the computing device architecture 1500 are shown in electrical communication with each other using a connection 1505, such as a bus. The example computing device architecture 1500 includes a processing unit (CPU or processor) 1510 and a computing device connection 1505 that couples various computing device components including the computing device memory 1515, such as read only memory (ROM) 1520 and random access memory (RAM) 1525, to the processor 1510.

The computing device architecture 1500 can include a cache of high-speed memory connected directly with, in close proximity to, or integrated as part of the processor 1510. The computing device architecture 1500 can copy data from the memory 1515 and/or the storage device 1530 to the cache 1512 for quick access by the processor 1510. In this way, the cache can provide a performance boost that avoids processor 1510 delays while waiting for data. These and other modules can control or be configured to control the processor 1510 to perform various actions. Other computing device memory 1515 may be available for use as well. The memory 1515 can include multiple different types of memory with different performance characteristics. The processor 1510 can include any general-purpose processor and a hardware or software service stored in storage device 1530 and configured to control the processor 1510 as well as a special-purpose processor where software instructions are incorporated into the processor design. The processor 1510 may be a self-contained system, containing multiple cores or processors, a bus, memory controller, cache, etc. A multi-core processor may be symmetric or asymmetric.

To enable user interaction with the computing device architecture 1500, an input device 1545 can represent any number of input mechanisms, such as a microphone for speech, a touch-sensitive screen for gesture or graphical input, keyboard, mouse, motion input, speech and so forth. An output device 1535 can also be one or more of a number of output mechanisms known to those of skill in the art, such as a display, projector, television, speaker device. In some instances, multimodal computing devices can enable a user to provide multiple types of input to communicate with the computing device architecture 1500. The communication interface 1540 can generally govern and manage the user input and computing device output. There is no restriction on operating on any particular hardware arrangement and therefore the basic features here may easily be substituted for improved hardware or firmware arrangements as they are developed.

Storage device 1530 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1525, read only memory (ROM) 1520, and hybrids thereof. The storage device 1530 can include software, code, firmware, etc., for controlling the processor 1510. Other hardware or software modules are contemplated. The storage device 1530 can be connected to the computing device connection 1505. In one aspect, a hardware module that performs a particular function can include the software component stored in a computer-readable medium in connection with the necessary hardware components, such as the processor 1510, connection 1505, output device 1535, and so forth, to carry out the function.

The term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Specific details are provided in the description above to provide a thorough understanding of the embodiments and examples provided herein. However, it will be understood by one of ordinary skill in the art that the embodiments may be practiced without these specific details. For clarity of explanation, in some instances the present technology may be presented as including individual functional blocks comprising devices, device components, steps or routines in a method embodied in software, or combinations of hardware and software. Additional components may be used other than those shown in the figures and/or described herein. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Individual embodiments may be described above as a process or method which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

Processes and methods according to the above-described examples can be implemented using computer-executable instructions that are stored or otherwise available from computer-readable media. Such instructions can include, for example, instructions and data which cause or otherwise configure a general-purpose computer, special purpose computer, or a processing device to perform a certain function or group of functions. Portions of computer resources used can be accessible over a network. The computer executable instructions may be, for example, binaries, intermediate format instructions such as assembly language, firmware, source code. Examples of computer-readable media that may be used to store instructions, information used, and/or information created during methods according to described examples include magnetic or optical disks, flash memory, USB devices provided with non-volatile memory, networked storage devices, and so on.

Devices implementing processes and methods according to these disclosures can include hardware, software, firmware, middleware, microcode, hardware description languages, or any combination thereof, and can take any of a variety of form factors. When implemented in software, firmware, middleware, or microcode, the program code or code segments to perform the necessary tasks (e.g., a computer-program product) may be stored in a computer-readable or machine-readable medium. A processor(s) may perform the necessary tasks. Typical examples of form factors include laptops, smart phones, mobile phones, tablet devices or other small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are example means for providing the functions described in the disclosure.

In the foregoing description, aspects of the application are described with reference to specific embodiments thereof, but those skilled in the art will recognize that the application is not limited thereto. Thus, while illustrative embodiments of the application have been described in detail herein, it is to be understood that the inventive concepts may be otherwise variously embodied and employed, and that the appended claims are intended to be construed to include such variations, except as limited by the prior art. Various features and aspects of the above-described application may be used individually or jointly. Further, embodiments can be utilized in any number of environments and applications beyond those described herein without departing from the broader scope of the specification. The specification and drawings are, accordingly, to be regarded as illustrative rather than restrictive. For the purposes of illustration, methods were described in a particular order. It should be appreciated that in alternate embodiments, the methods may be performed in a different order than that described.

One of ordinary skill will appreciate that the less than ("<") and greater than (">") symbols or terminology used herein can be replaced with less than or equal to ("≤") and greater than or equal to ("≥") symbols, respectively, without departing from the scope of this description.

Where components are described as being "configured to" perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

The phrase "coupled to" refers to any component that is physically connected to another component either directly or indirectly, and/or any component that is in communication with another component (e.g., connected to the other component over a wired or wireless connection, and/or other suitable communication interface) either directly or indirectly.

Claim language or other language in the disclosure reciting "at least one of" a set and/or "one or more" of a set indicates that one member of the set or multiple members of the set (in any combination) satisfy the claim. For example, claim language reciting "at least one of A and B" or "at least one of A or B" means A, B, or A and B. In another example, claim language reciting "at least one of A, B, and C" or "at least one of A, B, or C" means A, B, C, or A and B, or A and C, or B and C, or A and B and C. The language "at least one of" a set and/or "one or more" of a set does not limit the set to the items listed in the set. For example, claim language reciting "at least one of A and B" or "at least one of A or B" can mean A, B, or A and B, and can additionally include items not listed in the set of A and B.

The various illustrative logical blocks, modules, circuits, and algorithm steps described in connection with the examples disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present application.

The techniques described herein may also be implemented in electronic hardware, computer software, firmware, or any combination thereof. Such techniques may be implemented in any of a variety of devices such as general purposes computers, wireless communication device handsets, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods, algorithms, and/or operations described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general-purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein.

Illustrative examples of the disclosure include:

Aspect 1. An apparatus comprising: memory; and one or more processors coupled to the memory, the one or more processors being configured to: determine a pose of the apparatus relative to a coordinate system of the vehicle; receive, from the vehicle, data associated with one or more sensors of the vehicle; and display, using a display device of the apparatus, virtual content based on the data associated with the one or more sensors and the pose of the apparatus relative to the coordinate system of the vehicle.

Aspect 2. The apparatus of Aspect 1, wherein, to determine the pose of the apparatus, the one or more processors are configured to determine the pose of the apparatus based on one or more images of an interior portion of a vehicle.

Aspect 3. The apparatus of any of Aspects 1 to 2, wherein the one or more processors are configured to determine a context of the vehicle based on the data associated with the one or more sensors, wherein the context comprises an event related to the vehicle.

Aspect 4. The apparatus Aspect 3, wherein the one or more processors are further configured to: filter or modify a virtual content item that would distract an occupant of the vehicle from an operation of the vehicle or a vehicle event, or would obstruct a view of the occupant to the vehicle event or a region outside of the vehicle that is determined as non-coverable.

Aspect 5. The apparatus of any of Aspects 3 to 4, wherein the one or more processors are configured to: associate a location of the virtual content relative to a coordinate system of the apparatus with a location of the event relative to the coordinate system of the vehicle; and based on the association of the location of the virtual content relative to the coordinate system of the apparatus with the location of the event relative to the coordinate system of the vehicle, display a live content feed from one or more visual image sensors of the apparatus.

Aspect 6. The apparatus of Aspect 5, wherein, to display the live content feed, the one or more processors are configured to: determine a pose of the apparatus relative to the event based on the pose of the apparatus relative to the coordinate system of the vehicle and a pose of the vehicle relative to the event; and based on the pose of the apparatus relative to the event and the association of the location of the virtual content relative to the coordinate system of the apparatus with the location of the event relative to the coordinate system of the vehicle, determine that the virtual content at least partly occludes the event in a field-of-view of an occupant of the vehicle.

Aspect 7. The apparatus of Aspect 5, wherein the one or more processors are configured to display the live content based further on a determination that the virtual content at least partly obstructs a view of one or more image sensors of the apparatus to the event.

Aspect 8. The apparatus of any of Aspects 3 to 7, wherein the one or more processors are configured to: associate a location of a virtual content item relative to a coordinate system of the apparatus with a location of the event relative to the coordinate system of the vehicle; and filter or modify the virtual content item based on the association of the location of the virtual content relative to the coordinate system of the apparatus with the location of the event relative to the coordinate system of the vehicle.

Aspect 9. The apparatus of Aspect 8, wherein, to filter or modify the virtual content item, the one or more processors are configured to: modify one or more characteristics of the virtual content item, the one or more characteristics comprising at least one of a transparency, a size, a location of the virtual content item, and a brightness level of the virtual content item.

Aspect 10. The apparatus of any of Aspects 8 to 9, wherein, to filter or modify the virtual content item, the one or more processors are configured to: determine an eye gaze of an occupant of the vehicle, the occupant being associated with the apparatus; determine a visibility of the event to the occupant based on the eye gaze of the occupant and the location of the event; and filter or modify the virtual content item further based on the visibility of the event to the occupant.

Aspect 11. The apparatus of Aspect 3, wherein the event comprises at least one of a presence of an object within a path of the vehicle or a threshold proximity to the path of the vehicle, a traffic control associated with the path of the vehicle, and a failure by the vehicle to remain within at least one of a speed limit and a lane marking.

Aspect 12. The apparatus of Aspect 11, wherein the object within the path of the vehicle or the threshold proximity to the path of the vehicle comprises at least one of a pedestrian, an animal, and another vehicle.

Aspect 13. The apparatus of Aspect 3, wherein the one or more processors are configured to: determine an eye gaze of an occupant of the vehicle, wherein the occupant is associated with the apparatus; and render virtual content within a direction of the eye gaze of the occupant of the vehicle.

Aspect 14. The apparatus of Aspect 13, wherein, to render the virtual content within the direction of the eye gaze of the occupant, the one or more processors are configured to: render a virtual content overlay comprising a virtual indicator of at least one of the event, a location of the event, and a direction of the event.

Aspect 15. The apparatus of any of Aspects 13 to 14, wherein, to render the virtual content within the direction of the eye gaze of the occupant, the one or more processors are configured to: modify one or more characteristics of the virtual content, the one or more characteristics comprising at least one of a transparency, a size, a location of the virtual content, and a brightness level.

Aspect 16. The apparatus of any of Aspects 1 to 15, wherein the one or more processors are configured to: filter, based on a context of the vehicle and the pose of the apparatus, at least a portion of the virtual content.

Aspect 17. The apparatus of Aspect 16, wherein, to filter at least a portion of the virtual content, the one or more processors are configured to enable a presentation of a subset of the virtual content, the subset of virtual content comprising at least one of an indication of a status of the vehicle and vehicle instrumentation information.

Aspect 18. The apparatus of any of Aspects 1 to 17, wherein, to display the virtual content, the one or more processors are configured to render a virtual content item associated with the vehicle, the virtual content item being rendered relative to a surface of the vehicle.

Aspect 19. The apparatus of Aspect 18, wherein the rendered virtual content item comprises at least one of a first indication of an event identified in the data associated with the one or more sensors, a second indication of a context of the vehicle, and an alert associated with the context of the vehicle.

Aspect 20. The apparatus of any of Aspects 18 to 19, wherein, to render a virtual content item, the one or more processors are configured to: receive a camera feed from a camera device of the vehicle; and display at least a portion of the camera feed within a display region of the apparatus.

Aspect 21. The apparatus of any of Aspects 1 to 20, wherein, to determine the pose of the apparatus, the one or more processors are configured to: obtain one or more radio frequency (RF) signals; and determine the pose of the apparatus based on one or more images of an interior portion of the vehicle and at least one of a round trip time associated with the one or more RF signals, a time of arrival associated with the one or more RF signals, and a received signal strength indicator (RSSI) associated with the one or more RF signals.

Aspect 22. The apparatus of any of Aspects 1 to 21, wherein, to determine the pose of the apparatus, the one or more processors are configured to: receive, from the vehicle, a vehicle template that includes one or more markers associated with the vehicle; and determine the pose of the apparatus relative to the coordinate system of the vehicle based on one or more images of an interior portion of the vehicle and the vehicle template.

Aspect 23. The apparatus of Aspect 22, wherein the one or more markers comprise at least one of a visual pattern on at least one of an area within an interior portion of the vehicle and an object affixed to the interior portion of the vehicle, an element of the interior portion of the vehicle, a surface within the interior portion of the vehicle, and an illuminated object inside of the vehicle.

Aspect 24. The apparatus of any of Aspects 22 to 23, wherein, to determine the pose of the apparatus, the one or more processors are configured to: detect the one or more markers in the one or more images; and determine the pose of the apparatus relative to the coordinate system of the vehicle based on the detected one or more markers and the vehicle template.

Aspect 25. The apparatus of any of Aspects 1 to 24, wherein the one or more processors are configured to: obtain, using one or more image sensors of the apparatus, a set of images of an interior portion of the vehicle, the set of images depicting one or more markers associated with the vehicle; and generate, based on the set of images, a vehicle template including the one or more markers.

Aspect 26. The apparatus of any of Aspects 1 to 25, wherein the apparatus comprises a head-mounted display.

Aspect 27. The apparatus of any of Aspects 1 to 26, further comprising one or more image sensors.

Aspect 28. A method comprising: determining a pose of a mobile device relative to a coordinate system of a vehicle; receiving, from the vehicle, data associated with one or more sensors of the vehicle; and displaying, using a display device of the mobile device, virtual content based on the data associated with the one or more sensors and the pose of the mobile device relative to the coordinate system of the vehicle.

Aspect 29. The method of Aspect 28, wherein determining the pose of the mobile device comprises determining the pose of the mobile device based on one or more images of an interior portion of the vehicle.

Aspect 30. The method of any of Aspects 28 to 29, further comprising determining a context of the vehicle based on the data associated with the one or more sensors, wherein the context comprises an event related to the vehicle.

Aspect 31. The method of Aspect 30, further comprising: filtering or modifying a virtual content item that would distract an occupant of the vehicle from an operation of the vehicle or a vehicle event, or would obstruct a view of the occupant to the vehicle event or a region outside of the vehicle that is determined as non-coverable.

Aspect 32. The method of any of Aspects 30 to 31, further comprising: associating a location of the virtual content relative to a coordinate system of the mobile device with a location of the event relative to the coordinate system of the vehicle; and based on the association of the location of the virtual content relative to the coordinate system of the mobile device with the location of the event relative to the coordinate system of the vehicle, displaying a live content feed from one or more visual image sensors of the mobile device.

Aspect 33. The method of Aspect 32, wherein displaying the live content feed comprises: determining a pose of the mobile device relative to the event based on the pose of the mobile device relative to the coordinate system of the vehicle and a pose of the vehicle relative to the event; and based on the pose of the mobile device relative to the event and the association of the location of the virtual content relative to the coordinate system of the mobile device with the location of the event relative to the coordinate system of the vehicle, determining that the virtual content at least partly occludes the event in a field-of-view of an occupant of the vehicle.

Aspect 34. The method of any of Aspects 32 to 33, further comprising displaying the live content based further on a determination that the virtual content at least partly obstructs a view of one or more image sensors of the mobile device to the event.

Aspect 35. The method of Aspect 30, further comprising: associating a location of a virtual content item relative to a coordinate system of the mobile device with a location of the event relative to the coordinate system of the vehicle; and filtering or modifying the virtual content item based on the association of the location of the virtual content relative to the coordinate system of the mobile device with the location of the event relative to the coordinate system of the vehicle.

Aspect 36. The method of Aspect 35, wherein, to filter or modify the virtual content item, the one or more processors are configured to: modifying one or more characteristics of the virtual content item, the one or more characteristics comprising at least one of a transparency, a size, a location of the virtual content item, and a brightness level of the virtual content item.

Aspect 37. The method of any of Aspects 35 to 36, wherein, to filter or modify the virtual content item, the one or more processors are configured to: determining an eye gaze of an occupant of the vehicle, the occupant being associated with the mobile device; determining a visibility of the event to the occupant based on the eye gaze of the occupant and the location of the event; and filtering or modifying the virtual content item further based on the visibility of the event to the occupant.

Aspect 38. The method of Aspect 30, wherein the event comprises at least one of a presence of an object within a path of the vehicle or a threshold proximity to the path of the vehicle, a traffic control associated with the path of the vehicle, and a failure by the vehicle to remain within at least one of a speed limit and a lane marking.

Aspect 39. The method of Aspect 38, wherein the object within the path of the vehicle or the threshold proximity to the path of the vehicle comprises at least one of a pedestrian, an animal, and another vehicle.

Aspect 40. The method of Aspect 30, further comprising: determining an eye gaze of an occupant of the vehicle, wherein the occupant is associated with the mobile device; and rendering virtual content within a direction of the eye gaze of the occupant of the vehicle.

Aspect 41. The method of Aspect 40, wherein rendering the virtual content within the direction of the eye gaze of the occupant comprises: rendering a virtual content overlay comprising a virtual indicator of at least one of the event, a location of the event, and a direction of the event.

Aspect 42. The method of any of Aspects 40 to 41, wherein, to render the virtual content within the direction of the eye gaze of the occupant, the one or more processors are configured to: modifying one or more characteristics of the virtual content, the one or more characteristics comprising at least one of a transparency, a size, a location of the virtual content, and a brightness level.

Aspect 43. The method of any of Aspects 28 to 42, further comprising: filtering, based on a context of the vehicle and the pose of the mobile device, at least a portion of the virtual content.

Aspect 44. The method of Aspect 43, wherein filtering at least a portion of the virtual content comprises enabling a presentation of a subset of the virtual content, the subset of virtual content comprising at least one of an indication of a status of the vehicle and vehicle instrumentation information.

Aspect 45. The method of any of Aspects 28 to 44, wherein displaying the virtual content comprises rendering a virtual content item associated with the vehicle, the virtual content item being rendered relative to a surface of the vehicle.

Aspect 46. The method of Aspect 45, wherein the rendered virtual content item comprises at least one of a first indication of an event identified in the data associated with the one or more sensors, a second indication of a context of the vehicle, and an alert associated with the context of the vehicle.

Aspect 47. The method of any of Aspects 45 to 46, wherein rendering a virtual content item comprises: receiving a camera feed from a camera device of the vehicle; and displaying at least a portion of the camera feed within a display region of the mobile device.

Aspect 48. The method of any of Aspects 28 to 47, wherein determining the pose of the mobile device comprises: obtaining one or more radio frequency (RF) signals; and determining the pose of the mobile device based on one or more images of an interior portion of the vehicle and at least one of a round trip time associated with the one or more RF signals, a time of arrival associated with the one or more RF signals, and a received signal strength indicator (RSSI) associated with the one or more RF signals.

Aspect 49. The method of any of Aspects 28 to 48, wherein determining the pose of the mobile device comprises: receiving, from the vehicle, a vehicle template that includes one or more markers associated with the vehicle; and determining the pose of the mobile device relative to the coordinate system of the vehicle based on one or more images of an interior portion of the vehicle and the vehicle template.

Aspect 50. The method of Aspect 49, wherein the one or more markers comprise at least one of a visual pattern on at least one of an area within an interior portion of the vehicle and an object affixed to the interior portion of the vehicle, an element of the interior portion of the vehicle, a surface within the interior portion of the vehicle, and an illuminated object inside of the vehicle.

Aspect 51. The method of any of Aspects 49 to 50, wherein determining the pose of the mobile device comprises: detecting the one or more markers in the one or more images; and determining the pose of the mobile device relative to the coordinate system of the vehicle based on the detected one or more markers and the vehicle template.

Aspect 52. The method of any of Aspects 28 to 51, further comprising: obtaining, using one or more image sensors of the mobile device, a set of images of an interior portion of the vehicle, the set of images depicting one or more markers associated with the vehicle; and generating, based on the set of images, a vehicle template including the one or more markers.

Aspect 53. A non-transitory computer-readable medium having stored thereon instructions that, when executed by one or more processors, cause the one or more processors to perform a method according to any of Aspects 28 to 52.

Aspect 54. An apparatus comprising means for performing a method according to any of Aspects 28 to 52.

Aspect 55. An apparatus comprising: memory; and one or more processors coupled to the memory, the one or more processors being configured to: based on one or more images of an interior portion of a vehicle, determine a pose of the apparatus relative to a coordinate system of the vehicle; determine a state of an occupant of the vehicle; and send, to the vehicle, data indicating the state of the occupant and the pose of the apparatus relative to the coordinate system of the vehicle.

Aspect 56. The apparatus of Aspect 55, wherein the state of the occupant comprises an impairment of the occupant with regard to operating the vehicle.

Aspect 57. The apparatus of Aspect 56, wherein the impairment of the occupant includes any event, activity, distraction, state, attribute, behavior, and/or condition that would negatively impact the occupant's ability to safely operate the vehicle.

Aspect 58. The apparatus of any of Aspects 56 to 57, wherein the impairment comprises at least one of a state of distraction with respect to at least one of an operation of the vehicle and an event associated with the vehicle, an intoxicated state, a health condition, a wakefulness state, a detected emotional state, an impaired position to control the vehicle, and an impaired view.

Aspect 59. The apparatus of any of Aspects 56 to 58, wherein, to determine the state of the occupant, the one or more processors are configured to: receive, from the vehicle, data associated with one or more sensors of the vehicle; and determine the state of the occupant based on the data associated with the one or more sensors of the vehicle and the pose of the apparatus.

Aspect 60. The apparatus of Aspect 59, wherein the data associated with the one or more sensors of the vehicle indicates at least one of a state of the vehicle and an event associated with the vehicle.

Aspect 61. The apparatus of Aspect 60, wherein the event associated with the vehicle comprises at least one of a presence of an object within a path of the vehicle or a threshold proximity to the path of the vehicle, a traffic control associated with the path of the vehicle, and a failure by the vehicle to remain within at least one of a speed limit and a lane marking.

Aspect 62. The apparatus of Aspect 61, wherein the object within the path of the vehicle or the threshold proximity to the path of the vehicle comprises at least one of a pedestrian, an animal, and another vehicle.

Aspect 63. The apparatus of any of Aspects 56 to 62, wherein the impairment of the occupant includes any event, activity, distraction, state, attribute, behavior, and/or condition that would negatively impact the occupant's ability to safely operate the vehicle.

Aspect 64. The apparatus of any of Aspects 55 to 63, wherein the one or more processors are configured to: determine an eye gaze of the occupant of the vehicle, wherein the state of the occupant comprises the eye gaze of the occupant, wherein the occupant is associated with the apparatus.

Aspect 65. The apparatus of any of Aspects 55 to 64, wherein, to determine the state of the occupant, the one or more processors are configured to: receive, from one or more sensors associated with at least one of the apparatus and a wearable device worn by the occupant, one or more health measurements associated with the occupant; and determine the state of the occupant based on the one or more health measurements.

Aspect 66. The apparatus of Aspect 65, wherein the one or more health measurements comprise at least one of a heart rate, a blood pressure, a body temperature, a galvanic skin response, a measurement of an electrical signal from a heart of the occupant, a measurement of electrical activity of a brain of the occupant, an amount of eye redness, and a pupil size.

Aspect 67. The apparatus of any of Aspects 55 to 66, wherein, to determine the state of the occupant, the one or more processors are configured to: determine that an eye gaze of the occupant is focused away from a road ahead of the vehicle for a period of time; and determine an impaired state of the occupant based on the eye gaze of the occupant being focused away from the road ahead of the vehicle for the period of time and a determination that the period of time exceeds a threshold period of time.

Aspect 68. The apparatus of Aspect 67, wherein, to determine that the eye gaze of the occupant is focused away from the road ahead of the vehicle for the period of time, the one or more processors are configured to: determine that the eye gaze of the occupant is focused on virtual content rendered by the apparatus for at least a portion of the period of time.

Aspect 69. The apparatus of any of Aspects 67 to 68, wherein, to determine that the eye gaze of the occupant is focused away from the road ahead of the vehicle for the period of time, the one or more processors are configured to: determine that the eye gaze of the occupant is focused in a different direction than a direction of an obstacle within a path of the vehicle or a threshold proximity to the path of the vehicle.

Aspect 70. The apparatus of any of Aspects 55 to 69, wherein the one or more processors are configured to: send an indication of the state of the occupant to at least one of a second vehicle, a vehicle infrastructure system, a first remote device associated with a second occupant of the second vehicle, and a second remote device associated with a pedestrian.

Aspect 71. The apparatus of any of Aspects 55 to 70, wherein, to determine the state of the occupant, the one or more processors are configured to: determine an eye gaze of the occupant wearing the apparatus; and determine the state of the occupant based on the pose of the apparatus and the eye gaze of the occupant.

Aspect 72. The apparatus of any of Aspects 55 to 71, wherein, to determine the pose of the apparatus, the one or more processors are configured to: receive, from the vehicle, a vehicle template that includes one or more markers associated with the vehicle; and determine the pose of the apparatus relative to the coordinate system of the vehicle based on the one or more images and the vehicle template.

Aspect 73. The apparatus of Aspect 72, wherein the one or more markers comprise at least one of a visual pattern on at least one of an area within the interior portion of the vehicle and an object affixed to the interior portion of the vehicle, an element of the interior portion of the vehicle, a surface within the interior portion of the vehicle, and an illuminated object inside of the vehicle.

Aspect 74. The apparatus of Aspect 72, wherein the one or more images depict the one or more markers, and wherein, to determine the pose of the apparatus, the one or more processors are configured to: detect the one or more markers in the one or more images; and determine the pose of the apparatus relative to the coordinate system of the vehicle based on the detected one or more markers and the vehicle template.

Aspect 75. The apparatus of any of Aspects 55 to 74, wherein the one or more processors are configured to: obtain, using one or more image sensors of the apparatus, a set of images of the interior portion of the vehicle, the set of images depicting one or more visual landmarks associated with the vehicle; and generate a vehicle template based on the set of images, the vehicle template including the one or more visual landmarks.

Aspect 76. The apparatus of any of Aspects 55 to 75, wherein, to determine the pose of the apparatus, the one or more processors are configured to: obtain inertial sensor data associated with the apparatus; and determine the pose of the apparatus based on the one or more images and the inertial sensor data.

Aspect 77. The apparatus of any of Aspects 55 to 76, wherein the apparatus comprises a head-mounted display.

Aspect 78. A method comprising: based on one or more images of an interior portion of a vehicle, determining a pose of a mobile device relative to a coordinate system of the vehicle; determining a state of an occupant of the vehicle; and sending, to the vehicle, data indicating the state of the occupant and the pose of the mobile relative to the coordinate system of the vehicle.

Aspect 79. The method of Aspect 78, wherein the state of the occupant comprises an impairment of the occupant with regard to operating the vehicle.

Aspect 80. The method of any of Aspects 78 to 79, wherein the impairment of the occupant includes any event, activity, distraction, state, attribute, behavior, and/or condition that would negatively impact the occupant's ability to safely operate the vehicle.

Aspect 81. The method of any of Aspects 78 to 80, wherein the impairment comprises at least one of a state of distraction with respect to at least one of an operation of the vehicle and an event associated with the vehicle, an intoxicated state, a health condition, a wakefulness state, a detected emotional state, an impaired position to control the vehicle, and an impaired view.

Aspect 82. The method of any of Aspects 78 to 81, wherein determining the state of the occupant comprises: receiving, from the vehicle, data associated with one or more sensors of the vehicle; and determining the state of the occupant based on the data associated with the one or more sensors of the vehicle and the pose of the mobile device.

Aspect 83. The method of Aspect 82, wherein the data associated with the one or more sensors of the vehicle indicates at least one of a state of the vehicle and an event associated with the vehicle.

Aspect 84. The method of Aspect 83, wherein the event associated with the vehicle comprises at least one of a presence of an object within a path of the vehicle or a threshold proximity to the path of the vehicle, a traffic control associated with the path of the vehicle, and a failure by the vehicle to remain within at least one of a speed limit and a lane marking.

Aspect 85. The method of Aspect 84, wherein the object within the path of the vehicle or the threshold proximity to the path of the vehicle comprises at least one of a pedestrian, an animal, and another vehicle.

Aspect 86. The method of any of Aspects 78 to 85, further comprising: determining an eye gaze of the occupant of the vehicle, wherein the state of the occupant comprises the eye gaze of the occupant, wherein the occupant is associated with the mobile device.

Aspect 87. The method of any of Aspects 78 to 86, wherein determining the state of the occupant comprises: receiving, from one or more sensors associated with at least one of the mobile device and a wearable device worn by the occupant, one or more health measurements associated with the occupant; and determining the state of the occupant based on the one or more health measurements.

Aspect 88. The method of Aspect 87, wherein the one or more health measurements comprise at least one of a heart rate, a blood pressure, a body temperature, a galvanic skin response, a measurement of an electrical signal from a heart of the occupant, a measurement of electrical activity of a brain of the occupant, an amount of eye redness, and a pupil size.

Aspect 89. The method of any of Aspects 78 to 87, wherein determining the state of the occupant comprises: determining that an eye gaze of the occupant is focused away from a road ahead of the vehicle for a period of time; and determining an impaired state of the occupant based on the eye gaze of the occupant being focused away from the road ahead of the vehicle for the period of time and a determination that the period of time exceeds a threshold period of time.

Aspect 90. The method of Aspect 89, wherein determining that the eye gaze of the occupant is focused away from the road ahead of the vehicle for the period of time comprises: determining that the eye gaze of the occupant is focused on virtual content rendered by the mobile device for at least a portion of the period of time.

Aspect 91. The method of Aspect 89, wherein determining that the eye gaze of the occupant is focused away from the road ahead of the vehicle for the period of time comprises: determining that the eye gaze of the occupant is focused in a different direction than a direction of an obstacle within a path of the vehicle or a threshold proximity to the path of the vehicle.

Aspect 92. The method of any of Aspects 78 to 91, further comprising: sending an indication of the state of the occupant to at least one of a second vehicle, a vehicle infrastructure system, a first remote device associated with a second occupant of the second vehicle, and a second remote device associated with a pedestrian.

Aspect 93. The method of any of Aspects 78 to 92, wherein determining the state of the occupant comprises: determining an eye gaze of the occupant wearing the mobile device; and determining the state of the occupant based on the pose of the mobile device and the eye gaze of the occupant.

Aspect 94. The method of any of Aspects 78 to 93, wherein determining the pose of the mobile device comprises: receiving, from the vehicle, a vehicle template that includes one or more markers associated with the vehicle; and determining the pose of the mobile device relative to the coordinate system of the vehicle based on the one or more images and the vehicle template.

Aspect 95. The method of Aspect 94, wherein the one or more markers comprise at least one of a visual pattern on at least one of an area within the interior portion of the vehicle and an object affixed to the interior portion of the vehicle, an element of the interior portion of the vehicle, a surface within the interior portion of the vehicle, and an illuminated object inside of the vehicle.

Aspect 96. The method of Aspect 94, wherein the one or more images depict the one or more markers, and wherein determining the pose of the mobile device comprises: detecting the one or more markers in the one or more images; and determining the pose of the mobile device relative to the coordinate system of the vehicle based on the detected one or more markers and the vehicle template.

Aspect 97. The method of any of Aspects 78 to 96, further comprising: obtaining, using one or more image sensors of the mobile device, a set of images of the interior portion of the vehicle, the set of images depicting one or more visual landmarks associated with the vehicle; and generating a vehicle template based on the set of images, the vehicle template including the one or more visual landmarks.

Aspect 98. The method of any of Aspects 78 to 97, wherein determining the pose of the mobile device comprises: obtaining inertial sensor data associated with the mobile device; and determining the pose of the mobile device based on the one or more images and the inertial sensor data.

Aspect 99. The method of any of Aspects 78 to 98, wherein the impairment of the occupant includes any event, activity, distraction, state, attribute, behavior, and/or condition that would negatively impact the occupant's ability to safely operate the vehicle.

Aspect 100. A non-transitory computer-readable medium having stored thereon instructions that, when executed by one or more processors, cause the one or more processors to perform a method according to any of Aspects 78 to 99.

Aspect 101. An apparatus comprising means for performing a method according to any of Aspects 78 to 99.

Aspect 102. A method for controlling one or more operations of a vehicle, the method comprising: receiving, from a mobile device associated with an occupant of a vehicle, a pose of the occupant relative to a coordinate system of the vehicle; and based on the pose of the occupant relative to the coordinate system of the vehicle, controlling one or more functions of the vehicle.

Aspect 103. The method of Aspect 102, wherein controlling the one or more functions of the vehicle comprises engaging one or more vehicle functions of the vehicle.

Aspect 104. The method of Aspect 103, wherein the one or more vehicle functions comprise at least one of an autopilot function, a traction control function, a cruise control function, a collision avoidance function, a lane departure function, a lane centering function, a brake assist function, a lane-keeping function, a highway assist function, a lane change assistance function, a speed adaptation function, and an intersection assistance function.

Aspect 105. The method of any of Aspects 102 to 104, wherein controlling the operation of the vehicle comprises controlling or engaging one or more autonomous vehicle systems of the vehicle.

Aspect 106. The method of Aspect 105, wherein the one or more autonomous vehicle systems comprise at least one of a blind spot monitoring system, a driver monitoring system, a braking system, an autonomous driving control system, a driver assistance system, a navigation system, a steering control system, a vehicular communication system, and an automotive head-up display.

Aspect 107. The method of any of Aspects 102 to 106, further comprising sending data associated with one or more sensors of the vehicle to at least one of the mobile device, a second vehicle, a vehicle infrastructure system, a first remote device associated with a second occupant of the second vehicle, and a second remote device associated with a pedestrian.

Aspect 108. The method of any of Aspects 102 to 107, further comprising sending data indicating a state of the occupant to at least one of a second vehicle, a vehicle infrastructure system, a first remote device associated with a second occupant of the second vehicle, and a second remote device associated with a pedestrian.

Aspect 109. The method of any of Aspects 102 to 108, further comprising sending, to the mobile device, a vehicle template for determining the pose of the occupant relative to the coordinate system of the vehicle, the vehicle template including one or more markers associated with the vehicle.

Aspect 110. The method of Aspect 109, wherein the one or more markers comprise at least one of a visual pattern on at least one of an area within an interior portion of the vehicle and an object affixed to the interior portion of the vehicle, an element of the interior portion of the vehicle, a surface within the interior portion of the vehicle, and an illuminated object inside of the vehicle.

Aspect 111. The method of Aspect 109, further comprising generating an output based at least partly on the pose of the occupant relative to the coordinate system of the vehicle, the output comprising at least one of a communication to the mobile device, an instruction to modify the one or more functions of the vehicle, and an indication of a state of the occupant.

Aspect 112. The method of Aspect 111, wherein the communication to the mobile device comprises at least one of a virtual content item and a request to display the virtual content item.

Aspect 113. The method of any of Aspects 102 to 112, further comprising receiving, from the mobile device, data indicating a state of the occupant of the vehicle, wherein the data comprises at least one of sensor data from one or more sensors of the mobile device and processed data generated based on the sensor data from the one or more sensors of the mobile device.

Aspect 114. The method of Aspect 113, wherein the processed data comprises at least one of a description of the state of the occupant and a classification output identifying the state of the occupant.

Aspect 115. The method of any of Aspects 102 to 114, further comprising receiving, from the mobile device, data indicating a state of the occupant of the vehicle, wherein the data comprises at least one of an indication of an eye gaze of the occupant, the pose of the mobile device relative to the coordinate system of the vehicle, and one or more health measurements associated with the occupant.

Aspect 116. The method of Aspect 115, wherein the one or more health measurements comprise at least one of a heart rate, a blood pressure, a body temperature, a galvanic skin response, a measurement of an electrical signal from a heart of the occupant, a measurement of electrical activity of a brain of the occupant, an amount of eye redness, and a pupil size.

Aspect 117. The method of any of Aspects 102 to 116, further comprising obtaining, from one or more sensors of the vehicle, sensor data comprising at least one of an indication of an event related to an operation of the vehicle, an indication of one or more driving patterns during one or more operations of the vehicle controlled at least partly by the occupant, and vehicle instrumentation data, and controlling the one or more functions of the vehicle further based on the sensor data.

Aspect 118. The method of Aspect 117, further comprising determining a state of the occupant, wherein determining the state of the occupant comprises receiving, from one or more health sensors associated with at least one of the mobile device and a wearable device, one or more health measurements associated with the occupant; and determine the state of the occupant based on the one or more health measurements associated with the occupant.

Aspect 119. The method of any of Aspects 102 to 118, further comprising obtaining a state of the occupant, wherein the state of the occupant comprises an impairment of the occupant with regard to operating the vehicle.

Aspect 120. The method of Aspect 119, wherein the impairment of the occupant comprises an impairment of the occupant. In some examples, the impairment can include a transient impairment.

Aspect 121. The method of Aspect 119, wherein the impairment comprises at least one of a state of distraction with respect to at least one of an operation of the vehicle and an event associated with the vehicle, an intoxicated state, a health condition, a wakefulness state, a detected emotional state, an impaired position to control the vehicle, and an impaired view.

Aspect 122. The method of Aspect 121, wherein the event comprises at least one of a presence of an object within a path of the vehicle or a threshold proximity to the path of the vehicle, a traffic control associated with the path of the vehicle, and a failure by the vehicle to remain within at least one of a speed limit and a lane marking.

Aspect 123. The method of Aspect 122, wherein the object comprises at least one of a pedestrian, an animal, and another vehicle.

Aspect 124. The method of any of Aspects 102 to 123, further comprising obtaining one or more images of an interior portion of the vehicle, the one or more images depicting one or more visual landmarks associated with the vehicle; and generating a vehicle template based on the one or more images, the vehicle template describing the one or more visual landmarks.

Aspect 125. The method of Aspect 124, further comprising sending the vehicle template to the mobile device; and receiving, from the mobile device, the pose of the occupant relative to one or more coordinates defined in the vehicle template, wherein the one or more coordinates are relative to the one or more visual landmarks and correspond to the coordinate system of the vehicle.

Aspect 126. The method of Aspect 125, further comprising receiving, from the mobile device, data indicating a state of the occupant, wherein controlling one or more functions of the vehicle comprises controlling the one or more functions of the vehicle based on the pose of the occupant and the data indicating the state of the occupant.

Aspect 127. The method of Aspect 126, further comprising: generating an output based at least partly on the pose of the occupant relative to the coordinate system of the vehicle, the output comprising at least one of an instruction to modify the one or more functions of the vehicle and an updated state of the occupant.

Aspect 128. The method of any of Aspects 102 to 128, wherein the one or more functions of the vehicle are controlled via a computer system of the vehicle configured to control at least one of the one or more functions of the vehicle and one or more autonomous vehicle systems of the vehicle.

Aspect 129. The method of any of Aspects 102 to 128, wherein the mobile device comprises a wearable augmented reality device.

Aspect 130. The method of any of Aspects 102 to 129, wherein the mobile device comprises a head-mounted display.

Aspect 131. The method of any of Aspects 119 to 121, wherein the impairment of the occupant includes any event, activity, distraction, state, attribute, behavior, and/or condition that would negatively impact the occupant's ability to safely operate the vehicle.

Aspect 132. An apparatus comprising memory and one or more processors coupled to the memory, the one or more processors being configured to perform a method according to any of Aspects 102 to 131.

Aspect 133. An apparatus comprising means for performing a method according to any of Aspects 102 to 131.

Aspect 134. A non-transitory computer-readable medium having stored thereon instructions that, when executed by one or more processors, cause the one or more processors to perform a method according to any of Aspects 102 to 131.

Aspect 135. A method for providing vehicle data to a device associated with an occupant of a vehicle, the method comprising: receiving a request from an augmented reality (AR) device connected with a computer system of a vehicle; and in response to the request, sending, to the AR device, data associated with one or more sensors of the vehicle.

Aspect 136. The method of Aspect 135, wherein the data comprises vehicle data indicating a context of the vehicle, and wherein the context of the vehicle comprises at least one of a state of the vehicle and one or more events encountered by the vehicle or determined to occur during one or more operations of the vehicle.

Aspect 137. The method of Aspect 136, wherein the one or more events comprise at least one of a presence of an object within a path of the vehicle or a threshold proximity to the path of the vehicle, a traffic control associated with the path of the vehicle, and a failure by the vehicle to remain within at least one of a speed limit and a lane marking.

Aspect 138. The method of Aspect 137, wherein the object within the path of the vehicle or the threshold proximity to the path of the vehicle comprises at least one of a pedestrian, an animal, and another vehicle.

Aspect 139. The method of Aspect 136, further comprising: sending, to the AR device, display data for presentation at a location relative to at least one of a pose of the AR device relative to a coordinate system of the vehicle and a respective location of the one or more events, the display data comprising at least a portion of the vehicle data.

Aspect 140. The method of Aspect 139, further comprising: sending, to the AR device, an indication of the respective location of the one or more events.

Aspect 141. The method of any of Aspects 135 to 140, further comprising: sending, to the AR device, a vehicle template for determining a pose of the AR device relative to a coordinate system of the vehicle, the vehicle template describing one or more markers in an interior portion of the vehicle.

Aspect 142. The method of Aspect 141, wherein the one or more markers comprise at least one of a visual pattern on at least one of an area within the interior portion of the vehicle and an object affixed to the interior portion of the vehicle, an element of the interior portion of the vehicle, a surface within the interior portion of the vehicle, and an illuminated object inside of the vehicle.

Aspect 143. The method of Aspect 141, further comprising: receiving, from the AR device, the pose of the AR device relative to the coordinate system of the vehicle.

Aspect 144. The method of Aspect 143, further comprising: controlling, based on at least one of the data associated with the one or more sensors and the pose of the AR device relative to the coordinate system of the vehicle, a presentation by the computer system of virtual content associated with the vehicle.

Aspect 145. The method of Aspect 144, wherein controlling the presentation of virtual content comprises: based on the pose of the AR device relative to the coordinate system of the vehicle, providing, to the AR device, a live content feed from one or more image sensors of the vehicle.

Aspect 146. The method of Aspect 145, wherein providing the live content feed comprises: determining a pose of the AR device relative to the vehicle event based on the pose of the AR device relative to the coordinate system of the vehicle and a position of the vehicle relative to the vehicle event; and based on the pose of the AR device relative to the vehicle event, determining that virtual content associated with at least one of the computer system and the AR device at least partly occludes the vehicle event in a field-of-view of the AR device.

Aspect 147. The method of Aspect 144, wherein controlling the presentation of virtual content comprises: associating a location of a virtual content item rendered by the computer system with a location of the vehicle event relative to the coordinate system of the vehicle; and filtering or modifying the virtual content item based on the association of the location of the virtual content with the location of the vehicle event relative to the coordinate system of the vehicle.

Aspect 148. The method of Aspect 147, wherein filtering or modifying the virtual content item comprises: modifying one or more characteristics of the virtual content item, the one or more characteristics comprising at least one of a transparency, a size, a location of the virtual content item, and a brightness level.

Aspect 149. The method of Aspect 147, wherein filtering or modifying the virtual content item comprises: receiving an eye gaze of the occupant of the vehicle; determining a visibility of the vehicle event to the occupant based on the eye gaze of the occupant and the location of the vehicle event; and filtering or modifying the virtual content item further based on the visibility of the vehicle event to the occupant.

Aspect 150. The method of Aspect 144, wherein controlling the presentation of virtual content comprises: receiving an eye gaze of the occupant of the vehicle; and rendering virtual content within a direction of the eye gaze of the occupant of the vehicle.

Aspect 151. The method of Aspect 150, wherein rendering the virtual content comprises: rendering a virtual content overlay comprising a virtual indicator of at least one of a vehicle event, a location of the vehicle event, and a direction of the vehicle event.

Aspect 152. The method of Aspect 151, wherein rendering the virtual content comprises: modifying one or more characteristics of the virtual content, the one or more characteristics comprising at least one of a transparency, a size, a location of the virtual content, and a brightness level.

Aspect 153. The method of any of Aspects 135 to 152, further comprising: sending, to one or more display devices, an instruction to display, a virtual content item that provides information about an operation of the vehicle, the instruction indicating a placement of the virtual content item relative to a location in the vehicle that is within a field-of-view of the occupant.

Aspect 154. The method of Aspect 153, wherein the virtual content item comprises at least one of a first indication of a vehicle event detected by the computer system, a second indication of a context of the vehicle, and an alert associated with the context of the vehicle.

Aspect 155. The method of any of Aspects 135 to 154, further comprising: receiving a camera feed from a camera device on the vehicle; and sending, to the AR device, at least a portion of the camera feed for display.

Aspect 156. The method of any of Aspects 135 to 155, further comprising sending, to the AR device, an indication of a state of the occupant.

Aspect 157. The method of Aspect 156, wherein the state of the occupant comprises an impairment of the occupant with regard to operating the vehicle.

Aspect 158. The method of Aspect 157, wherein the impairment comprises at least one of a state of distraction with respect to at least one of an operation of the vehicle and an event associated with the vehicle, an intoxicated state, a health condition, a wakefulness state, a detected emotional state, an impaired position to control the vehicle, and an impaired view.

Aspect 159. The method of Aspect 157, further comprising controlling an operation of the vehicle based on the impairment of the occupant.

Aspect 160. The method of Aspect 157, further comprising generating display data based on the impairment of the occupant, the display data comprising at least one of a vehicle event and vehicle instrumentation data.

Aspect 161. The method of Aspect 157, further comprising sending, to the AR device, display data based on the impairment of the occupant, the display data comprising at least one of a vehicle event and vehicle instrumentation data.

Aspect 162. The method of any of Aspects 135 to 161, wherein the computer system is configured to control at least one of one or more autonomous functions of the vehicle and one or more autonomous vehicle systems of the vehicle.

Aspect 163. The method of any of Aspects 135 to 162, wherein the AR device comprises a head-mounted display.

Aspect 164. The method of any of Aspects 135 to 163, wherein the AR device comprises a wearable AR device.

Aspect 165. The method of Aspect 157 to 158, wherein the impairment of the occupant includes any event, activity, distraction, state, attribute, behavior, and/or condition that would negatively impact the occupant's ability to safely operate the vehicle.

Aspect 166. An apparatus comprising memory and one or more processors coupled to the memory, the one or more processors being configured to perform a method according to any of Aspects 135 to 165.

Aspect 167. An apparatus comprising means for performing a method according to any of Aspects 135 to 165.

Aspect 168. A non-transitory computer-readable medium having stored thereon instructions that, when executed by one or more processors, cause the one or more processors to perform a method according to any of Aspects 135 to 165.

Aspect 169: A method comprising determining, based on one or more images of an interior portion of a vehicle, a position of a mobile device relative to a coordinate system of the vehicle. The method can further include receiving, from the vehicle, data associated with one or more sensors of the vehicle; and displaying, using a display device of the apparatus, virtual content based on the data associated with the one or more sensors and the position of the apparatus relative to the coordinate system of the vehicle. Additionally or alternatively, the method can further include determining a state of an occupant of the vehicle; and sending, to the vehicle, data indicating the state of the occupant and the position of the mobile device relative to the coordinate system of the vehicle.

Aspect 170. The method of Aspect 169, further comprising a method according to any of Aspects 28 to 52 and/or Aspects 78 to 99.

Aspect 171. An apparatus comprising memory and one or more processors coupled to the memory, the one or more processors being configured to perform a method according to any of Aspects 169 to 170.

Aspect 172. An apparatus comprising means for performing a method according to any of Aspects 169 to 170.

Aspect 173. A non-transitory computer-readable medium having stored thereon instructions that, when executed by one or more processors, cause the one or more processors to perform a method according to any of Aspects 169 to 170.

Aspect 174. A method comprising determining, based on one or more images of an interior portion of a vehicle, a position of a mobile device relative to a coordinate system of the vehicle. The method can further include determining a state of an occupant of the vehicle; and sending, to the vehicle, data indicating the state of the occupant and the position of the mobile device relative to the coordinate system of the vehicle. Additionally or alternatively, the method can further include receiving, from the vehicle, data associated with one or more sensors of the vehicle; and displaying, using a display device of the apparatus, virtual content based on the data associated with the one or more sensors and the position of the apparatus relative to the coordinate system of the vehicle.

Aspect 175. The method of Aspect 174, further comprising a method according to any of Aspects 28 to 52 and/or Aspects 78 to 99.

Aspect 176. An apparatus comprising memory and one or more processors coupled to the memory, the one or more processors being configured to perform a method according to any of Aspects 174 to 175.

Aspect 177. An apparatus comprising means for performing a method according to any of Aspects 174 to 175.

Aspect 180. A non-transitory computer-readable medium having stored thereon instructions that, when executed by one or more processors, cause the one or more processors to perform a method according to any of Aspects 174 to 175.

Aspect 181. A method comprising: receiving, from a mobile device associated with an occupant of a vehicle, a pose of the occupant relative to a coordinate system of the vehicle; and based on the pose of the occupant relative to the coordinate system of the vehicle, controlling one or more functions of the vehicle. Additionally or alternatively, the method can further include receiving a request from an augmented reality (AR) device connected with a computer system of a vehicle; and in response to the request, sending, to the AR device, data associated with one or more sensors of the vehicle.

Aspect 182. The method of Aspect 181, further comprising a method according to any of Aspects 102 to 131 and/or Aspects 135 to 165.

Aspect 183. An apparatus comprising memory and one or more processors coupled to the memory, the one or more processors being configured to perform a method according to any of Aspects 181 to 182.

Aspect 184. An apparatus comprising means for performing a method according to any of Aspects 181 to 182.

Aspect 185. A non-transitory computer-readable medium having stored thereon instructions that, when executed by one or more processors, cause the one or more processors to perform a method according to any of Aspects 181 to 182.

Aspect 186. A method comprising: receiving a request from an augmented reality (AR) device connected with a computer system of a vehicle; and in response to the request, sending, to the AR device, data associated with one or more sensors of the vehicle. Additionally or alternatively, the method can further include receiving, from a mobile device associated with an occupant of a vehicle, a pose of the occupant relative to a coordinate system of the vehicle; and based on the pose of the occupant relative to the coordinate system of the vehicle, controlling one or more functions of the vehicle.

Aspect 187. The method of Aspect 186, further comprising a method according to any of Aspects 102 to 131 and/or Aspects 135 to 165.

Aspect 183. An apparatus comprising memory and one or more processors coupled to the memory, the one or more processors being configured to perform a method according to any of Aspects 186 to 187.

Aspect 184. An apparatus comprising means for performing a method according to any of Aspects 186 to 187.

Aspect 185. A non-transitory computer-readable medium having stored thereon instructions that, when executed by one or more processors, cause the one or more processors to perform a method according to any of Aspects 186 to 187.

What is claimed is:

1. An apparatus comprising:
   memory; and
   one or more processors coupled to the memory, the one or more processors being configured to:
   determine a pose of the apparatus relative to a coordinate system of a vehicle based on one or more images of an interior portion of the vehicle and a vehicle template including information associated with the interior portion of the vehicle, the information associated with the interior portion of the vehicle comprising at least one of a visual pattern of an area within the interior portion of the vehicle, an object affixed to the interior portion of the vehicle, an element of the interior portion of the vehicle, a surface within the interior portion of the vehicle, and an illuminated object inside of the vehicle;
   determine a state of an occupant of the vehicle; and
   send, to the vehicle, data indicating the state of the occupant and the pose of the apparatus relative to the coordinate system of the vehicle.

2. The apparatus of claim 1, wherein the state of the occupant comprises an impairment of the occupant with regard to operating the vehicle.

3. The apparatus of claim 2, wherein the impairment comprises at least one of a state of distraction with respect to at least one of an operation of the vehicle and an event associated with the vehicle, an intoxicated state, a health condition, a wakefulness state, a detected emotional state, an impaired position to control the vehicle, and an impaired view.

4. The apparatus of claim 2, wherein, to determine the state of the occupant, the one or more processors are configured to:
   receive, from the vehicle, data associated with one or more sensors of the vehicle; and
   determine the state of the occupant based on the data associated with the one or more sensors of the vehicle and the pose of the apparatus.

5. The apparatus of claim 4, wherein the data associated with the one or more sensors of the vehicle indicates at least one of a state of the vehicle and an event associated with the vehicle.

6. The apparatus of claim 5, wherein the event associated with the vehicle comprises at least one of a presence of an object within a path of the vehicle or a threshold proximity to the path of the vehicle, a traffic control associated with the path of the vehicle, and a failure by the vehicle to remain within at least one of a speed limit and a lane marking.

7. The apparatus of claim 6, wherein the object within the path of the vehicle or the threshold proximity to the path of the vehicle comprises at least one of a pedestrian, an animal, and another vehicle.

8. The apparatus of claim 1, wherein the one or more processors are configured to:
   determine an eye gaze of the occupant of the vehicle, wherein the state of the occupant comprises the eye gaze of the occupant, wherein the occupant is associated with the apparatus.

9. The apparatus of claim 1, wherein, to determine the state of the occupant, the one or more processors are configured to:
   receive, from one or more sensors associated with at least one of the apparatus and a wearable device worn by the occupant, one or more health measurements associated with the occupant; and
   determine the state of the occupant based on the one or more health measurements.

10. The apparatus of claim 9, wherein the one or more health measurements comprise at least one of a heart rate, a blood pressure, a body temperature, a galvanic skin response, a measurement of an electrical signal from a heart of the occupant, a measurement of electrical activity of a brain of the occupant, an amount of eye redness, and a pupil size.

11. The apparatus of claim 1, wherein, to determine the state of the occupant, the one or more processors are configured to:
   determine that an eye gaze of the occupant is focused away from a road ahead of the vehicle for a period of time; and
   determine an impaired state of the occupant based on the eye gaze of the occupant being focused away from the road ahead of the vehicle for the period of time and a determination that the period of time exceeds a threshold period of time.

12. The apparatus of claim 11, wherein, to determine that the eye gaze of the occupant is focused away from the road ahead of the vehicle for the period of time, the one or more processors are configured to:
   determine that the eye gaze of the occupant is focused on virtual content rendered by the apparatus for at least a portion of the period of time.

13. The apparatus of claim 11, wherein, to determine that the eye gaze of the occupant is focused away from the road ahead of the vehicle for the period of time, the one or more processors are configured to:
   determine that the eye gaze of the occupant is focused in a different direction than a direction of an obstacle within a path of the vehicle or a threshold proximity to the path of the vehicle.

14. The apparatus of claim 1, wherein the one or more processors are configured to:
   send an indication of the state of the occupant to at least one of a second vehicle, a vehicle infrastructure system, a first remote device associated with a second occupant of the second vehicle, and a second remote device associated with a pedestrian.

15. The apparatus of claim 1, wherein, to determine the state of the occupant, the one or more processors are configured to:
   determine an eye gaze of the occupant wearing the apparatus; and
   determine the state of the occupant based on the pose of the apparatus and the eye gaze of the occupant.

16. The apparatus of claim 1, wherein the one or more processors are configured to:
   receive the vehicle template from the vehicle.

17. The apparatus of claim 1, wherein the one or more images depict the information associated with the interior portion of the vehicle, and wherein, to determine the pose of the apparatus, the one or more processors are configured to:
   detect the information associated with the interior portion of the vehicle in the one or more images; and
   determine the pose of the apparatus relative to the coordinate system of the vehicle based on the detected information associated with the interior portion of the vehicle.

18. The apparatus of claim 1, wherein the one or more processors are configured to:
   obtain, from the one or more images, a set of images of the interior portion of the vehicle depicting the visual pattern, the visual pattern comprising one or more visual landmarks associated with the vehicle; and
   generate the vehicle template based on the set of images.

19. The apparatus of claim 1, wherein, to determine the pose of the apparatus, the one or more processors are configured to:
   obtain inertial sensor data associated with the apparatus; and
   determine the pose of the apparatus further based on the inertial sensor data.

20. The apparatus of claim 1, wherein the apparatus comprises a head-mounted display.

21. A method comprising:
   determining a pose of a mobile device relative to a coordinate system of a vehicle based on one or more images of an interior portion of the vehicle and a vehicle template including information associated with the interior portion of the vehicle, the information associated with the interior portion of the vehicle comprising at least one of a visual pattern of an area within the interior portion of the vehicle, an object affixed to the interior portion of the vehicle, an element of the interior portion of the vehicle, a surface within the interior portion of the vehicle, and an illuminated object inside of the vehicle;
   determining a state of an occupant of the vehicle; and
   sending, to the vehicle, data indicating the state of the occupant and the pose of the mobile device relative to the coordinate system of the vehicle.

22. The method of claim 21, wherein the state of the occupant comprises an impairment of the occupant with regard to operating the vehicle.

23. The method of claim 22, wherein the impairment comprises at least one of a state of distraction with respect to at least one of an operation of the vehicle and an event associated with the vehicle, an intoxicated state, a health condition, a wakefulness state, a detected emotional state, an impaired position to control the vehicle, and an impaired view.

24. The method of claim 22, wherein determining the state of the occupant comprises:
   receiving, from the vehicle, data associated with one or more sensors of the vehicle; and
   determining the state of the occupant based on the data associated with the one or more sensors of the vehicle and the pose of the mobile device.

25. The method of claim 24, wherein the data associated with the one or more sensors of the vehicle indicates at least one of a state of the vehicle and an event associated with the vehicle.

26. The method of claim 25, wherein the event associated with the vehicle comprises at least one of a presence of an object within a path of the vehicle or a threshold proximity to the path of the vehicle, a traffic control associated with the path of the vehicle, and a failure by the vehicle to remain within at least one of a speed limit and a lane marking.

27. The method of claim 26, wherein the object within the path of the vehicle or the threshold proximity to the path of the vehicle comprises at least one of a pedestrian, an animal, and another vehicle.

28. The method of claim 21, further comprising:
determining an eye gaze of the occupant of the vehicle, wherein the state of the occupant comprises the eye gaze of the occupant, wherein the occupant is associated with the mobile device.

29. The method of claim 21, wherein determining the state of the occupant comprises:
receiving, from one or more sensors associated with at least one of the mobile device and a wearable device worn by the occupant, one or more health measurements associated with the occupant; and
determining the state of the occupant based on the one or more health measurements.

30. The method of claim 29, wherein the one or more health measurements comprise at least one of a heart rate, a blood pressure, a body temperature, a galvanic skin response, a measurement of an electrical signal from a heart of the occupant, a measurement of electrical activity of a brain of the occupant, an amount of eye redness, and a pupil size.

31. The method of claim 21, wherein determining the state of the occupant comprises:
determining that an eye gaze of the occupant is focused away from a road ahead of the vehicle for a period of time; and
determining an impaired state of the occupant based on the eye gaze of the occupant being focused away from the road ahead of the vehicle for the period of time and a determination that the period of time exceeds a threshold period of time.

32. The method of claim 31, wherein determining that the eye gaze of the occupant is focused away from the road ahead of the vehicle for the period of time comprises:
determining that the eye gaze of the occupant is focused on virtual content rendered by the mobile device for at least a portion of the period of time.

33. The method of claim 31, wherein determining that the eye gaze of the occupant is focused away from the road ahead of the vehicle for the period of time comprises:
determining that the eye gaze of the occupant is focused in a different direction than a direction of an obstacle within a path of the vehicle or a threshold proximity to the path of the vehicle.

34. The method of claim 21, further comprising:
sending an indication of the state of the occupant to at least one of a second vehicle, a vehicle infrastructure system, a first remote device associated with a second occupant of the second vehicle, and a second remote device associated with a pedestrian.

35. The method of claim 21, wherein determining the state of the occupant comprises:
determining an eye gaze of the occupant wearing the mobile device; and
determining the state of the occupant based on the pose of the mobile device and the eye gaze of the occupant.

36. The method of claim 21, further comprising:
receiving the vehicle template from the vehicle.

37. The method of claim 22, wherein the one or more images depict the information associated with the interior portion of the vehicle, and wherein determining the pose of the mobile device comprises:
detecting the information associated with the interior portion of the vehicle in the one or more images; and
determining the pose of the mobile device relative to the coordinate system of the vehicle based on the detected information associated with the interior portion of the vehicle.

38. The method of claim 21, further comprising:
obtaining, from the one or more images, a set of images of the interior portion of the vehicle depicting the visual pattern, the visual pattern comprising one or more visual landmarks associated with the vehicle; and
generating the vehicle template based on the set of images.

39. The method of claim 21, wherein determining the pose of the mobile device comprises:
obtaining inertial sensor data associated with the mobile device; and
determining the pose of the mobile device further based on the inertial sensor data.

* * * * *